United States Patent [19]
Billiar et al.

[11] Patent Number: 5,658,565
[45] Date of Patent: Aug. 19, 1997

[54] INDUCIBLE NITRIC OXIDE SYNTHASE GENE FOR TREATMENT OF DISEASE

[75] Inventors: Timothy R. Billiar; Edith Tzeng, both of Pittsburgh, Pa.; Andreas K. Nüssler, Neu-Ulm, Germany; David A. Geller; Richard L. Simmons, both of Pittsburgh, Pa.

[73] Assignee: University of Pittsburgh of the Commonwealth System of Higher Education, Pittsburgh, Pa.

[21] Appl. No.: 265,046

[22] Filed: Jun. 24, 1994

[51] Int. Cl.$^6$ .................................................. A61K 48/00
[52] U.S. Cl. .................. 424/93.21; 424/93.2; 424/93.1; 514/44; 435/189; 435/191; 435/320.1; 435/172.3; 435/235.1; 536/23.1; 536/23.2; 536/23.5; 935/60; 935/22; 935/32; 935/9
[58] Field of Search ...................... 435/189, 191, 435/320.1, 235.1; 514/44; 424/423, 93.1, 93.2; 536/23.1, 23.2, 23.5; 935/9, 10, 14, 22, 23, 32

[56] References Cited

U.S. PATENT DOCUMENTS

| | | | |
|---|---|---|---|
| 5,132,407 | 7/1992 | Shuehr et al. | 530/395 |
| 5,252,479 | 10/1993 | Srivastava | 435/320.1 |
| 5,328,470 | 7/1994 | Nabel et al. | 604/101 |
| 5,428,070 | 6/1995 | Cooke et al. | 514/557 |

FOREIGN PATENT DOCUMENTS

92/07943  5/1992  WIPO .

OTHER PUBLICATIONS

Geller, et al., 1993, Molecular Cloning and Expression of Inducible Nitric Oxide Synthase from Human Hepatocytes, PNAS 90: 3491–3495.

Nussler, et al., 1992, Stimulation of the Nitric Oxide Synthase Pathway in Human Hepatocytes by Cytokines and Endotoxins, J. Exp. Med. 176: 261–264.

Lowenstein, et al., 1992, Cloned and Expressed Macrophage Nitric Oxide Synthase Contrasts with the Brain Enzyme, PNAS 89: 6711–6715.

Xie, et al., 1992, Cloning and Characterization of Inducible Nitric Oxide Synthase from Mouse Macrophages, Science 256: 225–228.

Lyons, et al., 1992, Molecular Cloning and Functional Expression of an Inducible Nitric Oxide Synthase from a Murine Macrophage Cell Line, J. Biol. Chem. 267: 6370–6374.

von der Leven, et al., 1994, In Vivo Gene Transfer to Prevent Neointima Hyperplasia after Vascular Injury: Effect of Overexpression of Constitutive Nitric Oxide Synthase, Faseb J. 8:A802 (#4651).

Bucala, et al., 1991, Advanced Glycosylation Products Quench Nitric Oxide and Mediate Defective Endothelium-Dependent Vasodilatatin in Experimental Diabetes, J. Clin. Invest. 87: 432–438.

Chin, et al., 1992, Inactivation of Endothelial Derived Relaxing Factor by Oxidized Lipoproteins, J. Clin. Invest. 89:10–18.

Chester, et al., 1990, Low Basal and Stimulted Release of Nitric Oxide in Atherosclerotic Epicardial Coronary Arteries, Lancet 336: 897–900.

Wilson, et al., 1989, Implantation of Vascular Grafts Lines with Genetically Modified Endothelial Cells, Science 244: 1344–1346.

Ignarro, et al., 1987, Endothelium–Derived Relaxing Factor Produced and Released from Artery and Vein is Nitric Oxide, PNAS 84: 9265–9269.

Radomski et al., 1987, The Anti–Aggregating Properties of Vascular Endothelium: Interactions Between Prostacyclin and Nitric Oxide, Br. J. Pharmac. 92: 639–646.

Nunokawa and Tanaka, 1992, Interferon–Gamma Inhibits Proliferation of Rat Vascular Smooth Muscle Cells by Nitric Oxide Generation, Biochem. Biophys. Res. Comm. 188: 409–415.

Werner–Felmayer, et al., 1990, Tetrahydrobiopterin–Dependent Formation of Nitrite and Nitrate in Murine Fibroblasts, J. Exp. Med. 172: 1599–1607.

Moncada, et al., 1991, Nitric Oxide: Physiology, Pathophysiology and, Pharmacology, Pharmacological Reviews 43: 109–142.

Nabel, et al., 1989, Recombinant Gene Expression In Vivo Within Endothelial Cells of the Arterial Wall, Science 244: 1342–1344.

Zwiebel, et al., 1989, High–Level Recombinant Gene Expression in Rabbit Endothelial Cells Transduced by Retroviral Vectors, Science 243: 220–222.

Nabel, et al., 1990, Site–Specific Gene Expression In Vivo by Direct Gene Transfer into the Artierial Wall, Science 249:1285–1288.

Nussler, et al., 1992, Stimulation of Nitric Oxide in Human Hepatocytes by Cytokines, Faseb J., 6 (5): A1834 (#5200).

Draiper, et al., 1991, L–arginine–derived Nitric Oxide and the Cell–Mediated Immune Response, Res. Immunol. 142: 553–602.

Janssens, et al., 1992, Cloning and Expression of a cDNA Encoding Human Endothelial–Derived Relaxing Factor/Nitric Oxide Synthase, J. Biol. Chem. 267: 14519–14522.

(List continued on next page.)

Primary Examiner—Christopher S.F. Low
Attorney, Agent, or Firm—Leydig, Voit & Mayer, Ltd.

[57] ABSTRACT

The present invention discloses a full-length human hepatocyte iNOS cDNA clone and various gene therapy applications utilizing an iNOS DNA sequence. In preferred embodiments of the disclosed invention, iNOS-directed gene therapy involves specific targeting of a DNA sequence encoding a protein or protein fragment with iNOS biological activity for treating vascular diseases and disorders, antitumor applications and in response to certain microbial infections.

40 Claims, 5 Drawing Sheets

OTHER PUBLICATIONS

Harbrecht, et al., Inhibition of Nitric Oxide Synthesis During Endotoxemia Promotes Intrahepatic Thrombosis and an Oxygen Radical–Mediated Hepatic Injury, J. Leuk. Biol. 52: 390–394.

Kilbourn, et al., 1990, NMA Inhibits Tumor Necrosis Factor–Induced Hypotension: Implications for the Involvement of Nitric Oxide, PNAS 87: 3629–3632.

Hibbs, et al., 1987, Macrophage Cytotoxicity: Role for L–Arginine Deiminase and Imino Nitrogen Oxidation to Nitrite, Science 235: 473–476.

Hibbs, et al., 1987, L–Arginine is Required for Expression of the Activated Macrophage Effector Mechanism Causing Selective Metabolic Inhibition in Targe Cells, J. Immun. 138: 550–565.

Curran, et al., 1989, Hepatocytes Produce Nitrogen Oxides from L–Arginine in Response to Inflammatory Products of Kupffer Cells, J. Exp. Med. 170: 1769–1774.

Billiar, et al., 1990, Inducible Cytosolic Enzyme Activity for the Production of Nitrogen Oxides from L–Arginine in Hepatocytes, Biochem. Biophys. Res. Comm. 168: 1034–1040.

Busse and Mülsch, 1990, Calcium–Dependent Nitric Oxide Synthesis in Endothelial Cytosol is Mediated by Calmodulin, Febs Letters 265: 133–136.

Nakayama, et al., 1992, Cytokines and Lipopolysaccharide Induce Nitric Oxide Snythase in Cultured Rat Pulmonary Artery Smooth Muscle, Am. J. Respir. Cell Mol. Biol. 7: 471–476.

Gross, et al., 1991, Cytokine–Activated Endothelial Cells Express an Isotype to Nitric Oxide Snythase which is Tetrahydrobiopertin–Dependent . . . , biochem. Biophys. Res. Comm. 178: 823–829.

Granger, et al., 1988, Specific Amino–Acid (L–Arginine) Requirement for Micorbiostatic Activity J. Clin. Invest. 81: 1129–1136.

Bredt, et al., 1991, Cloned and Expressed Nitric Oxide Synthase Structurally Resembles Cytochrome, P–450 Reductase, Nature 351: 714–718.

Green, et al., 1991, Cytokine–Induced Synthesis of Nitrogen Oxides in Macrophages: A Protective Host Response to *Leishmania* and Other Intracellular Pathogens, J. Leuk. Biol. 50: 93–103.

Miller, 1992, Retroviral Vectors, Current Topics in Microbiology and Immunology 158: 1–24.

Mannino and GouldFogerite, 1988, Liposome Mediated Gene Transfer, BioTechniques 6: 682–690.

Gao and Huang, 1991, A Novel Cationic Liposome Reagent for Efficient Transfection of Mammalian Cells, Biochem. Biophys. Res. Comm. 179: 280–285.

Muzyczka, 1992, Adeno–Associated with Virus Vectors, Current Topics in Microbiology and Immunology, 158: 97–129.

Danos and Mulligen, 1988, Safe and Efficient Generation of Recombinant Retroviruses with Amphotropic and Ecotropic Host Ranges, PNAS 85: 6460–6464.

Rosenberg, 1992, Immunization of Cancer Patients Using Autologous Cancer Cells Modified by Insertion of the Gene for Tumor Necrosis Factor, Human Gene Therapy 3: 57–73.

Palmer, et al., 1987, Nitric Oxide Release Accounts for the Biological Activity of Endothelium–Derived Relaxing Factor, Nature 327: 524–525.

McNamara, et al., 1993, L–Arginine Inhibits Ballon Catheter–Induced Intimal Hyperplasia, Biochem. Biophys. Res. Comm. 193(1): 291–296.

Mardsen, et al., 1992, Molecular Cloning and Characterization of Human Endothelial Nitric Oxide Synthase, FEBS Letters 307: 287–293.

Billiar, et al., 1990, Modulation of Nitrogen Oxide Synthesis *In Vivo:* NMA Inhibits Endotoxin–Induced Nitrite/Nitrate Biosynthesis While Promoting Hepatic Damage, J. Leuk. Biol. 48: 565–569.

Charles et al. 1993 Proc. Natl. Acad. Sci. USA 90, 11419–11423.

Stribling et al. 1992 Proc. Natl. Acad. Sci. USA 89, 11277–11281.

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
( A ) LENGTH: 4145 base pairs
( B ) TYPE: nucleic acid
( C ) STRANDEDNESS: double
( D ) TOPOLOGY: linear ( i i ) MOLECULE TYPE: cDNA
    ( A ) DESCRIPTION: Human Hepatocyte Inducible Nitric Oxide
        Synthase cDNA Clone ( i i i ) HYPOTHETICAL: NO ( i v ) ANTI-SENSE: NO ( v i ) ORIGINAL SOURCE:
    ( F ) TISSUE TYPE: Induced Human Hepatocyte RNA ( v i i ) IMMEDIATE SOURCE:
    ( A ) LIBRARY: Lambda Zap II cDNA
    ( B ) CLONE: pHINOS ( v i i i ) POSITION IN GENOME:
    ( A ) CHROMOSOME/SEGMENT: unknown
    ( B ) MAP POSITION: unknown
    ( C ) UNITS: unknown ( i x ) FEATURE:
    ( A ) NAME/KEY: CDS
    ( B ) LOCATION: 207..3668
    ( C ) IDENTIFICATION METHOD: Experiment ( x i ) SEQUENCE DESCRIPTION: SEQ ID NO:1:

```
CTGCTTTAAA ATCTCTCGGC CACCTTTGAT GAGGGGACTG GGCAGTTCTA GACAGTCCCG       60

AAGTTCTCAA GGCACAGGTC TCTTCCTGGT TTGACTGTCC TTACCCCGGG GAGGCAGTGC      120

AGCCAGCTGC AAGCCCCACA GTGAAGAACA TCTGAGCTCA AATCCAGATA AGTGACATAA      180

GTGACCTGCT TTGTAAAGCC ATAGAG ATG GCC TGT CCT TGG AAA TTT CTG TTC       233
                             Met Ala Cys Pro Trp Lys Phe Leu Phe
                              1                   5

AAG ACC AAA TTC CAC CAG TAT GCA ATG AAT GGG GAA AAA GAC ATC AAC        281
Lys Thr Lys Phe His Gln Tyr Ala Met Asn Gly Glu Lys Asp Ile Asn
 10              15                  20                  25

AAC AAT GTG GAG AAA GCC CCC TGT GCC ACC TCC AGT CCA GTG ACA CAG        329
Asn Asn Val Glu Lys Ala Pro Cys Ala Thr Ser Ser Pro Val Thr Gln
                 30                  35                  40

GAT GAC CTT CAG TAT CAC AAC CTC AGC AAG CAG CAG AAT GAG TCC CCG        377
Asp Asp Leu Gln Tyr His Asn Leu Ser Lys Gln Gln Asn Glu Ser Pro
             45                  50                  55

CAG CCC CTC GTG GAG ACG GGA AAG AAG TCT CCA GAA TCT CTG GTC AAG        425
Gln Pro Leu Val Glu Thr Gly Lys Lys Ser Pro Glu Ser Leu Val Lys
         60                  65                  70

CTG GAT GCA ACC CCA TTG TCC TCC CCA CGG CAT GTG AGG ATC AAA AAC        473
Leu Asp Ala Thr Pro Leu Ser Ser Pro Arg His Val Arg Ile Lys Asn
     75                  80                  85

TGG GGC AGC GGG ATG ACT TTC CAA GAC ACA CTT CAC CAT AAG GCC AAA        521
Trp Gly Ser Gly Met Thr Phe Gln Asp Thr Leu His His Lys Ala Lys
 90                  95                 100                 105

GGG ATT TTA ACT TGC AGG TCC AAA TCT TGC CTG GGG TCC ATT ATG ACT        569
Gly Ile Leu Thr Cys Arg Ser Lys Ser Cys Leu Gly Ser Ile Met Thr
                110                 115                 120

CCC AAA AGT TTG ACC AGA GGA CCC AGG GAC AAG CCT ACC CCT CCA GAT        617
Pro Lys Ser Leu Thr Arg Gly Pro Arg Asp Lys Pro Thr Pro Pro Asp
            125                 130                 135

GAG CTT CTA CCT CAA GCT ATC GAA TTT GTC AAC CAA TAT TAC GGC TCC        665
Glu Leu Leu Pro Gln Ala Ile Glu Phe Val Asn Gln Tyr Tyr Gly Ser
        140                 145                 150

TTC AAA GAG GCA AAA ATA GAG GAA CAT CTG GCC AGG GTG GAA GCG GTA        713
Phe Lys Glu Ala Lys Ile Glu Glu His Leu Ala Arg Val Glu Ala Val
    155                 160                 165

ACA AAG GAG ATA GAA ACA ACA GGA ACC TAC CAA CTG ACG GGA GAT GAG        761
```

|   |   |   |   |   |   |   |   |   |   |   |   |   |   |   |   |
|---|---|---|---|---|---|---|---|---|---|---|---|---|---|---|---|
| Thr | Lys | Glu | Ile | Glu | Thr | Thr | Gly | Thr | Tyr | Gln | Leu | Thr | Gly | Asp | Glu |
| 170 |  |  |  |  | 175 |  |  |  | 180 |  |  |  |  |  | 185 |

| CTC | ATC | TTC | GCC | ACC | AAG | CAG | GCC | TGG | CGC | AAT | GCC | CCA | CGC | TGC | ATT | 809 |
|---|---|---|---|---|---|---|---|---|---|---|---|---|---|---|---|---|
| Leu | Ile | Phe | Ala | Thr | Lys | Gln | Ala | Trp | Arg | Asn | Ala | Pro | Arg | Cys | Ile |  |
|  |  |  |  | 190 |  |  |  | 195 |  |  |  |  | 200 |  |  |  |

| GGG | AGG | ATC | CAG | TGG | TCC | AAC | CTG | CAG | GTC | TTC | GAT | GCC | CGC | AGC | TGT | 857 |
|---|---|---|---|---|---|---|---|---|---|---|---|---|---|---|---|---|
| Gly | Arg | Ile | Gln | Trp | Ser | Asn | Leu | Gln | Val | Phe | Asp | Ala | Arg | Ser | Cys |  |
|  |  |  | 205 |  |  |  |  | 210 |  |  |  |  |  | 215 |  |  |

| TCC | ACT | GCC | CGG | GAA | ATG | TTT | GAA | CAC | ATC | TGC | AGA | CAC | GTG | CGT | TAC | 905 |
|---|---|---|---|---|---|---|---|---|---|---|---|---|---|---|---|---|
| Ser | Thr | Ala | Arg | Glu | Met | Phe | Glu | His | Ile | Cys | Arg | His | Val | Arg | Tyr |  |
|  |  |  | 220 |  |  |  |  | 225 |  |  |  |  | 230 |  |  |  |

| TCC | ACC | AAC | AAT | GGC | AAC | ATC | AGG | TCG | GCC | ATC | ACC | GTG | TTC | CCC | CAG | 953 |
|---|---|---|---|---|---|---|---|---|---|---|---|---|---|---|---|---|
| Ser | Thr | Asn | Asn | Gly | Asn | Ile | Arg | Ser | Ala | Ile | Thr | Val | Phe | Pro | Gln |  |
|  | 235 |  |  |  |  | 240 |  |  |  |  | 245 |  |  |  |  |  |

| CGG | AGT | GAT | GGC | AAG | CAC | GAC | TTC | CGG | GTG | TGG | AAT | GCT | CAG | CTC | ATC | 1001 |
|---|---|---|---|---|---|---|---|---|---|---|---|---|---|---|---|---|
| Arg | Ser | Asp | Gly | Lys | His | Asp | Phe | Arg | Val | Trp | Asn | Ala | Gln | Leu | Ile |  |
| 250 |  |  |  |  | 255 |  |  |  |  | 260 |  |  |  |  | 265 |  |

| CGC | TAT | GCT | GGC | TAC | CAG | ATG | CCA | GAT | GGC | AGC | ATC | AGA | GGG | GAC | CCT | 1049 |
|---|---|---|---|---|---|---|---|---|---|---|---|---|---|---|---|---|
| Arg | Tyr | Ala | Gly | Tyr | Gln | Met | Pro | Asp | Gly | Ser | Ile | Arg | Gly | Asp | Pro |  |
|  |  |  |  | 270 |  |  |  |  | 275 |  |  |  |  |  | 280 |  |

| GCC | AAC | GTG | GAA | TTC | ACT | CAG | CTG | TGC | ATC | GAC | CTG | GGC | TGG | AAG | CCC | 1097 |
|---|---|---|---|---|---|---|---|---|---|---|---|---|---|---|---|---|
| Ala | Asn | Val | Glu | Phe | Thr | Gln | Leu | Cys | Ile | Asp | Leu | Gly | Trp | Lys | Pro |  |
|  |  |  |  | 285 |  |  |  |  | 290 |  |  |  |  | 295 |  |  |

| AAG | TAC | GGC | CGC | TTC | GAT | GTG | GTC | CCC | CTG | GTC | CTG | CAG | GCC | AAT | GGC | 1145 |
|---|---|---|---|---|---|---|---|---|---|---|---|---|---|---|---|---|
| Lys | Tyr | Gly | Arg | Phe | Asp | Val | Val | Pro | Leu | Val | Leu | Gln | Ala | Asn | Gly |  |
|  |  | 300 |  |  |  |  |  | 305 |  |  |  |  | 310 |  |  |  |

| CGT | GAC | CCT | GAG | CTC | TTC | GAA | ATC | CCA | CCT | GAC | CTT | GTG | CTT | GAG | GTG | 1193 |
|---|---|---|---|---|---|---|---|---|---|---|---|---|---|---|---|---|
| Arg | Asp | Pro | Glu | Leu | Phe | Glu | Ile | Pro | Pro | Asp | Leu | Val | Leu | Glu | Val |  |
|  |  | 315 |  |  |  |  | 320 |  |  |  |  | 325 |  |  |  |  |

| GCC | ATG | GAA | CAT | CCC | AAA | TAC | GAG | TGG | TTT | CGG | GAA | CTG | GAG | CTA | AAG | 1241 |
|---|---|---|---|---|---|---|---|---|---|---|---|---|---|---|---|---|
| Ala | Met | Glu | His | Pro | Lys | Tyr | Glu | Trp | Phe | Arg | Glu | Leu | Glu | Leu | Lys |  |
| 330 |  |  |  |  | 335 |  |  |  |  | 340 |  |  |  |  | 345 |  |

| TGG | TAC | GCC | CTG | CCT | GCA | GTG | GCC | AAC | ATG | CTG | CTT | GAG | GTG | GGC | GGC | 1289 |
|---|---|---|---|---|---|---|---|---|---|---|---|---|---|---|---|---|
| Trp | Tyr | Ala | Leu | Pro | Ala | Val | Ala | Asn | Met | Leu | Leu | Glu | Val | Gly | Gly |  |
|  |  |  |  | 350 |  |  |  |  | 355 |  |  |  |  | 360 |  |  |

| CTG | GAG | TTC | CCA | GGG | TGC | CCC | TTC | AAT | GGC | TGG | TAC | ATG | GGC | ACA | GAG | 1337 |
|---|---|---|---|---|---|---|---|---|---|---|---|---|---|---|---|---|
| Leu | Glu | Phe | Pro | Gly | Cys | Pro | Phe | Asn | Gly | Trp | Tyr | Met | Gly | Thr | Glu |  |
|  |  |  | 365 |  |  |  |  | 370 |  |  |  |  | 375 |  |  |  |

| ATC | GGA | GTC | CGG | GAC | TTC | TGT | GAC | GTC | CAG | CGC | TAC | AAC | ATC | CTG | GAG | 1385 |
|---|---|---|---|---|---|---|---|---|---|---|---|---|---|---|---|---|
| Ile | Gly | Val | Arg | Asp | Phe | Cys | Asp | Val | Gln | Arg | Tyr | Asn | Ile | Leu | Glu |  |
|  |  | 380 |  |  |  |  | 385 |  |  |  |  | 390 |  |  |  |  |

| GAA | GTG | GGC | AGG | AGA | ATG | GGC | CTG | GAA | ACG | CAC | AAG | CTG | GCC | TCG | CTC | 1433 |
|---|---|---|---|---|---|---|---|---|---|---|---|---|---|---|---|---|
| Glu | Val | Gly | Arg | Arg | Met | Gly | Leu | Glu | Thr | His | Lys | Leu | Ala | Ser | Leu |  |
|  | 395 |  |  |  |  | 400 |  |  |  |  | 405 |  |  |  |  |  |

| TGG | AAA | GAC | CAG | GCT | GTC | GTT | GAG | ATC | AAC | ATT | GCT | GTG | ATC | CAT | AGT | 1481 |
|---|---|---|---|---|---|---|---|---|---|---|---|---|---|---|---|---|
| Trp | Lys | Asp | Gln | Ala | Val | Val | Glu | Ile | Asn | Ile | Ala | Val | Ile | His | Ser |  |
| 410 |  |  |  |  | 415 |  |  |  |  | 420 |  |  |  |  | 425 |  |

| TTT | CAG | AAG | CAG | AAT | GTG | ACC | ATC | ATG | GAC | CAC | CAC | TCG | GCT | GCA | GAA | 1529 |
|---|---|---|---|---|---|---|---|---|---|---|---|---|---|---|---|---|
| Phe | Gln | Lys | Gln | Asn | Val | Thr | Ile | Met | Asp | His | His | Ser | Ala | Ala | Glu |  |
|  |  |  |  | 430 |  |  |  |  | 435 |  |  |  |  | 440 |  |  |

| TCC | TTC | ATG | AAG | TAC | ATG | CAG | AAT | GAA | TAC | CGG | TCC | CGT | GGG | GGC | TGC | 1577 |
|---|---|---|---|---|---|---|---|---|---|---|---|---|---|---|---|---|
| Ser | Phe | Met | Lys | Tyr | Met | Gln | Asn | Glu | Tyr | Arg | Ser | Arg | Gly | Gly | Cys |  |
|  |  |  | 445 |  |  |  |  | 450 |  |  |  |  | 455 |  |  |  |

| CCG | GCA | GAC | TGG | ATT | TGG | CTG | GTC | CCT | CCC | ATG | TCT | GGG | AGC | ATC | ACC | 1625 |
|---|---|---|---|---|---|---|---|---|---|---|---|---|---|---|---|---|
| Pro | Ala | Asp | Trp | Ile | Trp | Leu | Val | Pro | Pro | Met | Ser | Gly | Ser | Ile | Thr |  |
|  |  | 460 |  |  |  |  | 465 |  |  |  |  | 470 |  |  |  |  |

| CCC | GTG | TTT | CAC | CAG | GAG | ATG | CTG | AAC | TAC | GTC | CTG | TCC | CCT | TTC | TAC | 1673 |
|---|---|---|---|---|---|---|---|---|---|---|---|---|---|---|---|---|
| Pro | Val | Phe | His | Gln | Glu | Met | Leu | Asn | Tyr | Val | Leu | Ser | Pro | Phe | Tyr |  |
|  | 475 |  |  |  |  | 480 |  |  |  |  | 485 |  |  |  |  |  |

| TAC | TAT | CAG | GTA | GAG | GCC | TGG | AAA | ACC | CAT | GTC | TGG | CAG | GAC | GAG | AAG | 1721 |
|---|---|---|---|---|---|---|---|---|---|---|---|---|---|---|---|---|

| | | | | | | | | | | | | | | | | |
|---|---|---|---|---|---|---|---|---|---|---|---|---|---|---|---|---|
| Tyr | Tyr | Gln | Val | Glu | Ala | Trp | Lys | Thr | His | Val | Trp | Gln | Asp | Glu | Lys | |
| 490 | | | | 495 | | | | | | 500 | | | | | 505 | |
| CGG | AGA | CCC | AAG | AGA | AGA | GAG | ATT | CCA | TTG | AAA | GTC | TTG | GTC | AAA | GCT | 1769 |
| Arg | Arg | Pro | Lys | Arg | Arg | Glu | Ile | Pro | Leu | Lys | Val | Leu | Val | Lys | Ala | |
| | | | | 510 | | | | | 515 | | | | | 520 | | |
| GTG | CTC | TTT | GCC | TGT | ATG | CTG | ATG | CGC | AAG | ACA | ATG | GCG | TCC | CGA | GTC | 1817 |
| Val | Leu | Phe | Ala | Cys | Met | Leu | Met | Arg | Lys | Thr | Met | Ala | Ser | Arg | Val | |
| | | | | 525 | | | | | 530 | | | | | 535 | | |
| AGA | GTC | ACC | ATC | CTC | TTT | GCG | ACA | GAG | ACA | GGA | AAA | TCA | GAG | GCG | CTG | 1865 |
| Arg | Val | Thr | Ile | Leu | Phe | Ala | Thr | Glu | Thr | Gly | Lys | Ser | Glu | Ala | Leu | |
| | | | 540 | | | | | 545 | | | | | 550 | | | |
| GCC | TGG | GAC | CTG | GGG | GCC | TTA | TTC | AGC | TGT | GCC | TTC | AAC | CCC | AAG | GTT | 1913 |
| Ala | Trp | Asp | Leu | Gly | Ala | Leu | Phe | Ser | Cys | Ala | Phe | Asn | Pro | Lys | Val | |
| | | 555 | | | | | 560 | | | | | 565 | | | | |
| GTC | TGC | ATG | GAT | AAG | TAC | AGG | CTG | AGC | TGC | CTG | GAG | GAG | GAA | CGG | CTG | 1961 |
| Val | Cys | Met | Asp | Lys | Tyr | Arg | Leu | Ser | Cys | Leu | Glu | Glu | Glu | Arg | Leu | |
| 570 | | | | | 575 | | | | | 580 | | | | | 585 | |
| CTG | TTG | GTG | GTG | ACC | AGT | ACG | TTT | GGC | AAT | GGA | GAC | TGC | CCT | GGC | AAT | 2009 |
| Leu | Leu | Val | Val | Thr | Ser | Thr | Phe | Gly | Asn | Gly | Asp | Cys | Pro | Gly | Asn | |
| | | | | 590 | | | | | 595 | | | | | 600 | | |
| GGA | GAG | AAA | CTG | AAG | AAA | TCG | CTC | TTC | ATG | CTG | AAA | GAG | CTC | AAC | AAC | 2057 |
| Gly | Glu | Lys | Leu | Lys | Lys | Ser | Leu | Phe | Met | Leu | Lys | Glu | Leu | Asn | Asn | |
| | | | 605 | | | | | 610 | | | | | 615 | | | |
| AAA | TTC | AGG | TAC | GCT | GTG | TTT | GGC | CTC | GGC | TCC | AGC | ATG | TAC | CCT | CGG | 2105 |
| Lys | Phe | Arg | Tyr | Ala | Val | Phe | Gly | Leu | Gly | Ser | Ser | Met | Tyr | Pro | Arg | |
| | | 620 | | | | | 625 | | | | | 630 | | | | |
| TTC | TGC | GCC | TTT | GCT | CAT | GAC | ATT | GAT | CAG | AAG | CTG | TCC | CAC | CTG | GGG | 2153 |
| Phe | Cys | Ala | Phe | Ala | His | Asp | Ile | Asp | Gln | Lys | Leu | Ser | His | Leu | Gly | |
| | 635 | | | | | 640 | | | | | 645 | | | | | |
| GCC | TCT | CAG | CTC | ACC | CCG | ATG | GGA | GAA | GGG | GAT | GAG | CTC | AGT | GGG | CAG | 2201 |
| Ala | Ser | Gln | Leu | Thr | Pro | Met | Gly | Glu | Gly | Asp | Glu | Leu | Ser | Gly | Gln | |
| 650 | | | | | 655 | | | | | 660 | | | | | 665 | |
| GAG | GAC | GCC | TTC | CGC | AGC | TGG | GCC | GTG | CAA | ACC | TTC | AAG | GCA | GCC | TGT | 2249 |
| Glu | Asp | Ala | Phe | Arg | Ser | Trp | Ala | Val | Gln | Thr | Phe | Lys | Ala | Ala | Cys | |
| | | | | 670 | | | | | 675 | | | | | 680 | | |
| GAG | ACG | TTT | GAT | GTC | CGA | GGC | AAA | CAG | CAC | ATT | CAG | ATC | CCC | AAG | CTC | 2297 |
| Glu | Thr | Phe | Asp | Val | Arg | Gly | Lys | Gln | His | Ile | Gln | Ile | Pro | Lys | Leu | |
| | | | 685 | | | | | 690 | | | | | 695 | | | |
| TAC | ACC | TCC | AAT | GTG | ACC | TGG | GAC | CCG | CAC | CAC | TAC | AGG | CTC | GTG | CAG | 2345 |
| Tyr | Thr | Ser | Asn | Val | Thr | Trp | Asp | Pro | His | His | Tyr | Arg | Leu | Val | Gln | |
| | | 700 | | | | | 705 | | | | | 710 | | | | |
| GAC | TCA | CAG | CCT | TTG | GAC | CTC | AGC | AAA | GCC | CTC | AGC | AGC | ATG | CAT | GCC | 2393 |
| Asp | Ser | Gln | Pro | Leu | Asp | Leu | Ser | Lys | Ala | Leu | Ser | Ser | Met | His | Ala | |
| | 715 | | | | | 720 | | | | | 725 | | | | | |
| AAG | AAC | GTG | TTC | ACC | ATG | AGG | CTC | AAA | TCT | CGG | CAG | AAT | CTA | CAA | AGT | 2441 |
| Lys | Asn | Val | Phe | Thr | Met | Arg | Leu | Lys | Ser | Arg | Gln | Asn | Leu | Gln | Ser | |
| 730 | | | | | 735 | | | | | 740 | | | | | 745 | |
| CCG | ACA | TCC | AGC | CGT | GCC | ACC | ATC | CTG | GTG | GAA | CTC | TCC | TGT | GAG | GAT | 2489 |
| Pro | Thr | Ser | Ser | Arg | Ala | Thr | Ile | Leu | Val | Glu | Leu | Ser | Cys | Glu | Asp | |
| | | | | 750 | | | | | 755 | | | | | 760 | | |
| GGC | CAA | GGC | CTG | AAC | TAC | CTG | CCG | GGG | GAG | CAC | CTT | GGG | GTT | TGC | CCA | 2537 |
| Gly | Gln | Gly | Leu | Asn | Tyr | Leu | Pro | Gly | Glu | His | Leu | Gly | Val | Cys | Pro | |
| | | | 765 | | | | | 770 | | | | | 775 | | | |
| GGC | AAC | CAG | CCG | GCC | CTG | GTC | CAA | GGC | ATC | CTG | GAG | CGA | GTG | GTG | GAT | 2585 |
| Gly | Asn | Gln | Pro | Ala | Leu | Val | Gln | Gly | Ile | Leu | Glu | Arg | Val | Val | Asp | |
| | | 780 | | | | | 785 | | | | | 790 | | | | |
| GGC | CCC | ACA | CCC | CAC | CAG | ACA | GTG | CGC | CTG | GAG | GAC | CTG | GAT | GAG | AGT | 2633 |
| Gly | Pro | Thr | Pro | His | Gln | Thr | Val | Arg | Leu | Glu | Asp | Leu | Asp | Glu | Ser | |
| | 795 | | | | | 800 | | | | | 805 | | | | | |
| GGC | AGC | TAC | TGG | GTC | AGT | GAC | AAG | AGG | CTG | CCC | CCC | TGC | TCA | CTC | AGC | 2681 |

|  |  |
|---|---|
| Gly Ser Tyr Trp Val Ser Asp Lys Arg Leu Pro Pro Cys Ser Leu Ser<br>810                        815                    820                      825 |  |
| CAG GCC CTC ACC TAC TCC CCG GAC ATC ACC ACA CCC CCA ACC CAG CTG<br>Gln Ala Leu Thr Tyr Ser Pro Asp Ile Thr Thr Pro Pro Thr Gln Leu<br>                830                      835                        840 | 2729 |
| CTG CTC CAA AAG CTG GCC CAG GTG GCC ACA GAA GAG CCT GAG AGA CAG<br>Leu Leu Gln Lys Leu Ala Gln Val Ala Thr Glu Glu Pro Glu Arg Gln<br>          845                      850                      855 | 2777 |
| AGG CTG GAG GCC CTG TGC CAG CCC TCA GAG TAC AGC AAG TGG AAG TTC<br>Arg Leu Glu Ala Leu Cys Gln Pro Ser Glu Tyr Ser Lys Trp Lys Phe<br>              860                      865                    870 | 2825 |
| ACC AAC AGC CCC ACA TTC CTG GAG GTG CTA GAG GAG TTC CCG TCC CTG<br>Thr Asn Ser Pro Thr Phe Leu Glu Val Leu Glu Glu Phe Pro Ser Leu<br>875                        880                      885 | 2873 |
| CGG GTG TCT GCT GGC TTC CTG CTT TCC CAG CTC CCC ATT CTG AAG CCC<br>Arg Val Ser Ala Gly Phe Leu Leu Ser Gln Leu Pro Ile Leu Lys Pro<br>890                      895                    900                905 | 2921 |
| AGG TTC TAC TCC ATC AGC TCC TCC CGG GAT CAC ACG CCC ACG GAG ATC<br>Arg Phe Tyr Ser Ile Ser Ser Ser Arg Asp His Thr Pro Thr Glu Ile<br>              910                      915                    920 | 2969 |
| CAC CTG ACT GTG GCC GTG GTC ACC TAC CAC ACC GGA GAT GGC CAG GGT<br>His Leu Thr Val Ala Val Val Thr Tyr His Thr Gly Asp Gly Gln Gly<br>                925                      930                    935 | 3017 |
| CCC CTG CAC CAC GGT GTC TGC AGC ACA TGG CTC AAC AGC CTG AAG CCC<br>Pro Leu His His Gly Val Cys Ser Thr Trp Leu Asn Ser Leu Lys Pro<br>          940                      945                    950 | 3065 |
| CAA GAC CCA GTG CCC TGC TTT GTG CGG AAT GCC AGC GCC TTC CAC CTC<br>Gln Asp Pro Val Pro Cys Phe Val Arg Asn Ala Ser Ala Phe His Leu<br>     955                      960                    965 | 3113 |
| CCC GAG GAT CCC TCC CAT CCT TGC ATC CTC ATC GGG CCT GGC ACA GGC<br>Pro Glu Asp Pro Ser His Pro Cys Ile Leu Ile Gly Pro Gly Thr Gly<br>970                        975                    980                985 | 3161 |
| ATC GTG CCC TTC CGC AGT TTC TGG CAG CAA CGG CTC CAT GAC TCC CAG<br>Ile Val Pro Phe Arg Ser Phe Trp Gln Gln Arg Leu His Asp Ser Gln<br>              990                      995                1000 | 3209 |
| CAC AAG GGA GTG CGG GGA GGC CGC ATG ACC TTG GTG TTT GGG TGC CGC<br>His Lys Gly Val Arg Gly Gly Arg Met Thr Leu Val Phe Gly Cys Arg<br>              1005                    1010                1015 | 3257 |
| CGC CCA GAT GAG GAC CAC ATC TAC CAG GAG GAG ATG CTG GAG ATG GCC<br>Arg Pro Asp Glu Asp His Ile Tyr Gln Glu Glu Met Leu Glu Met Ala<br>         1020                    1025                    1030 | 3305 |
| CAG AAG GGG GTG CTG CAT GCG GTG CAC ACA GCC TAT TCC CGC CTG CCT<br>Gln Lys Gly Val Leu His Ala Val His Thr Ala Tyr Ser Arg Leu Pro<br>              1035                    1040                1045 | 3353 |
| GGC AAG CCC AAG GTC TAT GTT CAG GAC ATC CTG CGG CAG CAG CTG GCC<br>Gly Lys Pro Lys Val Tyr Val Gln Asp Ile Leu Arg Gln Gln Leu Ala<br>1050                      1055                    1060                1065 | 3401 |
| AGC GAG GTG CTC CGT GTG CTC CAC AAG GAG CCA GGC CAC CTC TAT GTT<br>Ser Glu Val Leu Arg Val Leu His Lys Glu Pro Gly His Leu Tyr Val<br>         1070                    1075                    1080 | 3449 |
| TGC GGG GAT GTG CGC ATG GCC CGG GAC GTG GCC CAC ACC CTG AAG CAG<br>Cys Gly Asp Val Arg Met Ala Arg Asp Val Ala His Thr Leu Lys Gln<br>              1085                    1090                    1095 | 3497 |
| CTG GTG GCT GCC AAG CTG AAA TTG AAT GAG GAG CAG GTC GAG GAC TAT<br>Leu Val Ala Ala Lys Leu Lys Leu Asn Glu Glu Gln Val Glu Asp Tyr<br>         1100                    1105                    1110 | 3545 |
| TTC TTT CAG CTC AAG AGC CAG AAG CGC TAT CAC GAA GAT ATC TTC GGT<br>Phe Phe Gln Leu Lys Ser Gln Lys Arg Tyr His Glu Asp Ile Phe Gly<br>         1115                    1120                    1125 | 3593 |
| GCT GTA TTT CCT TAC GAG GCG AAG AAG GAC AGG GTG GCG GTG CAG CCC | 3641 |

| Ala | Val | Phe | Pro | Tyr | Glu | Ala | Lys | Lys | Asp | Arg | Val | Ala | Val | Gln | Pro |
|---|---|---|---|---|---|---|---|---|---|---|---|---|---|---|---|
| 1130 | | | | | 1135 | | | | | 1140 | | | | | 1145 |

| AGC | AGC | CTG | GAG | ATG | TCA | GCG | CTC | TGAGGGCCTA | CAGGAGGGGT | TAAAGCTGCC | 3695 |
|---|---|---|---|---|---|---|---|---|---|---|---|
| Ser | Ser | Leu | Glu | Met | Ser | Ala | Leu | | | | |
| | | | | 1150 | | | | | | | |

| GGCACAGAAC | TTAAGGATGG | AGCCAGCTCT | GCATTATCTG | AGGTCACAGG | GCCTGGGGAG | 3755 |
| ATGGAGGAAA | GTGATATCCC | CCAGCCTCAA | GTCTTATTTC | CTCAACGTTG | CTCCCCATCA | 3815 |
| AGCCCTTTAC | TTGACCTCCT | AACAAGTAGC | ACCCTGGATT | GATCGGAGCC | TCCTCTCTCA | 3875 |
| AACTGGGGCC | TCCCTGGTCC | CTTGGAGACA | AAATCTTAAA | TGCCAGGCCT | GGCGAGTGGG | 3935 |
| TGAAAGATGG | AACTTGCTGC | TGAGTGCACC | ACTTCAAGTG | ACCACCAGGA | GGTGCTATCG | 3995 |
| CACCACTGTG | TATTTAACTG | CCTTGTGTAC | AGTTATTTAT | GCCTCTGTAT | TTAAAAAACT | 4055 |
| AACACCCAGT | CTGTTCCCCA | TGGCCACTTG | GGTCTTCCCT | GTATGATTCC | TTGATGGAGA | 4115 |
| TATTTACATG | AATTGCATTT | TACTTTAATC | | | | 4145 |

(2) INFORMATION FOR SEQ ID NO:2:

(i) SEQUENCE CHARACTERISTICS:
        (A) LENGTH: 1153 amino acids
        (B) TYPE: amino acid
        (D) TOPOLOGY: linear (ii) MOLECULE TYPE: protein (xi) SEQUENCE DESCRIPTION: SEQ ID NO:2:

| Met | Ala | Cys | Pro | Trp | Lys | Phe | Leu | Phe | Lys | Thr | Lys | Phe | His | Gln | Tyr |
|---|---|---|---|---|---|---|---|---|---|---|---|---|---|---|---|
| 1 | | | | 5 | | | | | 10 | | | | | 15 | |

| Ala | Met | Asn | Gly | Glu | Lys | Asp | Ile | Asn | Asn | Asn | Val | Glu | Lys | Ala | Pro |
|---|---|---|---|---|---|---|---|---|---|---|---|---|---|---|---|
| | | | 20 | | | | | 25 | | | | | 30 | | |

| Cys | Ala | Thr | Ser | Ser | Pro | Val | Thr | Gln | Asp | Asp | Leu | Gln | Tyr | His | Asn |
|---|---|---|---|---|---|---|---|---|---|---|---|---|---|---|---|
| | | | 35 | | | | 40 | | | | | 45 | | | |

| Leu | Ser | Lys | Gln | Gln | Asn | Glu | Ser | Pro | Gln | Pro | Leu | Val | Glu | Thr | Gly |
|---|---|---|---|---|---|---|---|---|---|---|---|---|---|---|---|
| | 50 | | | | | 55 | | | | | 60 | | | | |

| Lys | Lys | Ser | Pro | Glu | Ser | Leu | Val | Lys | Leu | Asp | Ala | Thr | Pro | Leu | Ser |
|---|---|---|---|---|---|---|---|---|---|---|---|---|---|---|---|
| 65 | | | | | 70 | | | | | 75 | | | | | 80 |

| Ser | Pro | Arg | His | Val | Arg | Ile | Lys | Asn | Trp | Gly | Ser | Gly | Met | Thr | Phe |
|---|---|---|---|---|---|---|---|---|---|---|---|---|---|---|---|
| | | | | 85 | | | | | 90 | | | | | 95 | |

| Gln | Asp | Thr | Leu | His | His | Lys | Ala | Lys | Gly | Ile | Leu | Thr | Cys | Arg | Ser |
|---|---|---|---|---|---|---|---|---|---|---|---|---|---|---|---|
| | | | 100 | | | | | 105 | | | | | 110 | | |

| Lys | Ser | Cys | Leu | Gly | Ser | Ile | Met | Thr | Pro | Lys | Ser | Leu | Thr | Arg | Gly |
|---|---|---|---|---|---|---|---|---|---|---|---|---|---|---|---|
| | | 115 | | | | | 120 | | | | | 125 | | | |

| Pro | Arg | Asp | Lys | Pro | Thr | Pro | Pro | Asp | Glu | Leu | Leu | Pro | Gln | Ala | Ile |
|---|---|---|---|---|---|---|---|---|---|---|---|---|---|---|---|
| | 130 | | | | | 135 | | | | | 140 | | | | |

| Glu | Phe | Val | Asn | Gln | Tyr | Tyr | Gly | Ser | Phe | Lys | Glu | Ala | Lys | Ile | Glu |
|---|---|---|---|---|---|---|---|---|---|---|---|---|---|---|---|
| 145 | | | | | 150 | | | | | 155 | | | | | 160 |

| Glu | His | Leu | Ala | Arg | Val | Glu | Ala | Val | Thr | Lys | Glu | Ile | Glu | Thr | Thr |
|---|---|---|---|---|---|---|---|---|---|---|---|---|---|---|---|
| | | | | 165 | | | | | 170 | | | | | 175 | |

| Gly | Thr | Tyr | Gln | Leu | Thr | Gly | Asp | Glu | Leu | Ile | Phe | Ala | Thr | Lys | Gln |
|---|---|---|---|---|---|---|---|---|---|---|---|---|---|---|---|
| | | | 180 | | | | | 185 | | | | | 190 | | |

| Ala | Trp | Arg | Asn | Ala | Pro | Arg | Cys | Ile | Gly | Arg | Ile | Gln | Trp | Ser | Asn |
|---|---|---|---|---|---|---|---|---|---|---|---|---|---|---|---|
| | | 195 | | | | | 200 | | | | | 205 | | | |

| Leu | Gln | Val | Phe | Asp | Ala | Arg | Ser | Cys | Ser | Thr | Ala | Arg | Glu | Met | Phe |
|---|---|---|---|---|---|---|---|---|---|---|---|---|---|---|---|
| | 210 | | | | | 215 | | | | | 220 | | | | |

| Glu | His | Ile | Cys | Arg | His | Val | Arg | Tyr | Ser | Thr | Asn | Asn | Gly | Asn | Ile |
|---|---|---|---|---|---|---|---|---|---|---|---|---|---|---|---|
| 225 | | | | | 230 | | | | | 235 | | | | | 240 |

-continued

| | | | | | | | | | | | | | | |
|---|---|---|---|---|---|---|---|---|---|---|---|---|---|---|
|Arg|Ser|Ala|Ile<br>245|Thr|Val|Phe|Pro|Gln|Arg<br>250|Ser|Asp|Gly|Lys|His<br>255|Asp|
|Phe|Arg|Val|Trp<br>260|Asn|Ala|Gln|Leu|Ile<br>265|Arg|Tyr|Ala|Gly|Tyr<br>270|Gln|Met|
|Pro|Asp|Gly|Ser<br>275|Ile|Arg|Gly|Asp<br>280|Pro|Ala|Asn|Val|Glu<br>285|Phe|Thr|Gln|
|Leu|Cys<br>290|Ile|Asp|Leu|Gly|Trp<br>295|Lys|Pro|Lys|Tyr|Gly<br>300|Arg|Phe|Asp|Val|
|Val<br>305|Pro|Leu|Val|Leu|Gln<br>310|Ala|Asn|Gly|Arg|Asp<br>315|Pro|Glu|Leu|Phe|Glu<br>320|
|Ile|Pro|Pro|Asp|Leu<br>325|Val|Leu|Glu|Val|Ala|Met|Glu<br>330|His|Pro|Lys<br>335|Tyr|
|Glu|Trp|Phe|Arg<br>340|Glu|Leu|Glu|Leu|Lys<br>345|Trp|Tyr|Ala|Leu|Pro<br>350|Ala|Val|
|Ala|Asn|Met<br>355|Leu|Leu|Glu|Val|Gly<br>360|Gly|Leu|Glu|Phe|Pro<br>365|Gly|Cys|Pro|
|Phe|Asn<br>370|Gly|Trp|Tyr|Met|Gly<br>375|Thr|Glu|Ile|Gly|Val<br>380|Arg|Asp|Phe|Cys|
|Asp<br>385|Val|Gln|Arg|Tyr|Asn<br>390|Ile|Leu|Glu|Glu|Val<br>395|Gly|Arg|Arg|Met|Gly<br>400|
|Leu|Glu|Thr|His|Lys<br>405|Leu|Ala|Ser|Leu|Trp<br>410|Lys|Asp|Gln|Ala|Val<br>415|Val|
|Glu|Ile|Asn|Ile<br>420|Ala|Val|Ile|His|Ser<br>425|Phe|Gln|Lys|Gln|Asn<br>430|Val|Thr|
|Ile|Met|Asp<br>435|His|His|Ser|Ala|Ala<br>440|Glu|Ser|Phe|Met|Lys<br>445|Tyr|Met|Gln|
|Asn|Glu<br>450|Tyr|Arg|Ser|Arg|Gly<br>455|Gly|Cys|Pro|Ala|Asp<br>460|Trp|Ile|Trp|Leu|
|Val<br>465|Pro|Pro|Met|Ser|Gly<br>470|Ser|Ile|Thr|Pro|Val<br>475|Phe|His|Gln|Glu|Met<br>480|
|Leu|Asn|Tyr|Val|Leu<br>485|Ser|Pro|Phe|Tyr|Tyr<br>490|Tyr|Gln|Val|Glu|Ala<br>495|Trp|
|Lys|Thr|His|Val<br>500|Trp|Gln|Asp|Glu|Lys<br>505|Arg|Arg|Pro|Lys|Arg<br>510|Arg|Glu|
|Ile|Pro|Leu|Lys<br>515|Val|Leu|Val|Lys<br>520|Ala|Val|Leu|Phe|Ala<br>525|Cys|Met|Leu|
|Met|Arg|Lys<br>530|Thr|Met|Ala|Ser|Arg<br>535|Val|Arg|Val|Thr<br>540|Ile|Leu|Phe|Ala|
|Thr<br>545|Glu|Thr|Gly|Lys|Ser<br>550|Glu|Ala|Leu|Ala|Trp<br>555|Asp|Leu|Gly|Ala|Leu<br>560|
|Phe|Ser|Cys|Ala|Phe<br>565|Asn|Pro|Lys|Val|Val<br>570|Cys|Met|Asp|Lys|Tyr<br>575|Arg|
|Leu|Ser|Cys|Leu<br>580|Glu|Glu|Arg|Leu|Leu<br>585|Leu|Val|Val|Thr|Ser<br>590|Thr|
|Phe|Gly|Asn<br>595|Gly|Asp|Cys|Pro|Gly<br>600|Asn|Gly|Glu|Lys|Leu<br>605|Lys|Lys|Ser|
|Leu|Phe<br>610|Met|Leu|Lys|Glu|Leu<br>615|Asn|Asn|Lys|Phe|Arg<br>620|Tyr|Ala|Val|Phe|
|Gly<br>625|Leu|Gly|Ser|Ser|Met<br>630|Tyr|Pro|Arg|Phe|Cys<br>635|Ala|Phe|Ala|His|Asp<br>640|
|Ile|Asp|Gln|Lys|Leu<br>645|Ser|His|Leu|Gly|Ala<br>650|Ser|Gln|Leu|Thr|Pro<br>655|Met|
|Gly|Glu|Gly|Asp<br>660|Glu|Leu|Ser|Gly|Gln<br>665|Glu|Asp|Ala|Phe|Arg<br>670|Ser|Trp|

| | | | | | | | | | | | | | |
|---|---|---|---|---|---|---|---|---|---|---|---|---|---|
| Ala | Val | Gln 675 | Thr | Phe | Lys | Ala 680 | Ala | Cys | Glu | Thr | Phe 685 | Asp | Val | Arg | Gly |
| Lys | Gln 690 | His | Ile | Gln | Ile 695 | Pro | Lys | Leu | Tyr | Thr 700 | Ser | Asn | Val | Thr | Trp |
| Asp 705 | Pro | His | His | Tyr 710 | Arg | Leu | Val | Gln | Asp 715 | Ser | Gln | Pro | Leu | Asp 720 | Leu |
| Ser | Lys | Ala | Leu | Ser 725 | Ser | Met | His | Ala | Lys 730 | Asn | Val | Phe | Thr 735 | Met | Arg |
| Leu | Lys | Ser | Arg 740 | Gln | Asn | Leu | Gln | Ser 745 | Pro | Thr | Ser | Ser | Arg 750 | Ala | Thr |
| Ile | Leu | Val 755 | Glu | Leu | Ser | Cys | Glu 760 | Asp | Gly | Gln | Gly | Leu 765 | Asn | Tyr | Leu |
| Pro | Gly 770 | Glu | His | Leu | Gly | Val 775 | Cys | Pro | Gly | Asn | Gln 780 | Pro | Ala | Leu | Val |
| Gln 785 | Gly | Ile | Leu | Glu | Arg 790 | Val | Val | Asp | Gly | Pro 795 | Thr | Pro | His | Gln | Thr 800 |
| Val | Arg | Leu | Glu | Asp 805 | Leu | Asp | Glu | Ser | Gly 810 | Ser | Tyr | Trp | Val | Ser 815 | Asp |
| Lys | Arg | Leu | Pro 820 | Pro | Cys | Ser | Leu | Ser 825 | Gln | Ala | Leu | Thr | Tyr 830 | Ser | Pro |
| Asp | Ile | Thr 835 | Thr | Pro | Pro | Thr | Gln 840 | Leu | Leu | Leu | Gln | Lys 845 | Leu | Ala | Gln |
| Val | Ala 850 | Thr | Glu | Glu | Pro | Glu 855 | Arg | Gln | Arg | Leu | Glu 860 | Ala | Leu | Cys | Gln |
| Pro 865 | Ser | Glu | Tyr | Ser | Lys 870 | Trp | Lys | Phe | Thr | Asn 875 | Ser | Pro | Thr | Phe | Leu 880 |
| Glu | Val | Leu | Glu | Glu 885 | Phe | Pro | Ser | Leu | Arg 890 | Val | Ser | Ala | Gly 895 | Phe | Leu |
| Leu | Ser | Gln | Leu 900 | Pro | Ile | Leu | Lys | Pro 905 | Arg | Phe | Tyr | Ser | Ile 910 | Ser | Ser |
| Ser | Arg | Asp 915 | His | Thr | Pro | Thr | Glu 920 | Ile | His | Leu | Thr | Val 925 | Ala | Val | Val |
| Thr | Tyr 930 | His | Thr | Gly | Asp | Gly 935 | Gln | Gly | Pro | Leu | His 940 | His | Gly | Val | Cys |
| Ser 945 | Thr | Trp | Leu | Asn | Ser 950 | Leu | Lys | Pro | Gln | Asp 955 | Pro | Val | Pro | Cys | Phe 960 |
| Val | Arg | Asn | Ala | Ser 965 | Ala | Phe | His | Leu | Pro 970 | Glu | Asp | Pro | Ser | His 975 | Pro |
| Cys | Ile | Leu | Ile 980 | Gly | Pro | Gly | Thr | Gly 985 | Ile | Val | Pro | Phe | Arg 990 | Ser | Phe |
| Trp | Gln | Gln 995 | Arg | Leu | His | Asp | Ser 1000 | Gln | His | Lys | Gly | Val 1005 | Arg | Gly | Gly |
| Arg | Met 1010 | Thr | Leu | Val | Phe | Gly 1015 | Cys | Arg | Arg | Pro | Asp 1020 | Glu | Asp | His | Ile |
| Tyr 1025 | Gln | Glu | Glu | Met | Leu 1030 | Glu | Met | Ala | Gln | Lys 1035 | Gly | Val | Leu | His | Ala 1040 |
| Val | His | Thr | Ala | Tyr 1045 | Ser | Arg | Leu | Pro | Gly 1050 | Lys | Pro | Lys | Val 1055 | Tyr | Val |
| Gln | Asp | Ile | Leu 1060 | Arg | Gln | Gln | Leu | Ala 1065 | Ser | Glu | Val | Leu | Arg 1070 | Val | Leu |
| His | Lys | Glu 1075 | Pro | Gly | His | Leu | Tyr 1080 | Val | Cys | Gly | Asp | Val 1085 | Arg | Met | Ala |
| Arg | Asp | Val | Ala | His | Thr | Leu | Lys | Gln | Leu | Val | Ala | Ala | Lys | Leu | Lys |

|      | 1090 |     |     |     | 1095 |     |     |     | 1100 |     |     |     |      |
|------|------|-----|-----|-----|------|-----|-----|-----|------|-----|-----|-----|------|
| Leu  | Asn  | Glu | Glu | Gln | Val  | Glu | Asp | Tyr | Phe  | Phe | Gln | Leu | Lys  | Ser | Gln |
| 1105 |      |     |     |     | 1110 |     |     |     | 1115 |     |     |     | 1120 |

| Lys | Arg | Tyr | His | Glu | Asp | Ile | Phe | Gly | Ala | Val | Phe | Pro | Tyr | Glu | Ala |
|     |     |     |     | 1125|     |     |     |     | 1130|     |     |     |     | 1135|     |

| Lys | Lys | Asp | Arg | Val | Ala | Val | Gln | Pro | Ser | Ser | Leu | Glu | Met | Ser | Ala |
|     |     |     | 1140|     |     |     |     | 1145|     |     |     |     | 1150|     |     |

Leu

INDUCIBLE NITRIC OXIDE SYNTHASE GENE FOR TREATMENT OF DISEASE

The invention described herein was made in the course of work supported in part by Public Health Service, Grant Nos. GM44100 and GM37753 from the United States National Institutes of Health, General Medical Sciences. The United States Government has certain rights in this invention.

TABLE OF CONTENTS

1. Introduction
2. Background of the Invention
3. Summary of the Invention
   3.1. Definitions
4. Brief Description of the FIGS.
5. Detailed Description of the Invention
   5.1. Isolation and Characterization of a cDNA Clone Coding For a Human Inducible Nitric Oxide Synthase
   5.2. Gene Therapy Applications Utilizing Human iNOS
      5.2.1. Treatment of Vascular Occlusive Disease Associated With Diabetes
      5.2.2. Biologic Therapy By Promotion of Antitumor Effects
      5.2.3. Biologic Therapy For Treating Microbial Infections
6. Example: Inducing Human Hepatocyte Inducible Nitric Oxide Synthase
7. Example: Identifying and Isolating Human Hepatocyte Nitric Oxide Synthase mRNA
8. Example: Constructing a Human Hepatocyte Inducible Nitric Oxide Synthase cDNA Library
9. Example: Screening the cDNA Library For Human Hepatocyte Nitric Oxide Synthase cDNA Clones
10. Example: cDNA Sequencing
11. Example: Expressing Human Hepatocyte Inducible Nitric Oxide Synthase
12. Example: Purifying the Human Hepatocyte Inducible Nitric Oxide Synthase Protein
13. Example: Treatment of Vascular Occlusive Disease Associated
    13.1. Materials and Methods
       13.1.1. In Vitro Transfection of Target Cells With a Human iNOS cDNA
       13.1.2. In Vivo Endothelial Cell Manipulation
14. Example: iNOS Directed Cancer Therapy
15. Example: iNOS Directed Antimicrobial Treatment
16. Deposit of Microorganisms

1. INTRODUCTION

This invention relates to a human tissue inducible nitric oxide synthase cDNA clone capable of expressing a human inducible nitric oxide synthase protein, and a process suitable for cloning a cDNA encoding amino acid sequences for the human inducible nitric oxide synthase. More specifically, this invention relates to a human hepatocyte inducible nitric oxide synthase cDNA clone and to a process for cloning and expression of the human hepatocyte inducible nitric oxide synthase cDNA to provide a source of the human hepatocyte inducible nitric oxide synthase enzyme.

FIGS. 1A–G show the 4,145 nucleotide bases for the sense strand of cDNA for human hepatocyte inducible nitric oxide synthase and sets forth the base codes as triplets (codon) for the coding parts of the nucleotide sequence. FIGS. 1A–G show the amino acid sequence for the cDNA clone for human hepatocyte inducible nitric oxide synthase encoding amino acids 1 through 1153 of the human hepatocyte inducible nitric oxide synthase enzyme.

The invention further relates to the use of a nucleic acid sequence encoding inducible NOS (iNOS) or a biologically active iNOS protein fragment in gene therapy applications of mammalian host diseases or disorders. Such maladies include, but are not limited to, treatment of vascular occlusive disease, as well as cancer, and microbial infection.

2. BACKGROUND OF THE INVENTION

It is known by those skilled in the art that nitric oxide (NO) is a biologic mediator derived from the amino acid L-arginine. A family of enzymes, known as nitric oxide synthase (NOS), act upon L-arginine to oxidize one of the guanidino nitrogens to nitric oxide while citrulline is formed from the remainder of the L-arginine molecule. Nitric oxide is a very short-lived free radical and is rapidly oxidized to nitrite ($NO_2^-$) and nitrate ($NO_3^-$) which are measured as the stable inactive end products of nitric oxide formation.

It is well known by those skilled in the art that multiple isoforms of the nitric oxide synthase enzyme exist and that they are generally classified into two broad categories: (1) constitutive and (2) inducible. These classes of NOS enzymes vary considerably in size, amino acid sequence, activity and regulation. For example, cells such as neurons and vascular endothelial cells contain constitutive NOS isoforms while macrophages and vascular smooth muscle cells express an inducible NOS.

It is generally well known that the small amounts of nitric oxide generated by a constitutive NOS appear to act as a messenger molecule by activating soluble guanylate cyclase and, thus, increasing intracellular guanosine, 3',5'-cyclic monophosphate (cGMP) and the induction of biological responses that are dependent on cGMP as a secondary messenger. For example, through this mechanism, endothelium derived nitric oxide induces relaxation of vascular smooth muscle and is identified as endothelium derived relaxing factor (EDRF) [Palmer, et al., 1987, Nature 327:524–526 and Ignarro, et al., 1987, Proc. Natl. Acad. Sci. USA 84: 9265–9269]. Another example includes, but is not limited by, neuronal nitric oxide which acts as a neurotansmitter by activating guanylate cyclase with important functions in the central nervous system and autonomic nervous system (Bredt, et al., 1989, Proc. Natl. Acad. Sci. USA 86:9030–9033 and Burnett, et al., 1992, Science 257: 401–409). It is generally known by those skilled in the art that the sustained production of nitric oxide by the inducible nitric oxide synthase has antimicrobial and antitumor functions. (see Granger, et al., 1989, J. Clin. Invest. 81: 1129–1196 and Hibbs, et al., 1987, Science 235: 479–476, respectively). It is also known by those skilled in the art that when vascular smooth muscle cells are stimulated to express a NOS enzyme by inflammatory cytokines, the large amounts of nitric oxide released contribute to the vasodilation and hypotension seen in sepsis (Busse and Mulsch, 1990, FEBS Letter 265: 133–136).

Thus, it will be appreciated that nitric oxide has normal physiologic intracellular and extracellular regulatory functions, and in some instances excessive production of nitric oxide can be detrimental. For example, stimulation of inducible nitric oxide synthesis in blood vessels by bacterial endotoxin, such as for example bacterial lipopolysaccharide (LPS), and cytokines that are elevated in sepsis results in excessive dilation of blood vessels and sustained hypotension commonly encountered with septic shock (Kilbourn, et al., 1990, Proc. Natl. Acad. Sci. USA 87: 3629–3632). It is known that overproduction of nitric oxide in lungs stimulated by immune complexes directly damages the lung (Mulligan, et al., 1992, J. Immunol. 148: 3086–3092). Induction of nitric oxide synthase in pancreatic islets impairs insulin secretion and contributes to the onset of juvenile diabetes (Corbett, et al., 1991, J. Biol. Chem. 266: 21351–21354). Production of nitric oxide in joints in immune-mediated arthritis contributes to joint destruction (McCartney, et al., 1993, J. Exp. Med. 178: 749–754).

It will be appreciated that there is a great need in the medical community for selective inhibition of the inducible form of NOS but not the constitutive types of NOS in humans because this would allow for a means of preventing, such as for example, the damage of pancreatic islets or joint destruction in arthritis without preventing the physiologic regulation of vasomotor tone or neurotransmission in the central nervous system.

In many situations nitric oxide even when produced in high amounts as seen with inducible nitric oxide synthase expression can be beneficial. For example, induced nitric oxide synthesis is important in preventing liver damage in endotoxemia (Billiar, et al., 1990, J. Leuk. Biol. 48: 565–569; Harbrecht et al, 1992, J. Leuk. Biol. 52:390–392).

Several references attempt to link nitric oxide to changes seen in vascular disease. For example, Bucala, et al. (1991, J. Clin. Inv. 87: 432–438) disclose that glycosylation products that accumulate in vessel walls during hyperglycemia may quench nitric oxide and reduce nitric oxide availability. Chin, et al. (1992, J. Clin. Inv. 89: 10–18) disclose that oxidized lipoproteins have a similar effect by inactivating nitric oxide. Chester, et al. (1990, Lancet 336: 897–900) disclose that nitric oxide synthesis is reduced in atherosclerotic epicardial arteries in humans. None of these references shed light on therapeutic avenues regarding iNOS-driven gene therapy.

Actions of nitric oxide important to vascular integrity and the prevention of the atherosclerotic lesion include vasodilation (Palmer, et al., 1987, Nature 327: 524–526; Ignarro, et al., 1987, Proc. Natl. Acad. Sci. USA 84: 9265–9269), inhibition of platelet adherence and aggregation (Radomski, et al., 1987, Br. J. Pharmacol. 92: 639–646), inhibition of vascular smooth muscle (Nunokawa, et al., 1992, Biochem. Biophys. Res. Com. 188:409–415) and fibroblast (Werner-Felmayer, et al., 1990, J. Exp. Med. 172: 1599–1607) cellular proliferation. Nitric oxide is normally produced by the vascular endothelium and, because of a very short half-life ($t_{1/2}$ in seconds), diffuses only to the adjacent smooth muscle where it causes relaxation via the activation of soluble guanylate cyclase (Moncada, et al., 1991, Pharmacol. Rev. 43: 109–142). Nitric oxide released toward the lumen assists in preventing platelet adherence. L-arginine serves as the substrate for nitric oxide formation, and the small amounts of nitric oxide derived from endothelial cells is produced in an ongoing fashion (Palmer, et al., 1987, Nature 327: 524–526; Ignarro, et al., 1987, Proc. Natl. Acad. Sci. USA 84: 9265–9269) by a cNOS, which is located primarily on microsomal and plasma membranes. Agonists such as acetylcholine and bradykinin increase cNOS by activity enhancing calcium/calmodulin binding to the enzyme. The cDNA coding for this enzyme has been cloned from human endothelial cells. (Janssens, et al., 1992, J. Biol. Chem. 267: 14519–14522; Marsden, et al., 1992, FEBS Letters 307: 287–293).

We recently demonstrated that nitric oxide biosynthesis is induced in isolated human hepatocytes after stimulation with interleukin-1, tumor necrosis factor-alpha, interferon-gamma and bacterial lipopolysaccharide (bacterial endotoxin) [Nussler, et al., April 1992, FASEB J. 6(5): A1834 and Nussler, et al., 1992, J. Exp. Med. 176: 261–264)]. Heretofore no human cell type was known to show increased production of nitrogen oxides typical of iNOS expression when treated with cytokines (Drapier, 1991, Res. Immunol., Vol. 142: 557). It is generally known by those skilled in the art that all attempts to induce nitric oxide synthase in human macrophages and related cells typical to those found in rodent macrophages have failed (Drapier, Res. Immunol. 142: 562, 589–590). In spite of this background material, there remains a very real and substantial need for a cDNA clone for human tissue inducible nitric oxide synthase and a process for the molecular cloning of the same.

Inducible NOS can be expressed in cell types such as murine macrophages under conditions of cytokine and endotoxin activation (Stuehr, et al., 1985, Proc. Natl. Acad. Sci. USA 82: 7738–7742; Hibbs, et al., 1987, Science 235: 473–476; Hibbs, et al., 1987, J. Immunol. 248: 550–565), rat hepatocytes (Curran, et al., 1989, J. Exp. Med. 170: 1769–1774; Billiar, et al., 1990, Biophys. Res. Corn. 168: 1034–1040), rat vascular smooth muscle cells (Busse, et al., 1990, FEBS Letter 275: 87–90; Nakayama, et al., 1992, Am. J. Respir. Cell. Mol. Biol. 7: 471–476), and capillary endothelial cells (Gross, et al., 1991, Biochem. Biophys. Res. Com. 179: 823–829). This enzyme, which is completely absent in resting cells, produces large amounts of nitric oxide continuously over many hours. A calmodulin is tightly bound to the iNOS molecule, keeping the enzyme in a fully activated state (Cho, et al., 1992, J. Exp. Med. 176: 599–604; Iida, et al., 1992, J. Biol. Chem. 267: 25385–25388). Release of large amounts of nitric oxide after iNOS induction in macrophages has cytostatic properties and is involved in the prevention of tumor cell (Hibbs, et al., 1987, Science 235: 473–476) and microbial (Green, et al., 1992, J. Leuk. Biol. 50: 93–103) proliferation. Despite iNOS related systemic toxicity seen in various tissues, it would be advantageous to target local cell populations with a DNA sequence encoding iNOS or a biologically active fragment or derivative; such a gene therapy treatment will promote prophylactic and/or therapeutic actions in regard to diseases or disorders including but not necessarily limited to vascular occlusive disease, tumor cell growth associated with cancer, and numerous microbial infections.

3. SUMMARY OF THE INVENTION

The present invention has met the hereinbefore described needs. The present invention provides a cDNA clone for human tissue inducible nitric oxide synthase and a process for preparing the same.

More specifically, this invention provides a cDNA clone for human hepatocyte inducible nitric oxide synthase and a process for preparing the same. This process includes inducing nitric oxide synthase expression in human hepatocytes, identifying the presence of human hepatocyte nitric oxide synthase messenger RNA, collecting the human hepatocyte poly A messenger RNA, constructing a cDNA library from the human hepatocyte poly A messenger RNA, screening this cDNA library for human hepatocyte inducible nitric oxide synthase cDNA clones, and converting the human hepatocyte inducible nitric oxide synthase cDNA clones to a plasmid vector for obtaining a full length cDNA clone encoding human hepatocyte inducible nitric oxide synthase. This process further includes sequencing this cDNA, expressing the human hepatocyte inducible nitric oxide synthase cDNA as a protein in an expression system, and purifying the human hepatocyte inducible nitric oxide synthase protein encoded by the cDNA.

In a further embodiment of the invention, a cDNA clone encoding inducible nitric oxide synthase (iNOS) or a biologically active fragment or derivative thereof will be utilized in gene therapy techniques to treat any number of maladies effected by nitric oxide, including but not solely limited to (1) vascular occlusive disease associated with atherosclerosis; (2) resist vascular conduit occlusion due to thrombosis, intimal hyperplasia, or atherosclerosis; (3) treatment of accelerated vascular occlusive disease associated with diabetes mellitus which results in a high incidence of myocardial infarction, renal failure, stroke, blindness and limb loss at an early age; (4) treatment of cancer, specifically as an antitumor agent by increasing local nitric oxide concentrations in and around the tumor(s); and (5) treatment of various microbial infections.

In regard to treatments (1), (2) and (3) disclosed in the previous paragraph (herein referred to as vascular diseases or vascular disorders), local tissue specific expression of iNOS in targeted cells will result in the production of effective amounts of nitric oxide in the area of expression, so as to promote maximal local vasodilation, resist local thrombosis and potentially retard local smooth muscle cell proliferation, all of which may prevent the atherosclerotic disease process. It will be understood to one of ordinary skill in the art that any nucleic acid sequence encoding an inducible form of NOS, preferably human iNOS, regardless of the tissue source, is a candidate for utilization in, for example, gene therapy of vascular occlusive complications associated with atherosclerosis, vascular bypass, and diabetes derived vascular disease at sites of anastomosis. It will be further understood by the skilled artisan that any nucleic acid sequence which encodes a biologically active form of iNOS, preferably a human form of iNOS, including but not limited to a genomic or cDNA sequence or a fragment thereof which encodes a biologically active protein fragment or derivative, may be utilized in the present invention.

The present invention discloses treatment of vascular diseases or vascular disorders by increasing local iNOS activity, and thus nitric oxide concentrations, through targeting of mammalian cell populations which comprise the luminal lining of the arterial vessel, namely endothelial cells and vascular smooth muscle cells. More specifically, the target mammalian cells may be, but are not necessarily limited to: (1) in vitro cultured endothelial cells and (2) in vitro cultured vascular smooth muscle cells. These cells may be transduced with a DNA sequence encoding iNOS or a biologically active fragment or derivative thereof and may be subsequently utilized to repopulate arterial vessels of the patient. It is also within the scope of this invention to use iNOS-expressing endothelial cells, vascular smooth muscle cells or a combination of both to repopulate a diseased vessel or to seed a synthetic or autologous graft.

It will be preferred to utilize endothelial and/or smooth muscle cells obtained from the patient, which may be isolated and cultured by any number of methods known to one of ordinary skill in the art. A direct source of these arterial lumen cells may be obtained, for example, by harvesting a portion of a saphaneous vein or any other accessible vein or artery from the patient. This mode of obtaining target cell source material for in vitro culture prior to iNOS infection or transfection procedures will be especially useful in seeding a synthetic or autologous graft for transfer to the patient.

In another embodiment of the present invention, endothelial cells, vascular smooth muscle cells or a combination of both are targeted for in situ infection or transfection with a DNA sequence encoding iNOS or a biologically active fragment or derivative thereof so as to promote increased local iNOS expression within selected segments of arterial vessels.

It will be understood by the skilled artisan that similar procedures may be utilized for in vitro transfection or infection of endothelial cells and vascular smooth muscle cells. Both endothelial cells and vascular smooth muscle cells may be infected simultaneously through an in situ procedure, exemplified but not limited to the procedure outlined in Example Section 13.1.2.

It will also be understood that one or more endovascular procedures available to the skilled vascular surgeon may be utilized to prepare the diseased vessel for iNOS-based gene therapy as well as to deliver the DNA sequence encoding iNOS to the conduit area targeted for treatment. Such procedures, alone or in combination, include but are not necessarily limited to balloon angioplasty, laser-assisted balloon angioplasty, double balloon catheterization, mechanical endarterectomy and vascular endoscopy.

It will also be understood by the skilled artisan that a combination of strategies disclosed further within this specification may be utilized in conjunction with surgical vascular bypass procedures to promote a gene therapy based increase in local iNOS expression at sites of surgical repair or within a synthetic graft.

In a particular embodiment regarding targeting of in vitro cultured endothelial cells, vascular smooth muscle cells or a combination of both for gene therapy of vascular diseases, a DNA sequence encoding iNOS or a biologically active fragment thereof will be ligated to a viral vector in preparation for tissue specific delivery and expression. Virus vector systems utilized in the present invention include, but are not limited to (a) retroviral vectors, including but not limited to vectors derived from the Moloney murine leukemia virus (MoMLV) genome; (b) adeno-associated vectors; (c) adenovirus vectors; (d) herpes simplex virus vectors; (e) SV40 vectors; (f) polyoma virus vectors; (g) papilloma virus vectors; (h) picornavirus vectors; and (i) vaccinia virus vectors.

Additional strategies which the skilled artisan may utilize alone or in combination with viral vectors in targeting endothelial cells, vascular smooth muscle cells or a combination thereof for gene therapy of vascular diseases include but are not limited to (a) liposome-mediated transformation; (b) calcium phosphate $[Ca_3(PO_4)_2]$ mediated cell transfection; (c) in vitro transfection of target cells by electroporation; (d) DEAE-dextran mediated cell transfection, the in vitro transfected cells then utilized to repopulate the mammalian host; (e) polybrene mediated delivery; (f) protoplast fusion; (g) microinjection; (h) polylysine mediated transformation; and (i) direct injection of naked DNA. The genetically transformed cells generated by any of these strategies are then utilized to repopulate the mammalian host.

In a particular embodiment regarding the treatment of vascular diseases, a recombinant viral vector comprising a DNA sequence encoding iNOS or a biologically active fragment or derivative utilized to infect mammalian endothelial cells, vascular smooth muscle cells or a combination of both for repopulation of arterial vessels is a recombinant retroviral vector. The respective iNOS DNA sequence is ligated within the retroviral vector to form a retroviral-iNOS recombinant construct.

In a preferred embodiment regarding the treatment of vascular diseases, the iNOS sequence subcloned into an appropriate retroviral vector is a human iNOS sequence.

In a further preferred embodiment regarding use of a retroviral vector in gene therapy of vascular diseases, the recombinant retroviral vector is a MoMLV-iNOS construct. This iNOS containing retroviral construct comprises a human DNA sequence encoding iNOS or a biologically active fragment or derivative thereof.

In a preferred embodiment regarding use of a retroviral vector in gene therapy of vascular diseases, the MoMLV-iNOS construct is MFG-iNOS as depicted in FIG. 6 and FIG. 7. The MFG-iNOS construct is preferred for in situ infection of the target cell.

In another preferred embodiment regarding use of a retroviral vector in gene therapy of vascular diseases, the MoMLV-iNOS construction is DFG-iNOS-Neo as depicted in FIG. 6 and FIG. 8. The DFG-iNOS-Neo construct is preferred for in vitro infection of endothelial cells or vascular smooth muscle cells.

Any of the hereinbefore disclosed retroviral-iNOS recombinant constructs are then transferred into a standard retroviral packaging cell line. The recovered recombinant viral particles are then used to infect cultured endothelial cells or vascular smooth muscle cells in vitro. Treatment of vascular diseases is based further on transferring in vitro transduced or infected endothelial cells, vascular smooth muscle cells or a combination of both to specific segments of diseased arteries within the patient. A preferred mode of delivering infected endothelial cells, vascular smooth muscle cells or a combination of both utilizes a double balloon catheter to isolate a segment of a mammalian host artery which has been partially or totally denuded of its endothelial cell lining as often encountered following a balloon angioplasty procedure, endarterectomy or following surgical vascular bypass.

In vitro viral-mediated infection or vector-mediated transfection of endothelial cells or vascular smooth muscle cells with a DNA sequence encoding iNOS or a biologically active fragment thereof may be accomplished by numerous non-biologic and/or biologic carriers other than the hereinbefore mentioned retroviral vectors. Therefore, any non-biologic and/or biologic carrier possessing the ability to deliver an iNOS encoding DNA sequence to the local target such that iNOS is expressed at therapeutic or prophylactic levels may be utilized to practice the present invention.

For example, in an additional embodiment of the invention, a DNA sequence encoding iNOS or a biologically active fragment thereof may be subcloned into an adenoviral vector (Ad). The recombinant Ad-iNOS construct can be utilized to directly infect in vitro cultured endothelial cells, vascular smooth muscle cells or a combination thereof, or alternatively, can be delivered to the target cells through the association with liposome microcapsules.

Another embodiment of the invention involves a DNA sequence encoding iNOS or a biologically active fragment thereof which may be subcloned into an adeno-associated viral vector (AAV). As with an Ad-iNOS construct, the recombinant AAV-iNOS construct can be utilized to directly infect in vitro cultured endothelial cells, vascular smooth muscle cells or a combination thereof, or alternatively, can be delivered to the target cells through the association with liposome microcapsules.

In a further embodiment regarding the use of liposome-mediated techniques to deliver recombinant iNOS constructs to treat vascular diseases, a viral or non-viral vector comprising a DNA sequence encoding iNOS is delivered to the target cell by lipofectamine transfection. For example, a DNA sequence encoding iNOS or a biologically active fragment thereof is subcloned into a DNA plasmid vector such that iNOS is expressed subsequent to transfection of the target cell. Such non-viral based mammalian vectors include, but are not solely limited to, a plasmid DNA mammalian expression vector. Any eukaryotic promoter and/or enhancer sequence available to the skilled artisan which is known to up-regulate expression of iNOS may be used in mammalian expression vector constructs, including but not limited to a cytomegalovirus (CMV) promoter, a Rous Sarcoma (RSV) promoter, a Murine Leukemia (MLV) promoter, a herpes simplex virus (HSV) promoter, such as HSV-tk, a β-actin promoter, as well as any additional tissue specific or signal specific regulatory sequence that induces expression in the target cell or tissue of interest. A signal specific promoter fragment includes but is not limited to a promoter fragment responsive to TNF.

In one such embodiment, a DNA sequence encoding human iNOS is subcloned into the DNA plasmid expression vector, pCIS (Genentech), resulting in pCIS-iNOS. pCIS is a standard mammalian expression vector, containing an antibiotic resistance gene for propagation in *E. coli* and a CMV promoter active in mammalian cells. Such a construct, which may be constructed by one of ordinary skill with components available from numerous sources, will drive expression of an iNOS DNA fragment ligated downstream of the CMV promoter subsequent to transfection of the target cell. More specifically, a NotI/XhoI restriction fragment containing the human iNOS coding region is generated and isolated from pHINOS (pHINOS is deposited with the ATCC with accession number 75358) and ligated into NotI/XhoI digested pCIS. Alternatively, the isolated human iNOS sequence may be fused to any portion of the wild type human iNOS promoter sequence such that expression of human iNOS can be induced within the target cell.

It will become evident to one of ordinary skill in the art upon review of this specification that any of the viral or non-viral recombinant iNOS constructs hereinbefore described for use in infecting or transfecting in vitro cultured endothelial cells, vascular smooth muscle cells or a combination thereof may be used to infect or transfect target cell in situ. For example, balloon angioplasty may be utilized to dilate an occluded segment of diseased arterial vessel so as to reestablish the arterial lumen. The dilated segment is then segregated from the remainder of the arterial vessel by inserting a double balloon catheter. A viral or non-viral based recombinant iNOS construct may be selectively delivered through the catheter to the angioplasty site so as to promote in situ transfection or infection of endothelial and/or vascular smooth muscle cells with concomitant local increases in iNOS expression within the diseased vessel segment.

The present invention also discloses methods of human iNOS-directed gene therapy to promote antitumor effects in cancer patients. Such a human iNOS-directed gene therapy will provide a local increase in nitric oxide concentration within the area of the tumor to be treated, thus promoting antitumor activity without systemic increases in nitric oxide levels. As disclosed for iNOS-mediated treatment, a human derived DNA sequence encoding iNOS or a biologically active fragment or derivative thereof is preferred.

The isolated human iNOS DNA sequence may be manipulated and delivered to the target cell in vitro by transduction utilizing any of the viral and non-viral methods discussed in Section 5.2.1. The in vitro transduced target cells are then introduced into the patient so as to promote local iNOS expression at the tumor site. Therefore, it will be understood that any human iNOS DNA sequence encoding a biologically active fragment or derivative thereof, regardless of tissue source, is a candidate for antitumor treatments.

In one embodiment regarding cancer gene therapy, the patient is intravenously injected with in vitro transduced target cells, including but not limited to tumor infiltrating lymphocytes or cultured tumor cells harvested from the patient.

In a preferred method of delivering a human iNOS sequence to the target cell of interest, a recombinant retroviral vector comprising a DNA sequence encoding iNOS or a biologically active fragment thereof is utilized to infect tumor infiltrating lymphocytes. These infected tumor infiltrating lymphocytes are then reintroduced into the patient to promote local expression of iNOS at the tumor site.

In a preferred embodiment regarding gene therapy of cancer, DFG-iNOS-Neo (FIG. 8) is utilized to infect tumor infiltrating lymphocytes or cultured tumor cells harvested from the patient. Neomycin resistant cells are selected, followed by localization of these iNOS expressing cells to the region within and surrounding the active tumor.

In addition to the hereinbefore described use of viral vectors to infect target cells, any known non-viral vector described in this specification may be utilized to promote antitumor activity.

The human iNOS DNA sequences of the present invention may also be utilized in treating microbial infections. Specifically, iNOS-driven antimicrobial therapy will be utilized to treat microbes known to be susceptible to increased concentrations of nitric oxide. For example, nitric oxide is known to be a cytotoxic effector molecule against mycobacteria, helminths, fungi, protozoa and DNA viruses. Therefore, the present invention discloses methods of increasing concentrations of nitric oxide locally at the site of infection by targeting the infected cell or tissue type with a DNA sequence encoding iNOS activity, preferably human iNOS, capable of being expressed at a therapeutic level and duration so as to surmount the disease.

In a preferred embodiment of utilizing iNOS-driven antimicrobial therapy, the target cell type is human hepatocytes infected with the sporozoa *Plasmodium*, the causative agent of malaria. Human malaria is caused by one of four species of *Plasmodium*: *P. falciparum, P. malariae, P. vivax* and *P. ovale*.

In a preferred embodiment of treating malaria via iNOS-antimicrobial therapy, the iNOS-vector is delivered via liposome mediated transformation of the target hepatocytes.

In an especially preferred embodiment of treating malaria via iNOS-antimicrobial therapy, the liposomes are modified by insertion of an hepatocyte specific asialoprotein into the liposome membrane prior to administration to the patient.

Another embodiment of utilizing iNOS-vectors in antimicrobial therapy involves treatment of lung borne microbial infections, including but not limited to tuberculosis and leprosy.

A preferred treatment of tuberculosis by iNOS-antimicrobial therapy involves targeting an iNOS vector to the target tissue by viral mediated transformation of cells within the target tissue.

A preferred method of treating tuberculosis by iNOS-antimicrobial therapy is adenovirus-mediated delivery to the site of infection.

Another preferred method of treating tuberculosis by iNOS-driven biologic therapy is retroviral mediated delivery, as discussed in Section 5.2.1. iNOS-based vectors disclosed in Sections 5.2.1 and 5.2.2 may also be utilized in retroviral-mediated delivery techniques to treat tuberculosis.

With the aid of this specification, it would be within the realm of the artisan of ordinary skill to construct an iNOS vector compatible with the delivery system of choice for use in treating tuberculosis.

A preferred method of administering an iNOS-infected retrovirus within infected regions of lung tissue is inhalatory administration, in the form of an aerosol mist.

Another embodiment of the invention relates to treatment of *Mycobacterium leprae*, the causative agent of leprosy. The preferred mode of treating leprosy by gene therapy entails retroviral-mediated transduction of target tissue cell types by inhalatory administration.

It is an object of the present invention to provide for the molecular cloning and characterization of an inducible nitric oxide synthase in human tissues.

It is an object of the present to provide for the molecular cloning and characterization of an inducible nitric oxide synthase from human hepatocytes.

It is an object of the present invention to isolate a cDNA clone for human tissue inducible nitric oxide synthase.

It is an object of the present invention to isolate a cDNA clone for human hepatocyte inducible nitric oxide synthase.

It is an object of the present invention to provide a process for expressing and purifying human tissue inducible nitric oxide synthase enzyme.

It is an object of the present invention to provide a process for expressing and purifying human hepatocyte inducible nitric oxide synthase enzyme.

It is an object of this invention to provide for the regulation of gene expression for the human hepatocyte inducible nitric oxide synthase enzyme.

It is an object of this invention to provide for a protein including a human inducible nitric oxide synthase substantially free of other human proteins.

It is an object of this invention to promote vascular gene therapy to provide prophylactic and therapeutic relief from vascular diseases including but not limited to vascular occlusive diseases associated with atherosclerosis, vascular bypass, and associated with diabetes by providing transfected endothelial cells, vascular smooth muscle cells or a combination of both which express iNOS or a biologically active fragment thereof to a patient's diseased blood vessel, a vascular conduit, or blood vessel partly or totally denuded of its endothelial lining.

It is an object of this invention to provide therapeutic treatment of tumor growth by utilizing iNOS-driven gene therapy techniques to increase local nitric oxide concentrations so as to inhibit tumor growth.

It is an object of this invention to provide therapeutic relief from various microbial infections susceptible to attack by utilizing iNOS-driven gene therapy techniques to increase local concentration of nitric oxide at or around the site of infection, especially the various pulmonary and hepatic infections described in this specification.

These and other objects of the invention will be more fully understood from the following description of the invention, the figures, the sequence listing and the claims appended hereto.

3.1. Definitions

The terms listed below, as used herein, will have the meaning indicated.

| | |
|---|---|
| mRNA | messenger RNA |
| DNA | deoxyribonucleic acid |
| cDNA | complementary deoxyribonucleic acid |
| NO | nitric oxide |
| NOS | nitric oxide synthase |
| cNOS | constitutive nitric oxide synthase |
| iNOS | inducible nitric oxide synthase |

| | |
|---|---|
| EDRF | endothelium derived relaxing factor |
| LPS | lipopolysaccharide |
| CMV | cytomegalovirus |
| Ad | adenovirus |
| AAV | adeno-associated virus |
| IRES | internal ribosome entry site |
| PTFE | polytetrafluoroethylene |

As used herein, the term "patient" includes members of the animal kingdom including but not limited to human beings.

As used herein, the term "mammalian host" includes mammals, including but not limited to human beings.

As used herein, the term "biologically active fragment or derivative thereof" includes any iNOS protein fragment possessing similar biological activity as wild type iNOS, or a derivative such as an iNOS substitution, addition and/or deletion mutant which maintains similar biological activity as wild type iNOS. One of ordinary skill in the art may use the present specification to generate such changes in the wild type iNOS DNA sequence so as to express variants of wild type iNOS which retain the biological activity necessary to be useful in the presently disclosed gene therapy applications.

4. BRIEF DESCRIPTION OF THE FIGURES

FIGS. 1A through 1G show the cDNA sense sequence (top line of each horizontal row; SEQ ID NO: 1) and the amino acid sequence of amino acids 1–1153 (bottom line of each horizontal row; SEQ ID NOS: 1 and 2) for the cDNA clone for human hepatoeyte inducible nitric oxide synthase.

Figure 6:
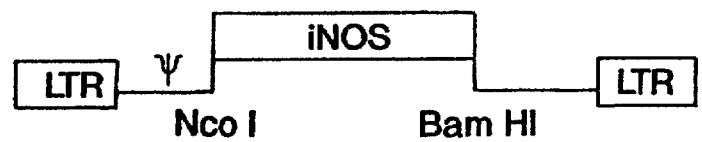
Figure 6:
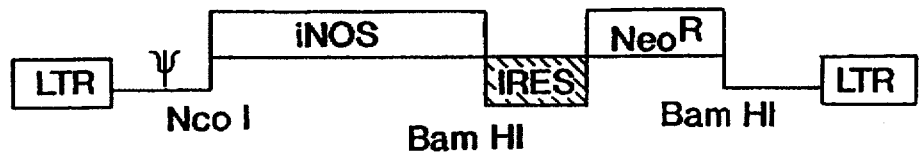

FIG. 6 shows the MFG-iNOS and DFG-iNOS-Neo recombinant retroviral vectors utilized to exemplify the gene therapy applications to treat diseases or disorders disclosed throughout this specification. Neo encodes resistance to neomycin; the IRES fragment allows translation of a polyeistronic mRNA; LTR are long terminal repeats of the MoMLV genome; iNOS is the cDNA encoding human hepatocyte iNOS.

Figure 7:
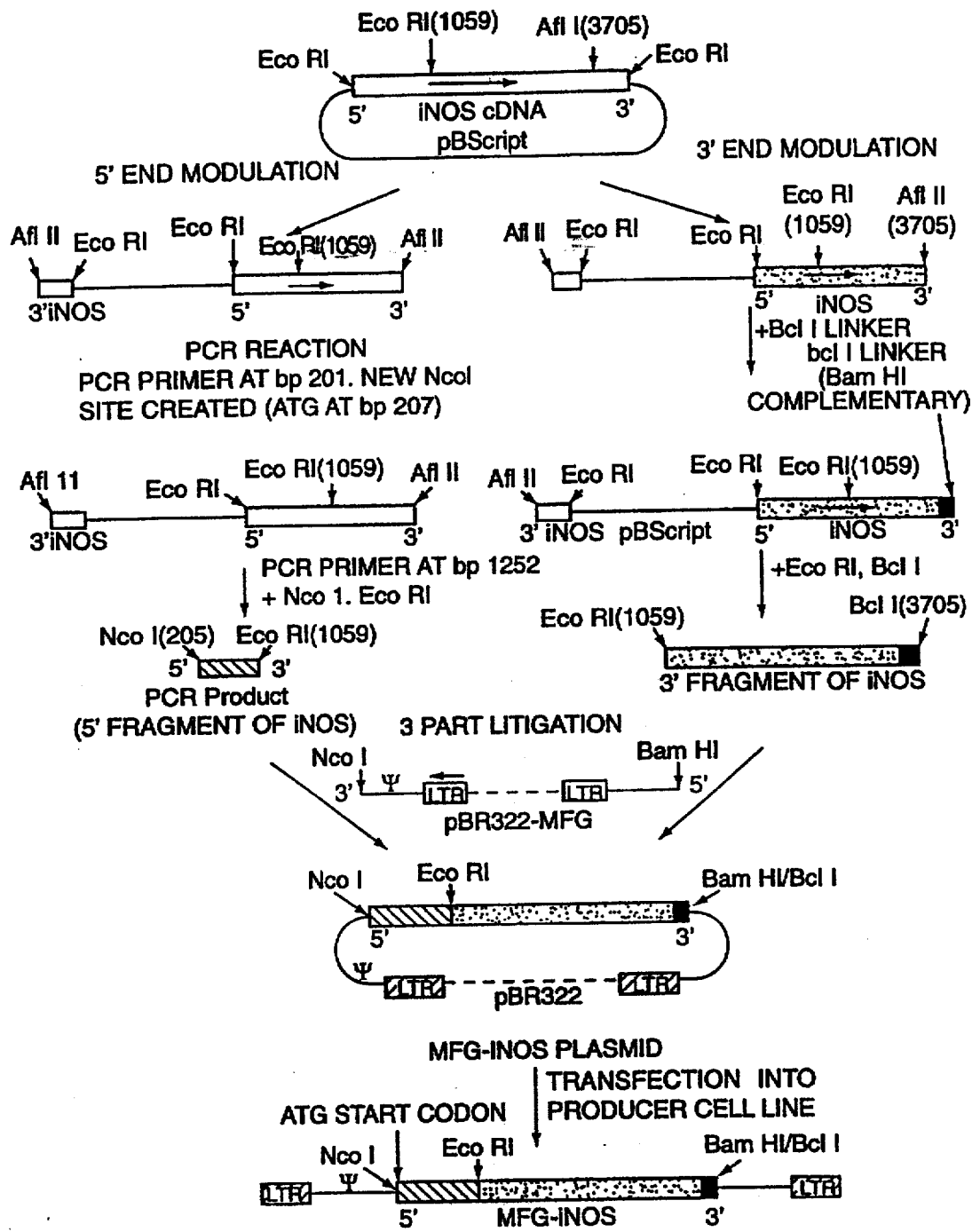

FIG. 7 shows detailed methods utilized to construct MFG-iNOS, a recombinant retroviral vector utilized to exemplify various gene therapy applications disclosed throughout this specification.

Figure 8:
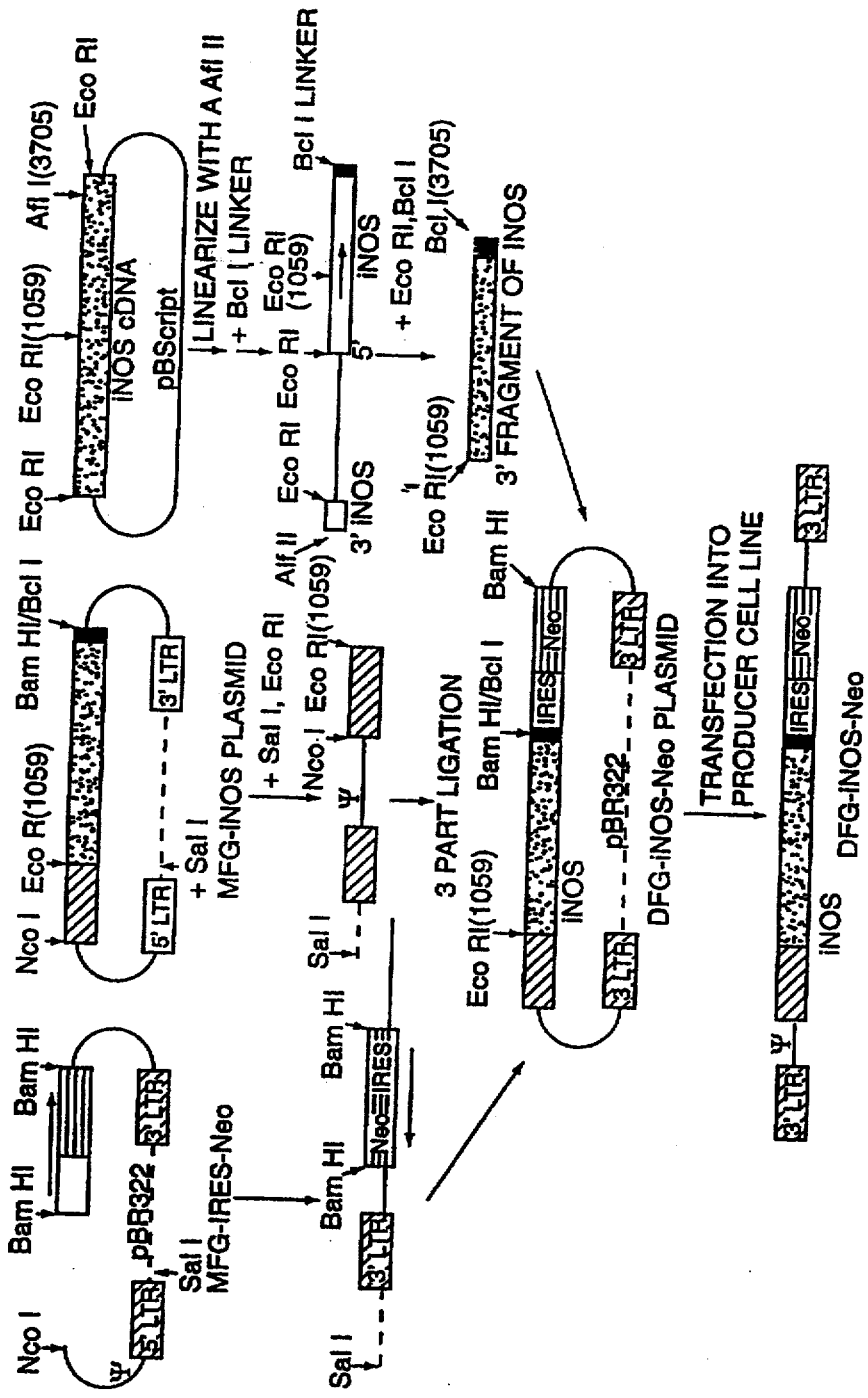

FIG. 8 shows detailed methods utilized to construct DFG-iNOS-Neo, a recombinant retroviral vector utilized to exemplify various gene therapy applications disclosed throughout this specification.

Figure 9:
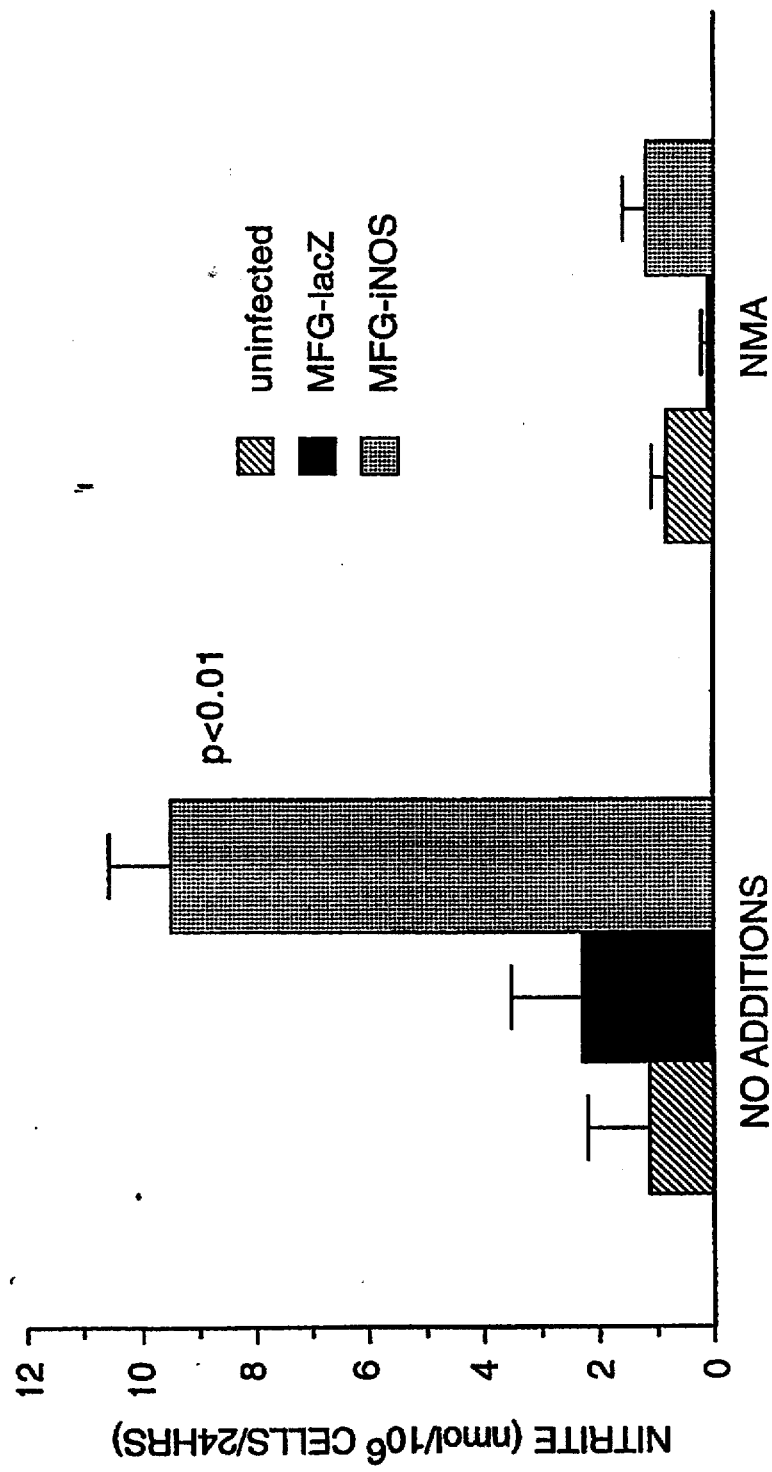

FIG. 9 shows nitrite production in cultured endothelial cells infected with MFG-iNOS, MFG-lacZ and uninfected cells in the absence and presence of the iNOS inhibitor, $N^G$-monomethylarginine.

Figure 10:
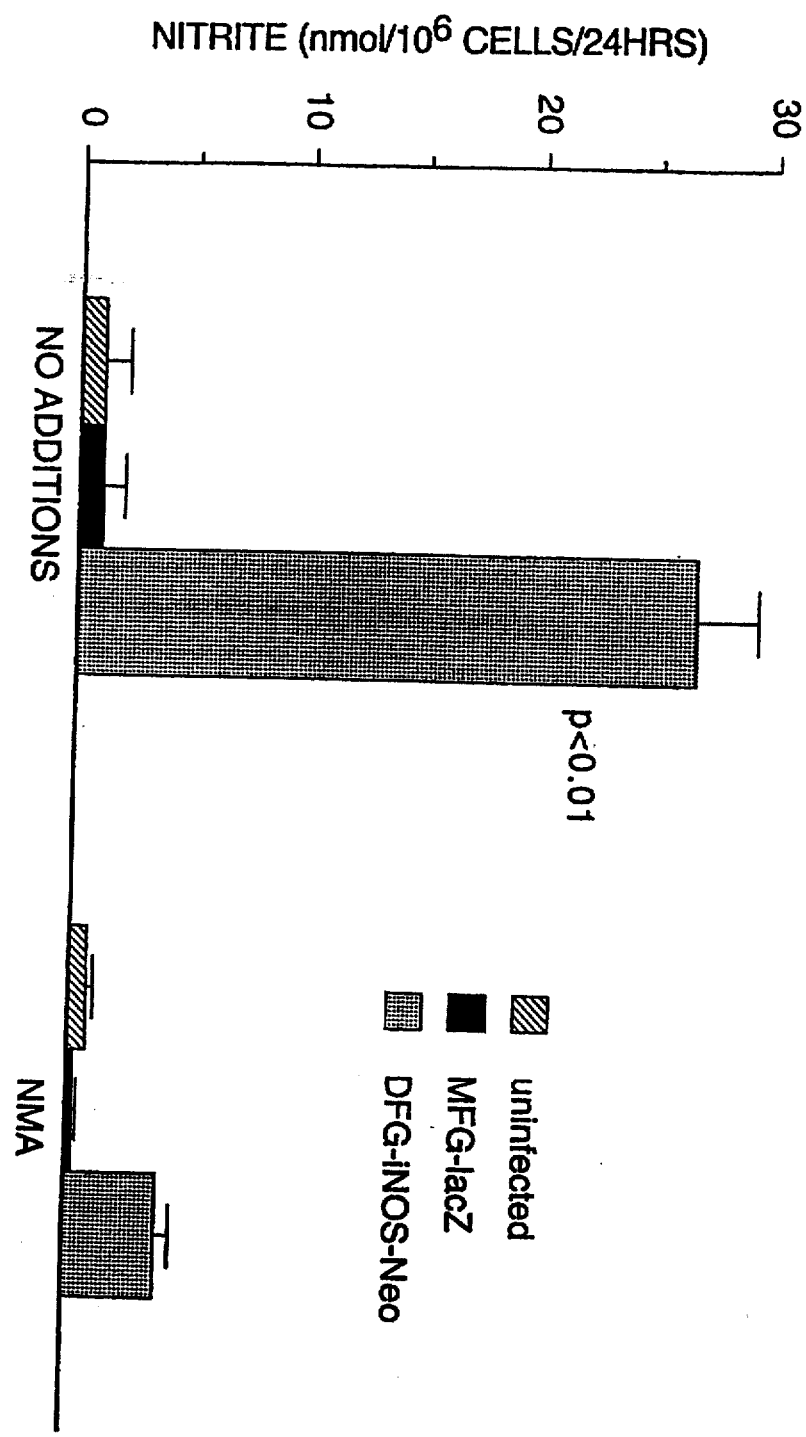

FIG. 10 shows nitrite production in cultured endothelial cells infected with DFG-iNOS-Neo, MFG-lacZ and uninfected cells in the absence and presence of the iNOS inhibitor, $N^G$-monomethylarginine.

Figure 11:
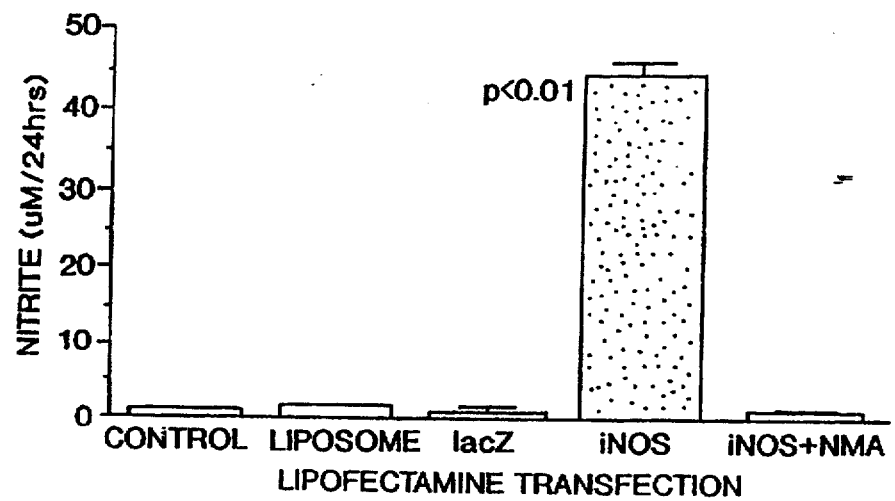

FIG. 11 shows nitrite production in vascular smooth muscle cells after lipofectamine transfection of pCIS-iNOS in the absence and presence of $N^G$-monomethylarginine, pSV-lacZ, and a plasmid-less control with or without the addition of liposomes.

5. DETAILED DESCRIPTION OF THE INVENTION

Nitric oxide is a biologic mediator derived from the amino acid L-arginine. Nitric oxide synthase (NOS) acts upon L-arginine to oxidize one of the guanidino nitrogens to nitric oxide while citrulline is formed from the remainder of the L-arginine molecule. While it is understood by those skilled in the art that nitric oxide has normal physiologic intracellular and extracellular regulatory functions, excessive production of nitric oxide can be both detrimental and beneficial. It will be appreciated by those skilled in the art that there are no other readily available sources of human tissue inducible nitric oxide synthase. The present invention provides a cDNA clone for human tissue inducible nitric oxide synthase and a process for preparing the same. Therefore, the cloning and expression of a human tissue nitric oxide synthase cDNA of the present invention provides for a source of the enzyme for developing selective inhibitors of nitric oxide synthase. The present invention also relates to gene therapy techniques utilizing a human iNOS DNA sequence to provide therapeutic relief from diseases or disorders such as vascular occlusive disease associated with atherosclerosis, vascular bypass, and diabetes mellitus, tumor cell growth associated with cancer, and microbial infections.

The cloning and expression of a human tissue nitric oxide synthase cDNA of the present invention provides for a source of the enzyme in a sufficiently high concentration for providing a therapeutic purpose.

5.1. Isolation and Characterization of a cDNA Clone Coding for a Human Inducible Nitric Oxide Synthase In one embodiment of this invention, a process for preparing a cDNA clone coding for a human tissue inducible nitric oxide synthase is provided. This process includes inducing the expression of human tissue nitric oxide synthase in vitro, identifying the presence of human tissue nitric oxide synthase messenger RNA (mRNA) by employing a cross-species cDNA probe capable of hybridizing with the human tissue inducible nitric oxide synthase mRNA, collecting the human tissue poly A mRNA which included the human tissue nitric oxide synthase mRNA, constructing a cDNA library from the human tissue poly A mRNA using a reverse transcriptase enzyme and inserting a strand of the cDNA into a phage vector, screening the cDNA library for human tissue inducible nitric oxide synthase clones with a cross-species iNOS cDNA probe, incubating the phage vector coning the cDNA with a bacteria for forming at least one positive plaque containing the cDNA clone for human tissue inducible nitric oxide synthase, rescuing the cDNA clone from the phage vector by employing a helper phage, and converting the rescued cDNA clone to a plasmid vector for obtaining a full length cDNA clone encoding human tissue inducible nitric oxide synthase.

In another embodiment of this invention, this process, as hereinbefore described, further includes excising the cDNA insert for human tissue inducible nitric oxide synthase from the plasmid vector. This process also includes confirming the cDNA insert by employing dideoxynucleotide DNA sequencing. Further, this process includes confirming the cDNA insert by employing Southern blot hybridization with a cross-species cDNA probe derived from murine macrophage iNOS.

In another embodiment of this invention, the process, as hereinbefore described, includes expressing the human tissue inducible nitric oxide synthase cDNA protein in an expression system, such as for example, a bacterial expression system or a mammalian expression system.

It will be appreciated by those skilled in the art that the cloned human inducible nitric oxide synthase cDNA obtained through the methods described herein may be recombinantly expressed by molecular cloning into an expression vector containing a suitable promoter and other appropriate transcription regulatory elements, and transferred into prokaryotic or eukaryotic host cells to produce recombinant inducible nitric oxide synthase. Techniques for such manipulations are fully described in Maniatis, et al., infra, and are well known in the art.

Expression vectors are defined herein as DNA sequences that are required for the transcription of cloned copies of genes and the translation of their mRNAs in an appropriate host. Such vectors can be used to express eukaryotic genes in a variety of hosts such as for example bacteria, bluegreen algae, plant cells, insect cells and animal cells.

Specifically designed vectors allow the shuttling of DNA between hosts such as bacteria-yeast or bacteria-animal cells. An appropriately constructed expression vector should contain: an origin of replication for autonomous replication in host cells, selectable markers, a limited number of useful restriction enzyme sites, a potential for high copy number, and active promoters. A promoter is defined as a DNA sequence that directs RNA polymerase to bind to DNA and initiate mRNA synthesis A strong promoter is one which causes mRNAs to be initiated at high frequency. Expression vectors may include, but are not limited to, cloning vectors, modified cloning vectors, specifically designed plasmids or viruses. A variety of mammalian expression vectors may be used to express recombinant inducible nitric oxide synthase in mammalian cells.

Commercially available bacterial expression vectors which may be suitable for recombinant inducible nitric oxide synthase expression, include but are not limited to, pKC30 (ATCC 37286), pPLa2311 (ATCC 31694), pBR322 (ATCC 31344 and 37017), ptac12 (ATCC 37138), lambda gt11 (ATCC 37194), pAS1 (ATCC39262), pLC24, pSB226, SV40 and pKK 223-3.

Commercially available mammalian expression vectors which may be suitable for recombinant inducible nitric oxide synthase expression, include but are not limited to, pBC12B1(ATCC 67617), pMCIneo (Stratagene), pXT1 (Stratagene), pSG5 (Stratagene), EBO-pSV2-neo (ATCC 37593)pBPV-i(8-2) (ATCC 37110), pdBPV-MMTneo(342-12) (ATCC 37224), pRSVgpt (ATCC 37199), pRSVneo (ATCC 37198), pSV2-dhfr (ATCC 37146), pUCTag (ATCC 37460), and lambda ZD35 (ATCC 37565).

DNA encoding inducible nitric oxide synthase may also be cloned into an expression vector for expression in a recombinant host cell. Recombinant host cells may be prokaryotic or eukaryotic, including but not limited to bacteria, yeast, mammalian cells including but not limited to cell lines of human, bovine, porcine, monkey and rodent origin, and insect cells including but not limited to drosophila derived cell lines. Cell lines derived from mammalian species which may be suitable and which are commercially available, include but are not limited to, CV-1 (ATCC CCL70), COS-1 (ATCC CRL1650), COS-7 (ATCC CRL1651), CHO-K1 (ATCC CCL61), 3T3 (ATCC CCL92), NIH/3T3 (ATCC CRL 1658), HeLa (ATCC CCL2), C1271 (ATCC CRL1616), BS-C-1 (ATCC CCL26) and MRC-5 (ATCC CCL171). The bacterial cell most used for expression of recombinant protein is *Escherichia coli*. There are various strains of *E. coli* available and are well known in the art.

The expression vector may be introduced into host cells via any one of a number of techniques including but not limited to transformation, transfection, infection, protoplast fusion, and electropotation.

In a preferred embodiment of this invention, the process, as hereinbefore described, includes expressing the human tissue inducible nitric oxide synthase protein in a baculovirus expression system.

Another embodiment of this invention provides for a process, as hereinbefore described, including purifying the human tissue inducible nitric oxide synthase protein.

In a preferred embodiment of this invention, the process, as hereinbefore described, includes employing as the human tissue inducible nitric oxide synthase a human hepatocyte inducible nitric oxide synthase. This process further includes employing as the human tissue inducible nitric oxide synthase protein a human hepatocyte inducible nitric oxide synthase protein.

In another embodiment of this invention, a process is provided, as hereinbefore described, including inducing the human tissue nitric oxide synthase in vitro by stimulating a human tissue in vitro with at least one of the following (1) at least one cytokine, such as for example a cytokine selected from the group consisting of tissue necrosis factor (TNF), interleukin-1 (IL-1), and interferon-gamma (IFN-g), (2) at least one bacterial endotoxin including, such as for example, a bacterial lipopolysaccharide (LPS) and (3) combinations thereof.

A further preferred embodiment of this invention provides a process, as hereinbefore described, that includes constructing a cDNA library from the human tissue poly A mRNA which includes the human tissue iNOS mRNA using a reverse transcriptase enzyme and inserting cDNA strands having a length of about at least 1,000 base pairs into the phage vector. In yet another preferred embodiment, a process is provided, as hereinbefore described, that includes employing lambda Zap II as the phage vector.

In another embodiment of this invention, a process is provided, as hereinbefore described, including screening the cDNA library by incubating the phage vector for about 6 to 24 hours with a bacteria at a temperature of about 34 to 40 degrees centigrade for effectuating phage lysis of the bacteria. This process further includes rescuing the cDNA clone from the phage vector by employing a helper phage such as for example ExAssist helper phage (Stratagene, La Jolla, Calif.).

In a preferred embodiment of this invention, a process, as hereinbefore described, is provided including converting the rescued cDNA clone to the plasmid vector for obtaining a full length cDNA done encoding the human tissue inducible nitric oxide synthase wherein the plasmid vector includes pBluescript (Stratagene, La Jolla, Calif.).

In another preferred embodiment of this invention, a process, as hereinbefore described, is provided including employing as the human tissue inducible nitric oxide synthase a human hepatocyte inducible nitric oxide synthase.

Another embodiment of this invention provides for a process for producing human hepatocyte inducible nitric oxide synthase protein comprising providing a replicatable DNA expression vector capable of expressing a DNA sequence encoding human hepatocyte inducible nitric oxide synthase in a suitable host, transforming the host to obtain a recombinant host, and maintaining the recombinant host under conditions permitting expression of the DNA sequence to provide human hepatocyte inducible nitric oxide synthase protein.

Another embodiment of this invention provides a human tissue inducible nitric oxide synthase cDNA clone. A preferred embodiment of this invention provides a human hepatocyte inducible nitric oxide synthase cDNA clone. The human hepatocyte inducible nitric oxide synthase cDNA clone of this invention has a cDNA coding for the amino acid sequence shown in FIGS. 1A–G. FIGS. 1A–G show the cDNA sense sequence (top line of each horizontal row; SEQ ID NO:1) and the deduced amino acid sequence of amino acids 1–1153 (bottom line of each horizontal row; SEQ ID NO: 1 and 2) for the cDNA clone for the human hepatocyte inducible nitric oxide synthase of this invention. FIGS. 1A–G show that the cDNA sequence for the human hepatoeyte inducible nitric oxide synthase of this invention is 4,145 nucleotide bases long with the start codon beginning at base number 207 and the stop codon ending at base number 3668. The cDNA double strand sequence was determined using the Sanger dideoxynucleotide sequence technique (Sanger, et al., 1977, Proc. Natl. Acad. Sci. USA 74: 5463–5467) on a Genesis 2000 sequencing system (USA, Cleveland, Ohio).

Another embodiment of this invention provides a human tissue inducible nitric oxide synthase recombinant protein expressed from a human tissue inducible nitric oxide synthase cDNA clone. In a preferred embodiment, a human hepatocyte inducible nitric oxide synthase recombinant protein expressed from a human hepatocyte inducible nitric oxide synthase cDNA done is provided.

Another embodiment of this invention provides for a protein comprising a human inducible nitric oxide synthase substantially free of other human proteins.

Another embodiment of this invention provides for an isolated DNA sequence encoding human inducible nitric oxide synthase consisting essentially of an initiation codon positioned upstream and adjacent to an open reading frame consisting essentially of a DNA sequence encoding human inducible nitric oxide synthase.

A further embodiment of this invention provides for an isolated DNA sequence encoding human inducible nitric oxide synthase consisting essentially of an initiation codon positioned upstream and adjacent to an open reading frame consisting essentially of a DNA sequence encoding human inducible nitric oxide synthase protein. The human inducible nitric oxide synthase protein begins at the initiation codon and terminates at a stop codon.

In yet another embodiment of this invention, a recombinant plasmid is provided containing a recombinant plasmid pHINOS having a deposit accession number ATCC 75358 deposited with the American Type Culture Collection. A further embodiment of this invention provides for bacteria transformed by the recombinant plasmid pHINOS.

In another embodiment of this invention a microorganism is provided containing a HINOS cDNA plasmid transformed in E. coli SOLR bacteria having a deposit accession number ATCC 69126 deposited with the American Type Culture Collection.

5.2. Gene Therapy Applications Utilizing Human iNOS

5.2.1. Vascular Gene Therapy Utilizing Human iNOS

Vascular occlusive disease due to atherosclerosis results in significant morbidity in the form of stroke, myocardial infarction, and limb loss. No effective means to resist these changes currently exist. The capacity to bypass occluded vessels is often limited by thrombosis and occlusion of the bypass graft.

Accelerated vascular occlusive disease associated with diabetes mellitus results in a high incidence of myocardial infarction, renal failure, stroke, blindness, and limb loss at an early age. Because smaller sized arteries are often preferentially involved, therapies such as bypass or angioplasty, aimed at alleviating stenotic vessels, are frequently ineffective or complicated by early thrombosis or early restenosis. Factors that contribute to atheroselerosis and diabetic vascular lesions include endothelial injury and dysfunction, macrophage and platelet accumulation, lipid and lipoprotein accumulation, accumulation of glycosylation products, and vascular smooth muscle cell proliferation (Colwell, 1991, Am. J. Med. 90: 6A-50S–6A-54S).

The present invention discloses treatment of vascular diseases or vascular disorders by increasing local iNOS expression through targeting of the mammalian cell populations which form the arterial luminal lining, namely endothelial cells and vascular smooth muscle cells. More specifically, the target mammalian cells may be, but are not necessarily limited to: (1) in vitro cultured endothelial cells and (2) in vitro cultured vascular smooth muscle cells, which may be transfected or infected with a DNA sequence encoding iNOS or a biologically active fragment or derivative thereof and subsequently utilized to repopulate arteries of the patient. It is also within the scope of this invention to use a combination of infected and/or transfected endothelial and vascular smooth muscle cells for repopulation of a diseased vessel.

It will be preferred to utilize endothelial and/or smooth muscle cells obtained from the patient, which will be placed into culture by any number of methods known to one of ordinary skill in the art. A source of these arterial-based cells may be obtained by harvesting a source these cells from the patient, including but not limited to harvesting a portion of a saphaneous vein from the patient. This mode of obtaining target cell source material for in vitro culture prior to iNOS infection or transfection procedures will be especially useful in seeding a synthetic or autologous graft for transfer to the patient.

In another embodiment of the present invention, endothelial cells, vascular smooth muscle cells or a combination of both are targeted for in situ infection or transfection with a DNA sequence encoding iNOS or a biologically active fragment or derivative thereof so as to promote increased local iNOS expression within selected segments of arterial vessels.

It is a preferred aspect of the invention to utilize a human nucleic acid fragment encoding an iNOS protein or biologically active fragment. In regard to directing a human iNOS construct to the appropriate cell type and arterial location, a further preferred embodiment involves use of the cDNA clone encoding human hepatocyte iNOS or a biologically active fragment thereof. This cDNA clone may be utilized to generate various biologically active iNOS constructs for use in gene therapy applications to increase localized arterial iNOS expression for treatment of vascular diseases including but by no means limited to vascular occlusive disease associated with atherosclerosis and diabetes mellitus, vascular disorders resulting in a high incidence of myocardial infarction, renal failure, stroke, blindness and limb loss at an early age, as well as prevention of intimal hyperplasia. Cell and arterial specific expression of human iNOS in targeted cells will result in local production of prophylactically and therapeutically effective amounts of nitric oxide in the area of expression. Local iNOS expression will promote maximal local vasodilation, resist local thrombosis and potentially retard local vascular smooth muscle cell proliferation, all of which may resist the atherosclerotic disease process and vascular conduit occlusion. However, it will be further understood to one of ordinary skill in the art that any DNA sequence encoding an inducible form of human iNOS, regardless of the tissue source, is a candidate for utilization in gene therapy of vascular occlusive disease in humans. It will be further understood by the skilled artisan that any isolated DNA sequence encoding a protein or protein fragment which mimics the biological activity of human hepatocyte iNOS may be utilized to practice the present invention. Such isolated DNA sequences include, but are not necessarily limited to (1) an isolated cDNA or genomic fragment encoding human hepatocyte iNOS or a biologically active fragment thereof; (2) an isolated cDNA, genomic fragment or nucleic acid fragment encoding a biologically active protein or protein fragment of a non-hepatocyte human iNOS; (3) an isolated cDNA, genomic fragment or nucleic acid fragment thereof encoding a biologically active protein or protein fragment thereof of a non-human iNOS; or (4) a synthetic DNA molecule encoding a polypeptide fragment with similar biological activity as described for iNOS.

The DNA sequence encoding iNOS may be delivered to endothelial or vascular smooth muscle target cells by viral or non-viral mediated routes. Virus vectors utilized in the present invention include, but are not limited to (a) retroviral vectors, including but not limited to vectors derived from Moloney murine leukemia virus (MoMLV); (b) adeno-associated vectors; (c) adenovirus vectors; (d) herpes simplex virus vectors; (e) SV40 vectors; (f) polyoma virus vectors; (g) papilloma virus vectors; (h) picornavirus vectors; and (i) vaccinia virus vectors. Depending on the virus vector system chosen, techniques available to the skilled artisan are utilized to infect the target cell of choice with the recombinant viral vector.

By way of example, and not of limitation, a recombinant retroviral vector comprising a DNA sequence encoding iNOS or a biologically active fragment thereof is utilized to infect cultured mammalian endothelial cells which are then used to repopulate arterial vessels or vascular bypass grafts. The retroviral-iNOS recombinant construct is transferred into a standard retroviral packaging cell line and the recovered viral particles are used to infect cultured endothelial cells. These in vitro infected cell populations are then reintroduced into the patient.

Any number of retroviral constructs which express a biologically active form of iNOS may be utilized by the skilled artisan in practicing the invention. However, a preferred embodiment of the invention depends upon infection of endothelial cells with an iNOS-containing recombinant Moloney murine leukemia virus (MoMLV) retroviral vector. Although MoMLV is a RNA virus, it has a DNA intermediate form that stably integrates into the genome of the host cell. The virus has two long terminal repeats (LTRs) at the 5' and 3' end of the proviral DNA that contain promoter, polyadenylation, and integration sequences required for the viral life cycle. A packaging sequence, termed psi, is also required in cis for the production of infectious virus. The virus encodes three proteins, gag, pol, and env, that are required in trans for viral replication. The gag and pol proteins are expressed from a non-spliced message whereas the env protein is expressed from a spliced message generated using the 5' and 3' splice sites shown. To generate a recombinant retroviral vector, the gag, pol, and env genes were removed, resulting in the replication deficient MFG derivative of MoMLV. The cDNA encoding iNOS was subcloned into MFG, resulting in MFG-iNOS. In MFG-iNOS, the gene is expressed from a LTR-driven spliced message. The MFG-iNOS construct has the psi site required for packaging of the recombinant RNA into virions. To generate infectious virus, the proviral DNA is transfected into a packaging cell line that constitutively produces gag, pol, and env proteins. FIG. 1A–G shows the sequence of the cDNA encoding the human hepatocyte iNOS and is inserted into the NcoI and BamHI cloning sites of the retroviral vector MFG (FIG. 6 and FIG. 7; for a review of retroviral vectors, see Miller, 1992, Current Topics in Microbiology and Immunology 158: 1–24).

One of ordinary skill in the art will understand any additional isolated DNA sequence or synthetically produced DNA sequence encoding a biologically active portion of iNOS, as hereinbefore disclosed, may be subcloned into a retroviral vector for eventual in vitro infection of cultured endothelial cells or vascular smooth muscle cells. Infected endothelial cells or vascular smooth muscle cells may then be delivered to specific tissue target sites within the patient as described within this specification.

The present invention also discloses the use of iNOS-retroviral vectors in gene therapy applications to treat vascular disease by in situ infection or transfection of endothelial cells or vascular smooth muscle cells with a DNA sequence encoding iNOS so as to promote increased local iNOS expression within selected arterial segments or vascular bypass grafts.

In vitro viral-mediated infection or vector-mediated transfection of endothelial cells with a DNA sequence encoding iNOS or a biologically active fragment thereof to treat vascular disease may be accomplished by numerous non-biologic and/or biologic carriers other than the hereinbefore mentioned retroviral vectors.

For example, in an additional embodiment of the invention, a DNA sequence encoding iNOS or a biologically active fragment thereof may be subcloned into an adenovirus viral vector. Any adenovirus (Ad) vector system that will promote expression of iNOS in the target cell of interest may be utilized. Any number of eukaryotic promoters available to one of ordinary skill in the art may be used in constructing an adenovirus-iNOS gene therapy vector. Therefore, any eukaryotic promoter and/or enhancer sequences available to the skilled artisan which are known to control expression of the nucleic acid of interest may be used in Ad vector constructs, including but not limited to a cytomegalovirus (CMV) promoter, a Rous Sarcoma (RSV) promoter, a Murine Leukemia (MLV) promoter, a β-actin promoter, as well as any additional tissue specific or signal specific regulatory sequence that induces expression in the target cell or tissue of interest. Adenovirus gene therapy vectors will be advantageous due to, for example, (1) efficient infection of nondividing cells such as endothelial cells and hepatocytes and, (2) the transient nature of adenovirus vector expression in the target cell, which will be advantageous in applications to prevent thrombosis immediately post-angioplasty.

In an additional embodiment of the invention, a DNA sequence encoding iNOS or a biologically active fragment thereof may be subcloned into an adeno-associated viral vector (AAV). One of ordinary skill in the art may construct a recombinant AAV-iNOS vector to be utilized in any one of a number of gene therapy applications. In contrast to retroviral terminal repeat sequences, AAV terminal repeat sequences do not contain regulatory sequences which promote foreign gene expression. As discussed above for Ad vectors, any eukaryotic promoter and/or enhancer sequences available to the skilled artisan which are known to control expression of the nucleic acid of interest may be used in AAV vector constructs, including but not limited to a cytomegalovirns (CMV) promoter, a Rous Sarcoma (RSV) promoter, a Murine Leukemia (MLV) promoter, a β-actin promoter, as well as any additional tissue specific or signal specific regulatory sequence that induces expression in the target cell or tissue of interest.

An appropriate recombinant AAV-iNOS vector can be utilized to directly infect in vitro cultured endothelial cells or vascular smooth muscle cells. Endothelial cells infected with recombinant AAV-iNOS can then be delivered to the specific tissue target site utilizing methods known in the art, including but not limited to the catheterization techniques disclosed within this specification. Alternatively, recombinant AAV-iNOS can be delivered to the target cell through association with liposome microcapsules. A transfection protocol utilizing a hybrid liposome:AAV construct involves using an AAV vector (most likely with both LTR's present) comprising an iNOS DNA sequence. This construct is cotransfected into target endothelial cells or vascular smooth muscle cells with a plasmid containing the rep gene of AAV. Transient expression of the rep protein enhances stable integration of the recombinant AAV-iNOS genome into the endothelial cell or vascular smooth muscle cell genome.

In addition to the hereinbefore described use of viral vectors to infect target cells, any known non-viral vector that is capable of expression upon transfection of a specified eukaryotic target cell may be utilized to practice the present invention. Such non-viral based vectors include, but are not solely limited to, plasmid DNA.

One of ordinary skill in the art will be guided by the literature to choose an appropriate DNA plasmid vector for use in the present invention. As discussed above for recombinant Ad and AAV vectors, any eukaryotic promoter and/or enhancer sequences available to the skilled artisan which are known to control expression of the nucleic acid of interest may be used in plasmid vector constructs, including but not limited to a to cytomegalovirus (CMV) promoter, a Rous Sarcoma (RSV) promoter, a Murine Leukemia (MLV) promoter, a herpes simplex virus (HSV) promoter, such as HSV-tk, a β-actin promoter, as well as any additional tissue specific or signal specific regulatory sequence that induces expression in the target cell or tissue of interest. A signal specific promoter fragment includes but is not limited to a promoter fragment responsive to TNF.

In one such embodiment, a DNA sequence encoding human iNOS is subcloned into the DNA plasmid expression vector, pCIS (Genentech), resulting in pCIS-iNOS. pCIS is a standard mammalian expression vector, containing an antibiotic resistance gene for propagation in *E. coli* and a CMV promoter active in mammalian cells. Such a construct, which may be constructed by one of ordinary skill with components available from numerous sources, will drive expression of an iNOS DNA fragment ligated downstream of the CMV promoter subsequent to transfection of the target cell. More specifically, a NotI/XhoI restriction fragment containing the human iNOS coding region is generated and isolated from pHINOS (pHINOS is deposited with the ATCC with accession number 75358) and ligated into NotI/XhoI digested pCIS. Alternatively, the isolated human iNOS sequence may be fused to any portion of the wild type human iNOS promoter sequence such that expression of human iNOS can be induced within the target cell.

In a preferred embodiment utilizing plasmid DNA to transfect target cells, a plasmid vector comprising a DNA sequence encoding iNOS or a biologically active fragment thereof will be utilized in liposome-mediated transfection of the target cell choice as described within this specification. The stability of liposomes, coupled with the impermeable nature of these vesicles, makes them useful vehicles for the delivery of therapeutic DNA sequences (for a review, see Mannino and Gould-Forgerite, 1988, BioTechniques 6(7): 682–690). Liposomes are known to be absorbed by many cell types by fusion. In one embodiment, a cationic liposome containing cationic cholesterol derivatives, such as SF-chol or DC-chol, may be utilized. The DC-chol molecule includes a tertiary amino group, a medium length spacer arm and a carbamoyl linker bond as described by Gao and Huang (1991, Biochem. Biophys. Res. Comm. 179: 280–285). As an example, but not a limitation, the pCIS-iNOS plasmid construction can be utilized in liposome-mediated in vitro transfection of cultured endothelial cells as well as in situ transfection of endothelial cells.

In another embodiment regarding the use of liposome technology, the viral or nonviral based vector comprising the DNA sequence encoding a biologically active iNOS protein fragment is delivered to the target cell by transfection of the target cell with lipofectamine (Bethesda Research Laboratory). Lipofectamine is a 3:1 Liposome formulation of the polycationic lipid 2,3 dioleyloxy-N-[2 (sperminecarboxgmido)ethyl]- N,N-dimethyl-1-propanaminiumtric fluroacetate (DOPSA) and the neutral lipid dioleoly-phosphatidylethanolamine (DOPE).

Other uses of non-viral modes of gene delivery include, but are not limited to, (a) direct injection of naked DNA; (b) calcium phosphate $[Ca_3(PO_4)_2]$ mediated cell transfection; (c) mammalian host cell transfection by electroporation; (d) DEAE-dextran mediated cell transfection; (e) polybrene mediated delivery; (f) protoplast fusion; (g) microinjection; and (h) polylysine mediated transformation and the genetically engineered cells transferred back to the mammalian host.

The present specification discloses preferred methods of gene therapy-based increase in local human iNOS expression within a targeted region of an artery or within a synthetic conduit utilized to bypass a diseased segment of the arterial vessel.

For example, a preferred method involves in vitro targeting of cultured endothelial cells, vascular smooth muscle cells or a combination of both cell types with a human iNOS DNA fragment ligated into a retroviral vector, such as MFG. A preferred retroviral construct is MFG-iNOS. Such a retroviral vector is transfected into an appropriate packaging cell line to generate infectious virus which is then used to infect endothelial cells, vascular smooth muscle cells or a combination of both cell types in vitro. Once a diseased arterial vessel is substantially cleared of a stenosis or occlusion, the iNOS-infected endothelial and/or vascular smooth muscle cells may be used to repopulate a region of the diseased arterial wall. It will be known to the skilled vascular surgeon that various endovascular surgical techniques are available, depending upon the severity of the occlusion and location of the diseased arterial vessel (for a review, see generally Ahn, 1993, "Endovascular Surgery", in Vascular Surgery, A Comprehensive Review, Ed. W. S. Moore, W. B. Saunders & Co., Philadelphia). For example, such endovascular surgical procedures include but are not limited to balloon angioplasty, laser-assisted balloon angioplasty, double balloon catheterization, mechanical endarterectomy and vascular endoscopy. In addition, a preferred means of physically separating the diseased area of the arterial vessel for delivery of iNOS-expressing cells would be the use of a double balloon catheter.

Preferred modes of in vitro infection of arterial lumina/ cells include human iNOS-containing recombinant retrovirus, especially MFG-iNOS; liposome-mediated transfection of a recombinant iNOS-containing plasmid vector, especially pCIS-iNOS, a recombinant adenovirus vector or a recombinant adeno-associated virus vector. It will be understood to the skilled artisan that similar in vitro infection or transfection procedures may be utilized whether the target cell is an endothelial cell or a vascular smooth muscle cell.

An additional method directing increased local iNOS expression at specific sites within an artery involves iNOS-containing recombinant viral infection of endothelial cells, vascular smooth muscle cells or a combination of both in situ. As discussed in the previous paragraph, this method involves substantially clearing a stenosis or occluded region of said arterial vessel and physically segregating the cleared region of said arterial vessel so as to act as a receptacle for recombinant iNOS viral particles. Again, the preferred manner of clearing a stenosis include but are not limited to balloon angioplasty, laser-assisted balloon angioplasty, mechanical endarterectomy and vascular endoscopy. Additionally, a preferred means of physically separating the manipulated segment of the arterial vessel for delivery of recombinant iNOS-viral particles would be the use of a double balloon catheter.

Preferred modes of in situ infection of arterial luminal cells include iNOS-containing recombinant viral particles, especially MFG-iNOS; liposome-mediated transfection of a recombinant iNOS-containing plasmid vector, especially pCIS-iNOS, a recombinant adenovirus vector or a recombinant adeno-associated virus vector. Both endothelial and vascular smooth muscle cells may be infected or transfected simultaneously through in situ procedures, exemplified but not limited to the in situ procedure outlined in Example Section 13.1.2.

Additional preferred methods of iNOS based gene therapy treatment of vascular disease involves vascular surgery. More specifically, vascular surgical procedures characterized by:

(1) Infecting or transfecting in vitro cultured mammalian cells selected from the group consisting of endothelial cells, vascular smooth muscle cells or a combination of both cell types with a human iNOS-containing viral or non-viral vector encoding a biologically active iNOS protein or protein fragment; seeding a synthetic or autogenous conduit with a population of the human iNOS-transfected cells; and forming a proximal and a distal anastomosis which bypass a diseased arterial vessel segment within said patient. iNOS-based gene therapy combined with vascular bypass techniques will promote expression of iNOS within the graft, resulting in prophylactic and therapeutic relief by preventing or substantially reducing intimal hyperplasia, thrombogenicity, and other forms of post-operative occlusive complications which commonly occur following vascular bypass procedures.

(2) Infecting or transfecting in vitro cultured endothelial cells, vascular smooth muscle cells or a combination of both with recombinant human iNOS; forming a proximal and a distal anastomosis to bypass a diseased portion of an arterial vessel within said patient; physically segregating each anastomosis subsequent to graft suturing; and seeding the isolated area at and around the distal and the proximal anastomoses with arterial cells infected or transfected with a human iNOS construct to promote increased local iNOS expression within the proximity of the anastomoses.

(3) Forming a proximal and a distal anastomosis to bypass a diseased portion of an arterial vessel within the patient; physically isolating each said anastomosis subsequent to graft suturing; and transfecting cells in situ (endothelial, smooth muscle or both) which line the arterial lumen around the target anastomosis with a human iNOS construct such that localized expression of iNOS imparts prophylactic and therapeutic relief from said human vascular disease and from the development of intimal hyperplasia.

(4) Surgically opening an arterial vessel at a site of luminal narrowing or occlusion and performing endarterectomy to reestablish patency; following closure of this site of repair, this site of surgical injury can be seeded with cultured endothelial cells or vascular smooth muscle cells carrying a human iNOS construct to increase local iNOS expression to prevent reocclusion.

(5) Surgically opening an arterial vessel at a site of luminal narrowing or occlusion and performing endarterectomy to reestablish patency; following closure of this site of repair, this site of surgical injury can be seeded by any of the in situ methods disclosed in this specification or any other in situ technique available to the skilled The preferred means of physically separating the proximal and/or distal anastomosis will be use of a double balloon catheter.

The preferred means of seeding vascular grafts include endothelial and vascular smooth muscle cells infected or transfected with iNOS-containing recombinant viral particles, preferably a recombinant retroviral particle and especially an MoMLV retroviral particle such as MFG-iNOS; liposome-mediated transfection of a recombinant iNOS-construct, especially pCIS-iNOS, and adenovirus or adeno-associated virus based vector iNOS constructs (either directly as a viral supernatant or via liposome-mediated transfection of the arterial cells).

This specification discloses to the skilled artisan use of any conduit available to the vascular surgeon in classical bypass procedures in the iNOS-based gene therapy procedures described herein. The present invention envisions the use of numerous conduits, including but not limited to venous autografts, (especially the saphenous vein), synthetic grafts (especially polytetrafluoroethylene [PTFE]), arterial autografts, umbilical vein autografts, and xenografts.

5.2.2. Biologic Therapy by Promotion of Antitumor Effects

The L-arginine:NO pathway has been shown to be involved in antitumor activity (Hibbs, et al., 1987, Science 235: 473–476; Kilbourn, et al., 1990, Proc. Natl. Acad. Sci. USA 87: 3629–3632). The biological activity of nitric oxide is thought to include inhibition of DNA synthesis and mitochondrial enzymes involved in respiration.

The present invention discloses methods of human iNOS-directed gene therapy to promote antitumor effects in cancer patients. Such a human iNOS-directed cancer gene therapy will provide a local increase in nitric oxide concentration within the area of the tumor to be treated, thus promoting antitumor activity without systemic increases in nitric oxide levels.

Therefore, the present invention discloses targeting of a DNA sequence to specific sites within a patient such that local expression of iNOS will lead to increased nitric oxide concentration, thus stimulating antitumor activity.

The isolated human iNOS DNA sequence may be manipulated in vitro in a number of ways available to one of ordinary skill in the art so as to promote local expression of recombinant iNOS or a biologically active fragment thereof.

The human iNOS DNA sequence encoding the intact iNOS protein or a partial DNA sequence thereof encoding a biologically active fragment thereof will be delivered to the target cell by in vitro transduction utilizing the viral and non-viral methods discussed in Section 5.2.1. The in vitro transduced target cell is then introduced into the patient so as to promote local iNOS expression at the tumor site. Therefore, it will be understood that any human iNOS DNA sequence, regardless of tissue source, is a candidate for cancer gene therapy. Such an iNOS DNA sequence may include, but is not limited to, (1) an isolated cDNA or genomic sequence purified from human hepatocyte cells, or a DNA sequence from said source which encodes a biologically active fragment of human iNOS; or (2) an isolated cDNA or genomic fragment purified from a human non-hepatocyte source, or a DNA sequence from said source which encodes a biologically active fragment of human iNOS.

Any of the above-identified iNOS sequences may be fused to a tissue specific or signal specific promoter fragment active within the target cell, or alternatively, may be fused to the wild type human iNOS promoter sequence. An example of a signal specific promoter in iNOS-driven biologic therapy applications would include, but is not limited to, a promoter upregulated in response to TNF. Therefore, any promoter or enhancer sequence which increases the local expression of iNOS within the transformed target cell is a candidate for use in antitumor applications.

Promotion of local expression of iNOS at or around the tumor site is dependent on utilizing an appropriate target cell for in vitro transduction and introduction into the patient. In one embodiment regarding cancer gene therapy, the patient is intravenously injected with in vitro transduced target cells, including but not limited to tumor infiltrating lymphocytes originally harvested from the patient.

The delivery to the target cell may be accomplished by viral or non-viral methods primarily as described in Section 5.2.1. These methods include, but are not limited to (a) retroviral vectors, including but not limited to vectors derived from Moloney murine leukemia virus (MoMLV); Co) adeno-associated vectors; (c) adenovirus vectors; (d) herpes simplex virus vectors; (e) SV40 vectors; (f) polyoma virus vectors; (g) papilloma virus vectors; (h) picornavirus vectors; and (i) vaccinia virus vectors. Depending on the vector system chosen, techniques available to the skilled artisan are utilized to infect the target cell of choice with the recombinant virus vector.

In a preferred method of delivering a human iNOS sequence to the target cell of interest, a recombinant retroviral vector carrying a DNA sequence encoding iNOS or a biologically active fragment thereof is utilized to infect tumor infiltrating lymphocytes. These infected tumor infiltrating lymphocytes are then reintroduced into the patient to promote local production of nitric oxide at the tumor site.

Any number of retroviral constructs which express a biologically active form of iNOS may be utilized to promote antitumor activity. Preferably, MFG-iNOS or DFG-iNOS-Neo may be utilized to infect cultured tumor infiltrating lymphocytes or tumor cells harvested from the patient.

One of ordinary skill in the art will understand that any additional isolated DNA sequence encoding a biologically active portion of iNOS, as hereinbefore disclosed, may be subcloned into a retroviral vector for eventual in vitro infection of cultured tumor infiltrating lymphocytes or tumor cells harvested from the patient.

In addition to the hereinbefore described use of viral vectors to infect target cells, any known non-viral vector that is capable of expression upon transfection of a specified eukaryotic target cell may be utilized to practice the present invention. Such non-viral vectors include, but are not solely limited to, plasmid DNA.

One of ordinary skill in the art will be guided by the literature to choose an appropriate plasmid vector for use in the present invention. Any eukaryotic promoter and/or enhancer sequence available to the skilled artisan which is known to control expression of the nucleic acid of interest may be used in plasmid vector constructs, including but not limited to a cytomegalovirus (CMV) promoter, a Rous Sarcoma (RSV) promoter, a Murine Leukemia (MLV) promoter, a β-actin promoter, as well as any additional tissue specific or signal specific regulatory sequence that induces expression in the target cell or tissue of interest. In a specific embodiment of the invention, the plasmid vector comprising an iNOS DNA sequence is pCIS-iNOS.

Delivery of iNOS-plasmid constructs to a target cell type, such as tumor cells, may be accomplished by numerous biologic and non-biologic carriers available to one of ordinary skill in the art. In a preferred embodiment utilizing plasmid DNA to transfect target cells, a plasmid vector comprising a DNA sequence encoding iNOS or a biologically active fragment thereof will be utilized in liposome-mediated transfection, as described in detail in Section 5.2.1.

Other uses of non-viral modes of gene delivery include, but are not limited to, (a) direct injection of naked DNA; (b) calcium phosphate $[Ca_3(PO_4)_2]$ mediated cell transfection; (c) mammalian host cell transfection by electroporation; (d) DEAE-dextran mediated cell transfection; (e) polybrene mediated delivery; (f) protoplast fusion; (g) microinjection; and (h) polylysine mediated transformation; and the genetically transformed cells then transferred back to the mammalian host.

5.2.3. Biologic Therapy for Treating Microbial Infections

The human iNOS DNA sequences of the present invention may be utilized in treating microbial infections. Specifically, iNOS-driven biologic therapy will be utilized to treat microbes known to be susceptible to increased concentrations of nitric oxide. Nitric oxide is known to be a cytotoxic effector molecule against mycobacteria, helminths, fungi protozoa, and viruses.

Upon review of this specification, the artisan of ordinary skill will be directed to utilize any of the iNOS sequences listed in Section 5.2.1. iNOS-driven antimicrobial therapy is dependant on targeting the respective human iNOS sequence to the tissue-specific cell type harboring the microbe or to the microbe itself. Depending upon the targeted microbe or cell type, delivery of the human iNOS DNA may be accomplished by biologic or non-biologic means.

In a preferred embodiment of utilizing iNOS-driven antimicrobial therapy, the target cells are human hepatocytes infected with the sporozoa *Plasmodium*, the causative agent of malaria. Human malaria is caused by one of four species of *Plasmodium: P. falciparum, P. malariae, P. vivax* and *P. ovale*. The sporocytes of *Plasmodium* penetrate hepatocyte cells subsequent to entry into the circulatory system of the human host.

In a preferred embodiment of treating malaria via iNOS-driven biologic therapy, the iNOS-vector is delivered via liposome mediated transformation of the target hepatocytes.

In another embodiment of the invention, iNOS driven antimicrobial therapy is utilized to treat helminthic infections, including but not solely limited to Schistosomiasis (e.g., *Schistosoma mansomi, Schistosoma haematobium,* and *Schistosoma japonicum.* Direct treatment of helminth infected liver cells encompass all techniques described above for iNOS driven therapy of malaria.

In an especially preferred embodiment of treating malaria via iNOS-driven antimicrobial therapy, the liposomes are modified by insertion of an hepatocyte specific asialoprotein into the liposome complex. The resulting asialoprotein binds to the galactose receptor unique to hepatocytes (see Wall, et. al., 1980, Cell 21: 79–83). Therefore, encapsulating the iNOS DNA vector within an asialoprotein-containing liposome will direct delivery specifically to hepatocytes.

Another embodiment of utilizing iNOS-vectors in antimicrobial therapy involves treatment of lung borne microbial infections, including but not limited to tuberculosis and leprosy.

The causative agent of tuberculosis is *Mycobacterium tuberculosis*, which enters the lung via droplet nuclei and the respiratory route. Once in the lungs, this bacterium grows and eventually is surrounded by lymphocytes, macrophages and connective tissue, forming nodules called tubercles. Normally, this represents the end stage of the infection, with no ill effects. Alternatively, a caseous lesion may form, which may calcify to form a Ghon complex and further become liquified, forming tuberculous cavities.

A preferred treatment of tuberculosis by iNOS-driven antimicrobial therapy involves directing an iNOS vector to the target tissue by viral mediated transformation of cells within the target tissue.

One preferred method of viral mediated delivery is retroviral mediated delivery, as discussed in Section 5.2.1. With the aid of this specification, it is within the realm of the artisan of ordinary skill to construct an iNOS vector for use in treating tuberculosis.

Another preferred method of viral mediated delivery is adenovirus mediated delivery, wherein the iNOS DNA fragment of interest is inserted into an adenovirus vector.

A preferred method of administering iNOS-retroviral or iNOS-adenoviral vectors to invected regions of lung is inhalational administration, in the form of an aerosol mist.

The target would be advanced disseminated disease including but not limited to the treatment of tuberculosis, as well as other microbial infections such as fungal infections in a transplant patient, and disseminated aspergillosis or fungal or additional viral infections such as cytomegalovirus in an AIDS patient.

The causative agent of leprosy is *Mycobacterium leprae*. Transmission of leprosy is highest when children are exposed to infected individuals shedding *M. leprae*. Nasal secretions are the most likely infectious material within family contacts. The preferred mode of iNOS viral delivery is through inhalational administration, as described for *M. tuberculosis*, is also the preferred mode of treating *M. leprae*.

6. EXAMPLE: INDUCING HUMAN HEPATOCYTE INDUCIBLE NITRIC OXIDE SYNTHASE iNOS mRNA is weakly induced in hepatocytes following stimulation with individual cytokines such as for example tumor necrosis factor (TNF), interleukin-1 (IL-1) or interleukin-gamma (IFN-g). Cytokines can synergize to further up-regulate iNOS mRNA levels and nitric oxide synthase activity. Maximum induction of iNOS was achieved with a combination of TNF, IL-1, IFN-g and bacterial lipopolysaccharide (LPS). (Geller, et al., 1993, Proc. Natl. Acad. Sci. 90: 522–526; Nussler, et al., 1992, J. Exp. Med. 176:261–264).

7. EXAMPLE: IDENTIFYING AND ISOLATING HUMAN HEPATOCYTE NITRIC OXIDE SYNTHASE mRNA

A cross-species iNOS cDNA probe capable of hybridizing with human hepatocyte inducible nitric oxide synthase mRNA was used to identify and isolate the mRNA for human hepatocyte inducible nitric oxide synthase. The time-point of peak iNOS mRNA levels following cytokine and LPS [hereinafter cytokine mixture (CM)] stimulation was then determined.

Total cellular RNA was extracted 2–48 hours following CM-stimulation of cultured human hepatocytes using the RNAzol B modified method of Chomczynski and Sacchi (1987, Anal. Biochem. 162: 156–159). 20 microgram aliquots of total RNA were examined by Northern blot analysis through cross-species hybridization with a murine macrophage iNOS cDNA probe generated from a fragment of the murine iNOS cDNA isolated after NotI restriction enzyme digest. (Lowenstein, et al., 1992, Proc. Nat. Acad. Sci. USA. 89:6711–6715; GenBank Accession No. M92649). The presence of human hepatocyte nitric oxide synthase mRNA was identified as a single band of about 4.5 Kb size with maximal iNOS mRNA levels seen about 8 hours after CM stimulation.

Figure 1:
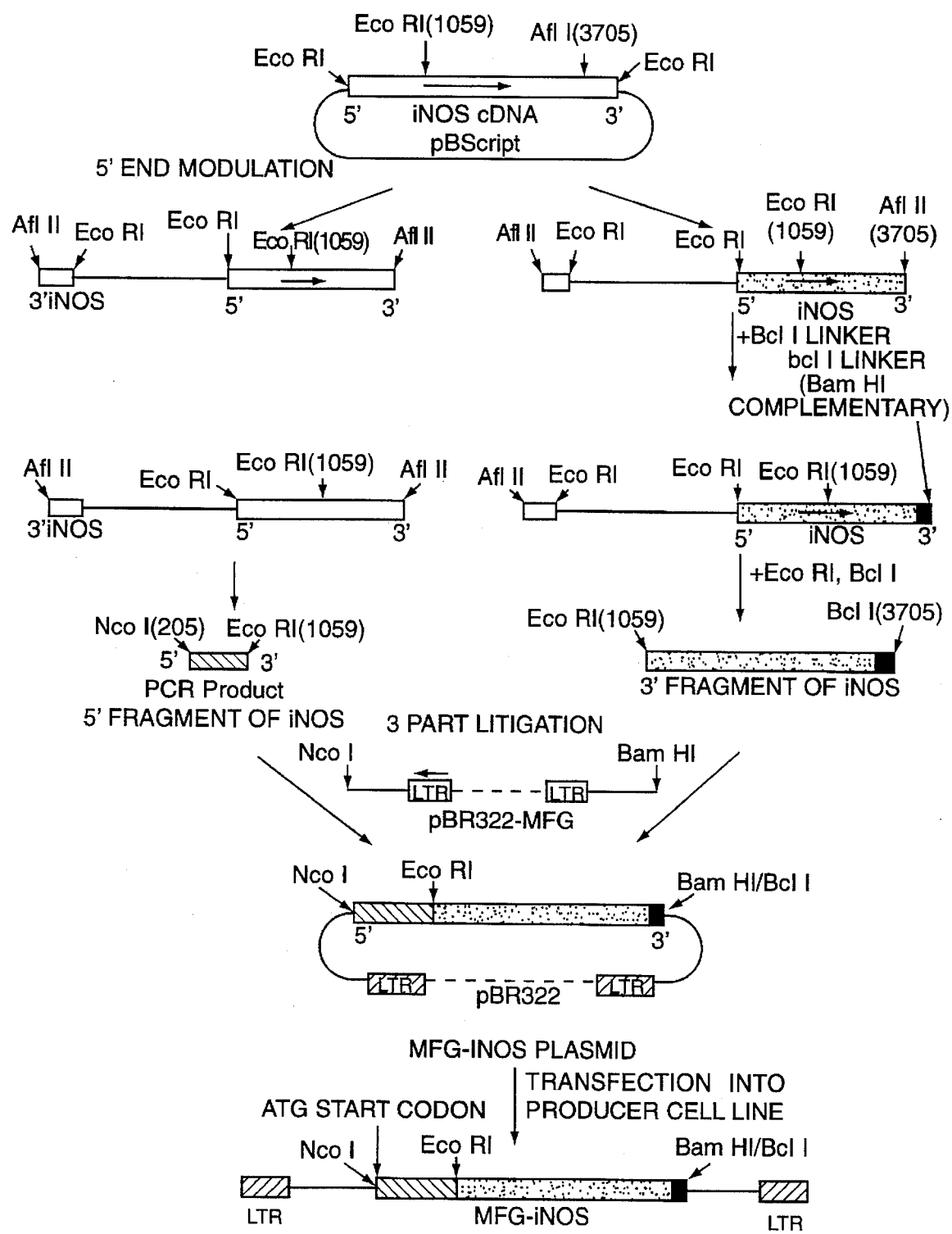
Figure 2:
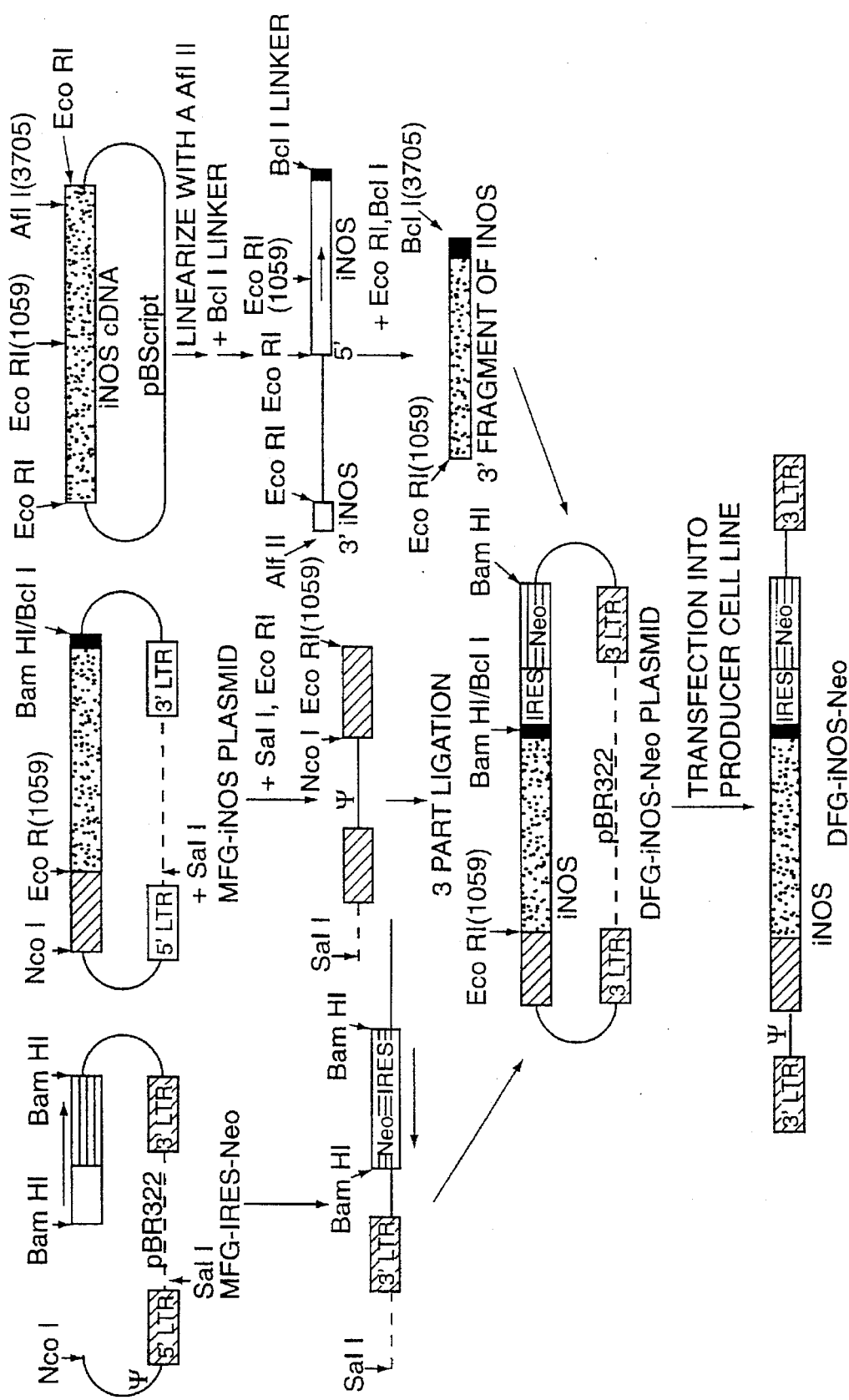
FIG. 2 shows a Northern blot of a mouse macrophage NOS cDNA cross-hybridizing to human hepatocyte (HC) nitric oxide synthase mRNA.
Figure 3:
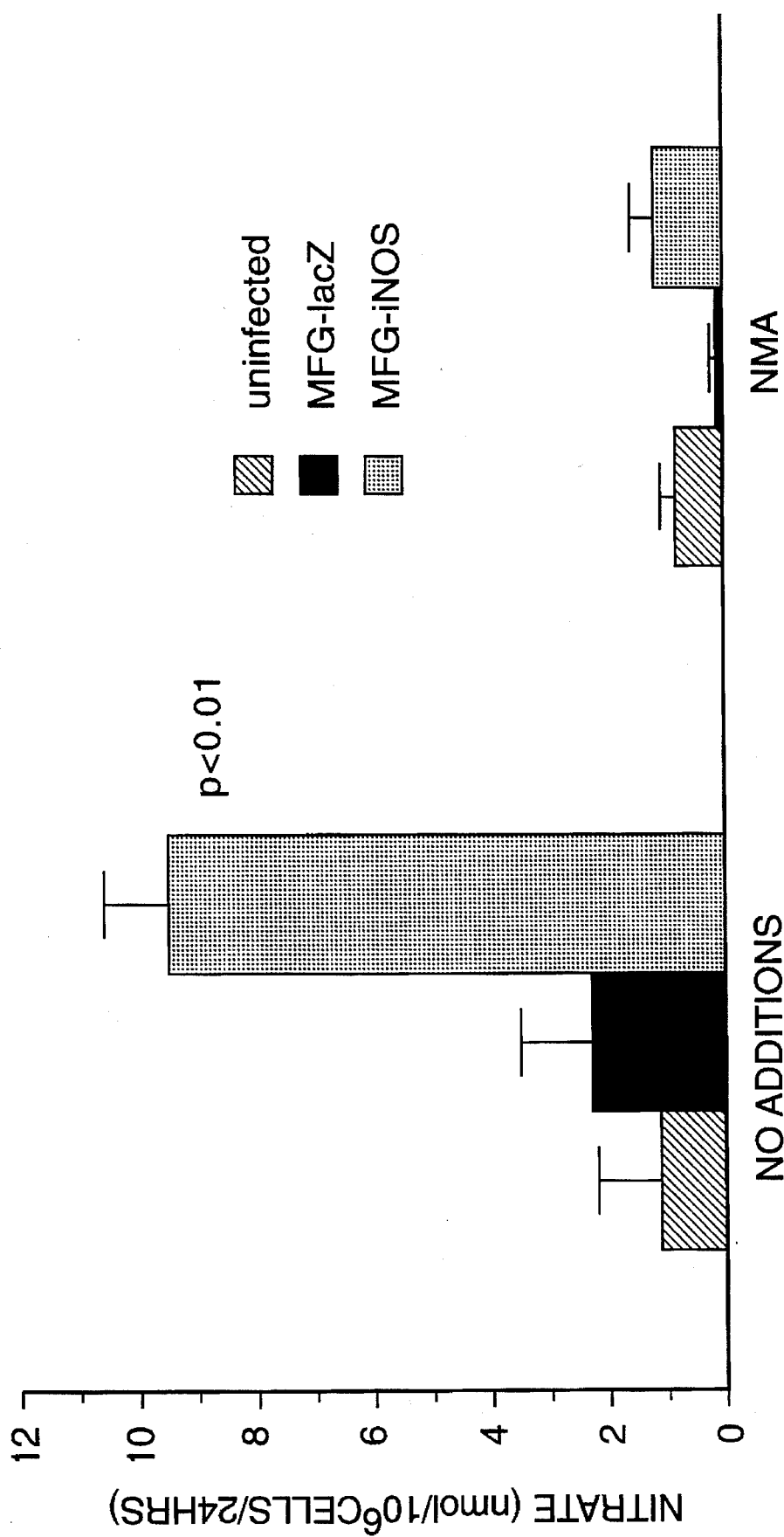
FIG. 3 shows a Northern blot of induced nitric oxide synthase mRNA isolated from three separate human liver samples using mouse macrophage cDNA.

FIG. 2 shows the presence of the 4.5 kb message for human hepatocyte inducible nitric oxide synthase. Freshly isolated human hepatocytes (HC) were placed in cell culture and exposed to a combination of human recombinant tumor necrosis factor (500 units/milliliter), human recombinant interleukin-1 (5 units/milliliter), human recombinant interferon-gamma (100 units/milliliter), and lipopolysaccharide (10 micrograms/milliliter). FIG. 2 shows that total RNA was isolated at the indicated time points (2, 4, 6, & 8 hrs.) and 20 micrograms per sample was subjected to Northern blot analysis. A 2.7 Kb cDNA fragments for murine macrophage inducible nitric oxide synthase was used to identify the human hepatocyte inducible nitric oxide synthase mRNA. FIG. 2 demonstrates that the 4.5 Kb message level peaked at about 8 hours following stimulation. FIG. 2 shows that no mKNA signal was detected in control (unstimulated) hepatocytes. FIG. 3 shows the expression of the 4.5 Kb human hepatocyte inducible nitric oxide synthase mRNA at about 8 hours after exposure to the above mentioned cytokines from hepatocytes isolated from three separate individuals [patent (Pt.) 1, 2, and 3]. FIG. 3 demonstrates that no signal was detected in control (unstimulated) hepatocytes.

Figure 4:
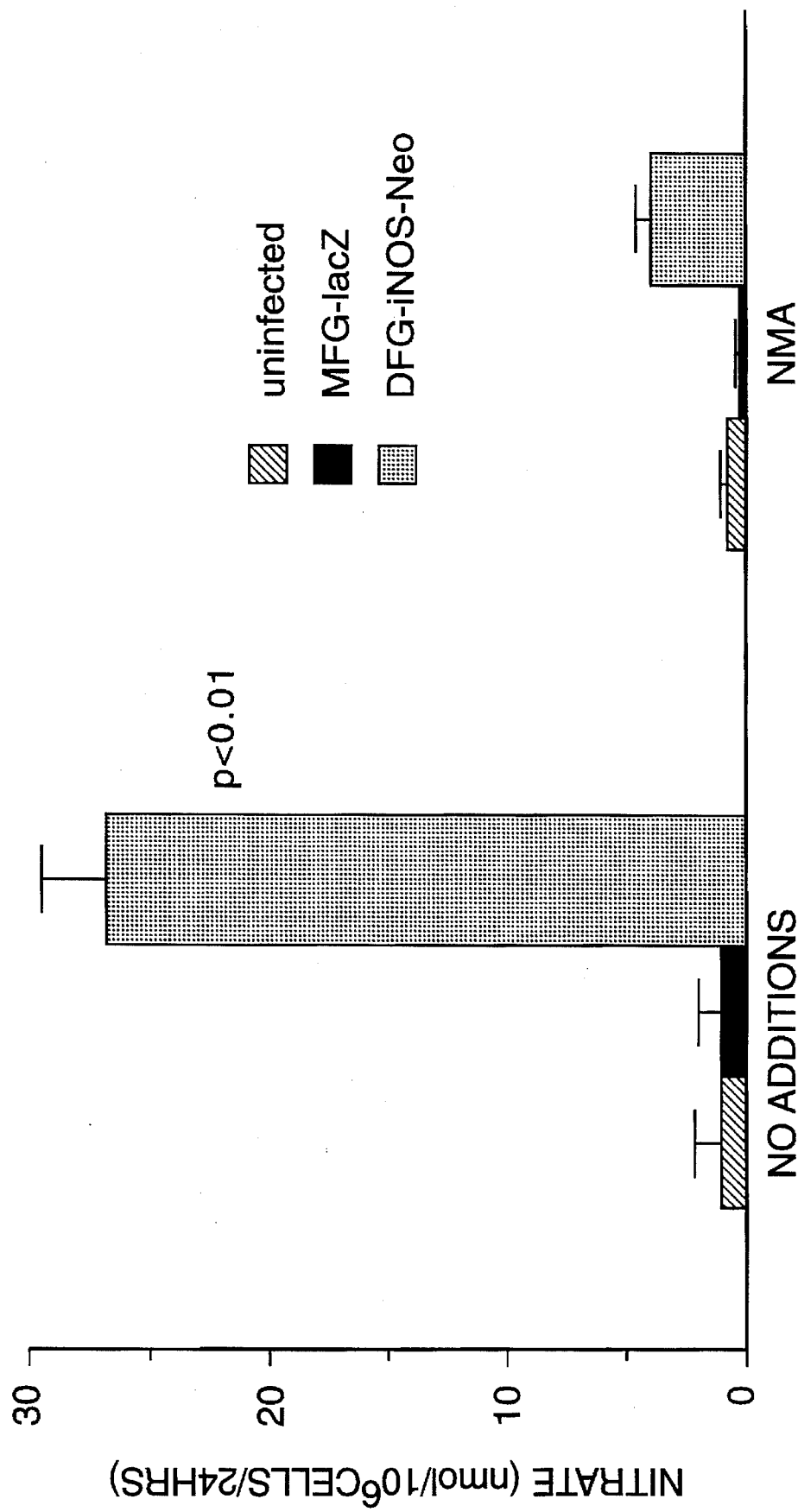
FIG. 4 shows a Northern blot of poly A mRNA purified from 2 separate human liver samples used in the construction of the cDNA library for isolation of the cDNA clone for the human hepatocyte inducible nitric oxide synthase.

Because the 8 hour time point yielded maximal iNOS mRNA levels, total cellular RNA was isolated from two human livers about 8 hours following CM-stimulation in vitro. cDNA synthesis requires about 10 to 20 micrograms of poly A mRNA rather than total RNA. Poly A mRNA was purified from total cellular RNA by elution through an oligo-dT cellulose column. To identify the presence of human hepatocyte iNOS mRNA in the purified poly A mRNA, repeat Northern blot analysis was performed on 0.5 micrograms of purified A mRNA from each of the two human livers using the 2.7 Kb cDNA probe for murine macrophage inducible nitric oxide synthase. FIG. 4 shows strong nitric oxide synthase mRNA bands from the 2 different patients without evidence of degraded poly A RNA.

FIG. 4 shows that the murine macrophage inducible nitric oxide synthase cDNA probe effectively cross hybridizes and identifies the human hepatocyte inducible nitric oxide synthase mRNA in the poly A RNA. The samples of poly A mRNA from the 2 patients were pooled and were used to construct the cDNA library for isolation of cDNA clone for the human hepatocyte inducible nitric oxide synthase.

8. EXAMPLE: CONSTRUCTING A HUMAN HEPATOCYTE INDUCIBLE NITRIC OXIDE SYNTHASE cDNA LIBRARY

Using about 20 micrograms of the poly A mRNA isolated from CM-stimulated human hepatocytes, a cDNA library was constructed by Stratagene, La Lolla, Calif. The first strand cDNA was synthesized from the human hepatocyte poly A mKNA using MoMLV reverse transcriptase enzyme with oligo-dT primers. After excluding strands less that 1000 nucleotide basis pairs in length, the cDNA's were inserted into a lambda Zap II phage vector (Stratagene, La Jolla, Calif.) and was titered.

9. EXAMPLE: SCREENING THE cDNA LIBRARY FOR HUMAN HEPATOCYTE INDUCIBLE NITRIC OXIDE SYNTHASE cDNA CLONES

Figure 5:
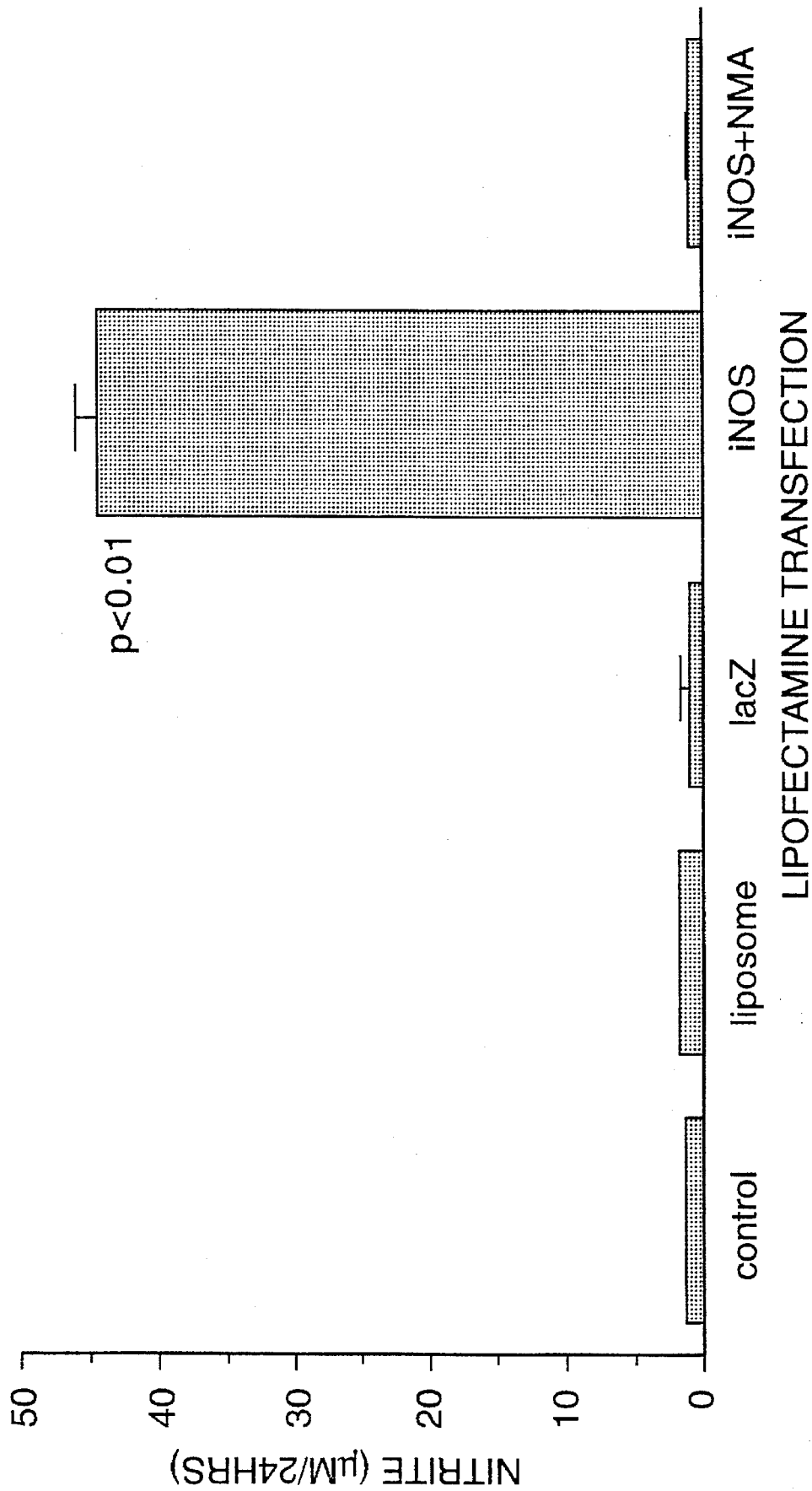
FIG. 5 shows a Northern blot using cDNA isolated from human hepatocytes that sets forth the time course of induction of human nitric oxide synthase mRNA following cytokine and LPS stimulation.
Figure 3:
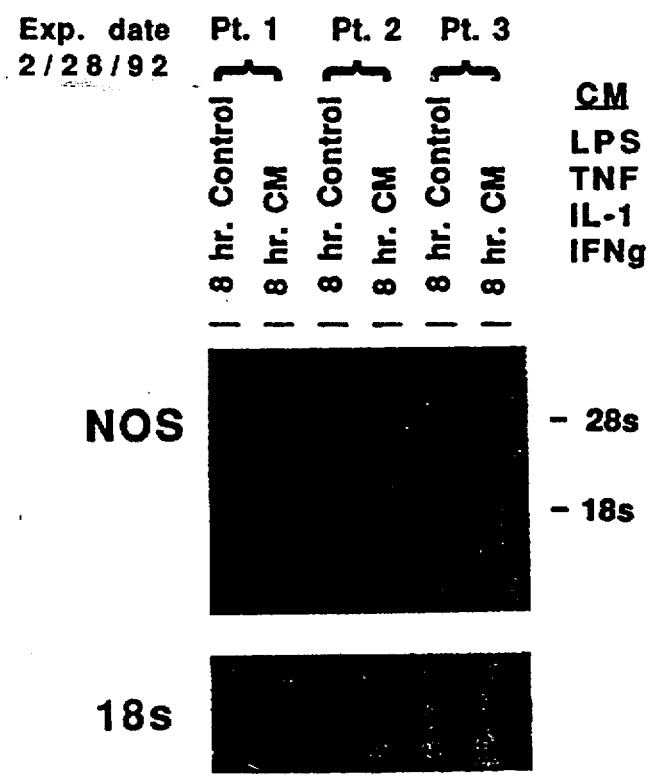
Figure 4:
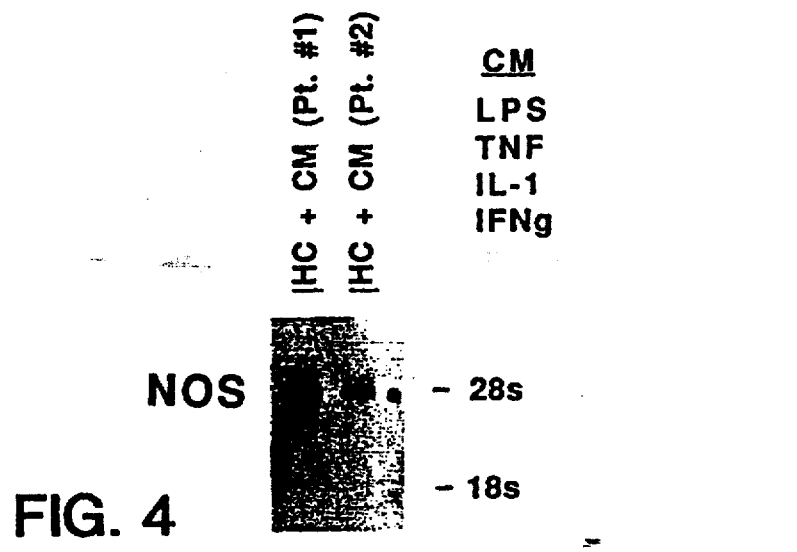
Figure 5:
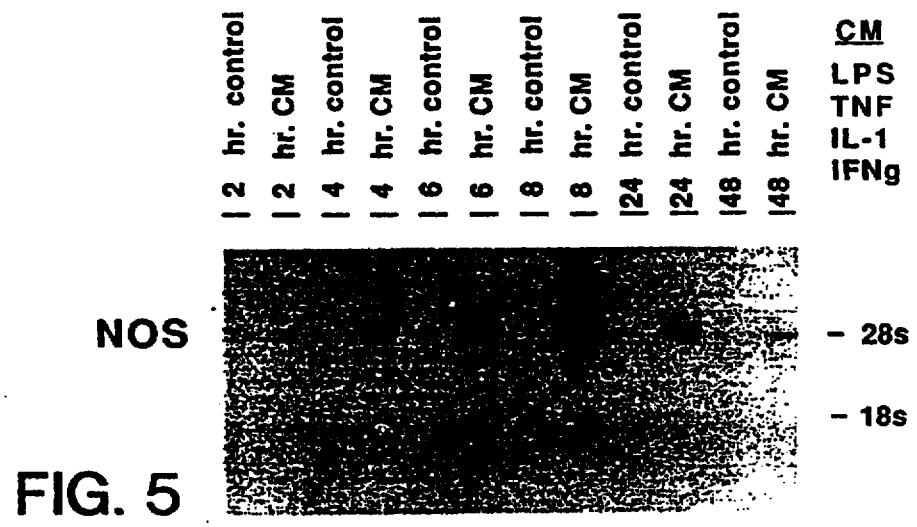

To screen the cDNA library, $1\times10^6$ phage were incubated with bacteria (E. coli Sure strain) at 34 to 40 degrees centigrade for 15 to 30 minutes. This mixture was added to molten agarose and poured onto 20×20 centimeter agar plates at a density of $2\times10^5$ plaques/plate (Maniatis et al., 1982, Molecular Cloning: A Laboratory Manual, Cold Spring Harbor Laboratory, Cold Spring Harbor, N.Y.,). The plates were incubated at 34 to 40 degrees centigrade overnight for 6 to 24 hours to allow for phage lysis of bacteria. The plaques were then transferred to nitrocellulose filters and clones carrying iNOS cDNA inserts were identified by filter hybridization with $^{32}$P-labeled murine macrophage inducible nitric oxide synthase cDNA probe. Positively labeled clones were cored from the agar plates after localization by autoradiograph alignment. The positive clones were rescued from the lambda Zap II phage vector with the helper phage ExAssist (Stratagene, La Jolla, Calif.), and then converted to plasmid vectors using pBluescript (Stratagene, La Jolla, Calif.). The cDNAs for human hepatocyte inducible nitric oxide synthase were excised from the Bluescript plasmid cloning sites by restriction with EcoRI enzyme and then sized by gel electrophoresis to identify a full-length clone. The cDNA identities were confirmed by DNA sequencing and by Southern blot hybridization with the murine macrophage iNOS cDNA probe. In addition, Northern blot analysis of cytokinestimulated human hepatocyte poly A mRNA was performed using the full-length human inducible nitric oxide synthase cDNA clone of this invention as the probe. FIG. 5 shows a time course for the expression of human hepatocyte inducible nitric oxide synthase mRNA. This RNA was isolated from a patient different from the patients listed in FIGS. 2 and 3. The cells of the patient in FIG. 5 were exposed to the same agents as described for FIG. 2. FIG. 5 shows the cloned human inducible nitric oxide synthase cDNA identifies the same size mRNA signal as the murine macrophage iNOS cDNA probe, thus, further confirming its identify. It is important to note that the isolated cDNA clone coding for human inducible nitric oxide synthase of this invention can hybridize with human inducible nitric oxide synthase mRNA, thus, confirming the capacity of the cDNA clone of this invention to identify the human hepatocyte inducible nitric oxide synthase mRNA.

10. EXAMPLE: CDNA SEQUENCING

The plasmid vector pBluescript contains universal primer regions which were used to facilitate double-stranded DNA sequencing. Positive clones were sequenced by using the dideoxynucleotide technique of Sanger, supra, with the Genesis 2000 sequencing system (USB, Cleveland, Ohio). Sequence analysis was done using Genbank DNA sequencing software programs available through the Pittsburgh Supercomputing Center (Billiar TR., Pittsburgh Supercomputing Center, Pittsburgh, Pa.).

11. EXAMPLE: EXPRESSING HUMAN HEPATOCYTE INDUCIBLE NITRIC OXIDE SYNTHASE

Verification of the full length cDNA identity was accomplished by expressing the recombinant human hepatocyte inducible nitric oxide synthase protein. The human hepatocyte inducible nitric oxide synthase cDNA was ligated into the pCIS expression vector (Genentech, Calif.) which utilizes a CMV promoter. Next the expression vector was transfected into human embryonic kidney 293 cells (ATCC, Md.). Nitric oxide synthase activity was assessed by measuring the conversion of [$^3$H] arginine to [$^3$H] citrulline. It will be appreciated by those skilled in the art that this expression system was successfully used for expression of the cloned rat brain constitutive nitric oxide synthase, and there was negligible nitric oxide synthase activity in the unstimulated 293 kidney cells (Bredt et al., 1991, Nature, 351:714–718). After the identity of the human hepatocyte inducible nitric oxide synthase cDNA clone of this invention was verified as hereinbefore described, the cDNA was expressed in a baculovirus expression system (Invitrogen, San Diego, Calif.) which allowed for large scale enzyme production (1988, Texas Agriculture Experiment Station Bulletin, No. 1555). More specifically, the human hepatocyte nitric oxide synthase cDNA was inserted into the baculovirus transfer vector and then co-transfected with wild type viral DNA into Sf9 insect cells (ATCC, Maryland). Recombinant viral plaques were isolated to allow for protein over-expression.

12. EXAMPLE: PURIFYING THE HUMAN HEPATOCYTE INDUCIBLE NITRIC OXIDE SYNTHASE PROTEIN

The resultant human hepatocyte inducible nitric synthase protein was purified using a two step procedure. First, the protein was passed through an anion-exchange column of DEAE cellulose. This was followed by affinity chromatography with 2', 5'-ADP Sepharose. (Evans et al., 1992, Proc. Natl. Acad. Sci. USA, 89:5361–5365). Purity was assessed by SDS-polyacrylamide gel electrophoresis. Activity was quantitated after each step by measuring the ability of the enzyme to generate $NO_2$— and $NO_3$— from L-arginine. $NO_2$— and $NO_3$— was measured using an automated colorimetric reaction based on the Green reaction (Green, et al., 1982, Anal. Biochem. 126:131–137)

Whereas, particular embodiments of this invention have been described above for purposes of illustration, it will be evident to those persons skilled in the art that numerous variations of the details of the present invention may be

13. EXAMPLE: TREATMENT OF VASCULAR OCCLUSIVE DISEASE

13.1. Materials and Methods

Total RNA extraction, Northern, Southern, Western blots, and PCR are techniques routinely performed by one of ordinary skill in the art (e.g., see generally Maniatis, et al., 1989, Molecular Cloning: A Laboratory Manual, Cold Spring Harbor Laboratory, Cold Spring Harbor, N.Y.; Geller, et al., Proc. Natl. Acad. Sci. USA 90: 522–526; Towbin, et al., 1979, Proc. Natl. Acad. Sci. USA 76: 4350; Brenner, et al., 1989, BioTechniques 7:1096–1103). The direct iNOS enzyme assay measures the conversion of $[^3H]$-arginine to $[^3H]$-citrulline, as described (Bredt, et al., 1991, Nature 351:714–718). $NO_2^- + NO_3^-$ levels are measured in the culture supernatants by an automated procedure based on the Griess reaction (Green, et al., 1982, Anal. Biochem. 126: 131–137). Briefly, immunohistochemistry for iNOS is performed as follows: The cells are washed twice in phosphate buffered saline (PBS), fixed in 2% paraformaldehde in PBS, and permeabilized with 2% paraformaldehyde in PBS containing 0.1% Triton X100. Cells are then incubated for 2 hours with the primary antibody. AntiNOS antibody labeled specimens are then washed and incubated with a biotynylated secondary antibody, washed again and treated with 0.1% hydrogen peroxide. Following additional washes the cells are treated with ABC reagent for 45 minutes, washed, reacted with diaminobenzidme for 5 minutes, and finally washed with $H_2O$ prior to counter staining with toluidine blue.

13.1.1. In Vitro Transfection of Target Cells with A Human iNOS cDNA

Primary porcine endothelial cells, derived from the Yucatan minipig (YPE cells), will be isolated as described by Reitman, et al. (1982, Atherosclerosis 43:119–132) as outlined in Nabel, et al. (1989, Science 244: 1342–1344). Cells are incubated with medium 199 (M199) supplemented with 10% FBS, 2 mM L-glutamine, 50 units/ml penicillin, and 5 ug/ml streptomycin.

Gene transfer to endothelial cells by retroviral-based infection, adeno-associated viral-based infection as well as liposome mediated transfection will be utilized. To exemplify retroviral infection, the retroviral vector is an MFG vector which is utilized to construct MFG-iNOS (see FIG. 6 and FIG. 7). The MFG vector is a simplified MoMVL vector in which the DNA sequences encoding the pol and env proteins have been deleted so as to render it replication defective. The majority of the gag sequence has also been deleted. The human hepatocyte iNOS cDNA was inserted into the NcoI and BamHI cloning sites of the retroviral vector MFG as shown in FIG. 6 and FIG. 7. Briefly, the MFG vector has a unique cloning region consisting of a 5' NcoI site and a 3' BamHI site. PCR primers were used to generate a point mutation at bp 205 of the iNOS cDNA, manufacturing an NcoI site that incorporated the ATG start codon. A 5' fragment of the PCR product of the iNOS cDNA spanning from the NcoI site at bp 205 to the EcoRI site at bp 1059 was isolated. The 3' BamHI site was generated by linearizing the pBScript-iNOS plasmid with AflII which uniquely cut at bp 3705 of the iNOS cDNA. This restriction site is located approximately 40 bp downstream from the iNOS stop codon. A BclII linker was then ligated to the linearized plasmid. Double digestion with EcoRI and BclII allowed the isolation of a 3' fragment of the iNOS cDNA from bp 1060 (EcoRI) to bp 3710 (BclI). The BclI overhang is complementary to the overhang generated by BamHI. A three part ligation was then performed between MFG, the 5' PCR product with the 5' NcoI site, and the 3' fragment with the 3' BclII linker. *Escherichia coli* were transformed with the ligation mixture and grown on ampicillin selection. Transformants were isolated and screened for the properly reconstituted MFG-iNOS construct. One correct transformant was isolated and large scale plasmid DNA preparations performed.

A second retroviral vector construct was also made, this one to include a selectable neomycin resistance marker (see FIG. 6 and FIG. 7.) The MFG retroviral vector had been previously engineered to contain an internal ribosome entry site (IRES) followed by a neomycin resistance gene ($Neo^R$) inserted at the 3' BamHI cloning site of MFG. The IRES sequence allows for the translation of multiple protein products from a single polycistronic mRNA. This MFG-IRES-$Neo^R$ plasmid was digested with the restriction enzymes SalI (which cuts approximately 3000 bps upstream of the NcoI cloning site of MFG) and Bam HI. The larger fragment containing the majority of the MFG backbone attached to IRES and $Neo^R$ was purified. The previously constructed MFG-iNOS vector was also digested with SalI and EcoRI and a 3.7 ICo fragment containing the 5' portion of the iNOS cDNA was isolated. The Y end of the iNOS cDNA was the identical 3' fragment with the BclII linker used to construct MFG-iNOS. A 3 part ligation with MFG-IRES-$Neo^R$, 5' SalI- EcoKl fragment containing the 5' end of the iNOS cDNA, and 3' iNOS cDNA with the BclII linker was performed. The ligation mixture was then transformed into *E. coli* and selected for ampicillin resistant transformants. Such a positive transformant with the correctly oriented construct, referred to throughout this specification as DFG-iNOS-$Neo^R$, was isolated and large scale plasmid preparation performed.

These retrovirus vectors carrying a portion of the human hepatocyte iNOS cDNA are transfected into the CRIP cell packaging line (Danos and Mulligan, 1988, Proc. Nat. Acad. Sci. USA 85: 6460–6464) using a standard calcium phosphate transfection procedure. The viral vector DFG-iNOS-$Neo^R$ is capable of imparting resistance to the synthetic antibiotic G418. CRIP cells transfected with DFG-NOS-Neo were selected on the basis of resistance to G418. The CRIP cell line expresses the three viral proteins required for packaging the recombinant viral RNAs into infectious particles. Moreover, the viral particles produced by the CRIP cell line are able to efficiently infect a wide variety of species of mammalian cells including human cells. All retroviral particles produced by this cell line are defective for replication but retain the ability to stably integrate into mammalian cells, thereby transferring an heritable trait to these cells. Virus stocks produced by this method are substantially free of contaminating helper-virus particles and are also non-pathogenic.

Viral supernatants for both the MFG-iNOS and DFG-iNOS-$Neo^R$ vectors were used to infect endothelial cells in vitro as described by Zwiebel, et al. (1989, Science 249:220–222). Briefly, CRIP producer cells transfected with MFG-iNOS proviral DNA carried no selectable markers. A heterogenous population of CRIP cells, some producing MFG-iNOS virus and some not, was grown and viral supernatants collected to infect endothelial cells. Those CRIP cells transfected with DFG-iNOS-$Neo^R$ carried a selectable marker (resistance to G418) and a GRIP producer line generating high titer MFG-iNOS-Neo viral supernatants was isolated and propagated. Viral supernatants for MFG-iNOS and DFG iNOS-Neo$^R$ were found to be free of these viruses. These viral supernatants are used to infect endothelial cells in vitro and iNOS activity assayed at 48–72 hours after infection as described below (see FIG. 9 and 10).

To determine effective infection, endothelial cell nitric oxide production will be determined by several methods and compared to endothelial cells infected with control viruses. Nitric oxide produced by the intact cells can be quantified by measuring the release of $NO_2^- + NO_3^-$ into the culture medium. FIGS. 9 and 10 demonstrate successful transfer of iNOS function to endothelial cells using both MFG-iNOS and DFG-iNOS-Neo$^R$ vectors as evidenced by increased $NO_2^-$ production in comparison to uninfected and control virus infected endothelial cells. Enzyme activity within the cells can be measured in cytosolic preparations from cultured cells. iNOS can be distinguished from native cNOS by excluding activity in the membrane fraction, where 70–90% of native cNOS is located. The presence of iNOS mRNA will be detected by Northern blot analysis. Based on the human iNOS sequence, a set of human specific PCR primers for iNOS has been designed which do not amplify the endothelial cNOS mRNA. iNOS protein will be sought by Western blot analysis of cytosolic proteins and immunohistochemistry of intact cells (to localize sites of expression within the cell). Previously characterized human and murine iNOS antibodies, as well as a human cNOS antibody will be utilized in Western blot analysis and immunohistochemical techniques. The immunohistochemistry will also allow for an estimation of the efficiency of infection by calculating the percentage of positive staining endothelial cells. The stability of iNOS expression in the endothelial cells will be followed over time through subsequent cell passages. Nitric oxide-induced toxicity will be determined by cellular morphology as well as by $^3$H-thymidine uptake for DNA synthesis. In vitro toxicity encountered due to excessive nitric oxide production can be controlled by adding inhibitors such as $N^G$-monomethyl-L-arginine (NMA), which competitively inhibits the iNOS enzyme but does not effect gene expression. A second technique for limiting any nitric oxide toxicity is the addition of hemoglobin to the cultures. Hemoglobin rapidly binds and deactivates nitric oxide.

Endothelial cell transfection with naked DNA (e.g., including but not limited to a non-viral vector such a plasmid DNA construct) will also be performed so as to promote transient as well as long term expression of the iNOS DNA sequence in the target cell. The iNOS-containing construct is prepared for endothelial cell transfection by forming a DNA-cationic liposome complex as described by Gao and Huang (1991, Biochem. Biophys. Res. Comm. 179: 280–285). The human hepatocyte iNOS cDNA sequence has been subcloned into the pCIS expression vector (Genentech), which utilizes a CMV promoter/enhancer, resulting in high iNOS activity in transient transfection experiments. In addition to the CMV enhancer/promoter sequence of pCIS, sequences downstream of the promoter enhancer fragment of the 5370 bp mammalian expression plasmid include, from 5'-3', a CMV intron, a polylinker sequence for ligation of the DNA fragment of interest, an SV40 polyadenylation site, an SV40 origin of replication, a DHFR cDNA fragment and the β-lactamase cDNA, which imparts ampicillin resistance. As discussed elsewhere in the specification, any number of mammalian expression vectors may be utilized to deliver the iNOS sequence of interest to the target cell. The pCIS-iNOS DNA will be combined with lipofectamine (BRL) at a ratio of 1 µg DNA/10 nmole liposomes and slowly added to endothelial cells. The cells will be incubated for 5 hours in serum-free media, followed by washing and assay for iNOS activity 48 hours later. The lipofectamine reagent has demonstrated approximately a 10% transfection efficiency in cultured murine endothelial cells. As well as promoting transient and long-term expression of iNOS, liposome transfection of vector DNA comprising an iNOS DNA sequence also provides a system for assay of potential nitric oxide toxicity as discussed above.

Any of the above disclosed strategies for targeting endothelial cell populations may be applied to directed transfection or infection of vascular smooth muscle cells. As an example and not intended as a limitation, FIG. 11 depicts results of a pCIS-iNOS/lipofectamine transfection targeting vascular smooth muscle cells. Significant nitrite production is detected for pCIS-iNOS transfected vascular smooth muscle cells in the absence, but not the presence, of $N^G$-monoethylarginine. Additionally, no nitrite production was detected upon transfection with a control plasmid (pSV-lacZ), and a plasmid-less control with or without the addition of liposomes. As discussed throughout the specification, this method of targeting endothelial and/or vascular smooth muscle cells is especially preferred for in situ transfection of target cells lining the arterial lumen.

An additional mode of delivering a DNA sequence encoding iNOS utilizes a hybrid liposome:adeno-associated (AAV) construct. The use of liposome transfection procedures allows the use of an AAV viral vector comprising an iNOS DNA sequence. This recombinant AAV construct is cotransfected into target endothelial cells with a plasmid containing the rep gene of AAV, providing transient expression of the rep protein to enhance stable integration of the recombinant AAV genome into the target cell genome. To distinguish the transfected iNOS from the small amounts of native iNOS that may be expressed by endothelial cells, the iNOS constructs will include a hemagglutinin epitope tag. The epitope tag will be inserted both 5' and 3', and tested for any effects on iNOS activity. An antibody to the hemagglutinin epitope will be used to identify transfected iNOS by methods known to one of ordinary skill in the art.

In one example, but by no means forwarded as a limitation, the CMV promoter-iNOS region of pCIS-iNOS will be ligated between the terminal repeats of AAV. The iNOS-AAV construct will be cotransfected into endothelial cells with a plasmid containing the rep gene of AAV and with lipofectamine (BRL). An assay for iNOS activity will be assayed 48–72 hours later.

Additionally, an AAV-iNOS construct may be utilized to infect target endothelial cells (for a review of using AAV genomes as gene therapy based vectors, see Muzyczka, 1992, Current Topics in Microbiology and Immunology 158: 97–129). In utilizing the recombinant virus alone, human cells containing a helper virus such as adenovirus or herpes virus are transfected with a recombinant AAV plasmid comprising a human hepatocyte iNOS DNA sequence and a non-packaging complementing AAV plasmid which supplies wild type AAV gene products in trans. The recombinant AAV virus (comprising the iNOS DNA sequence) is purified away from contaminating helper virus and is then utilized to infect target endothelial cells.

13.1.2. In Vitro Arterial Cell Manipulation

Yucatan minipigs will be anesthetized with pentobarbital and iliofemoral arteries exposed by sterile technique. A specially designed double balloon catheter (C. R. Bard, Inc.) will be inserted into the iliac artery, partially inflated, and passed to mechanically denude the endothelium, as described in Nabel, et al. (1989, Science 244: 1342–1344). The catheter is repositioned within the denuded segment, proximal and distal balloons are inflated, followed by heparin irrigation and 10 minute instillation of dispase, which removes any remaining endothelial cells. Subsequently, in vitro iNOS-infected endothelial cells ($2 \times 10^6$) will be instilled for 30 minutes, followed by catheter removal, arterial side branch ligation, and wound closure.

As a control, the contralateral iliofemoral artery will be seeded with endothelial cells infected with a control virus. Segments of experimental and control arteries will be removed 2 or 6 weeks later. Immunohistochemistry and iNOS enzyme assay will confirm expression in vivo. Tissue fixation and electron microscopy will be performed to characterize endothelial cell and vascular morphology. Minimal nitric oxide-mediated toxicity to the vasculature and systemically is expected in vivo. Excess nitric oxide which escapes the cells should be scavenged immediately by hemoglobin in circulating red blood cells in the vessel lumen. Endothelial cell function will be confirmed by uptake of acetylated low density lipoprotein, the presence of von Willebrand's factor, and angiotensin converting enzyme activity.

The procedure described in the previous two paragraphs can be performed by substituting in vitro iNOS-infected vascular smooth muscle cells for endothelial cells.

14. EXAMPLE: NOS DIRECTED CANCER THERAPY iNOS-directed cancer therapy may be exemplified by harvesting and selective culture of a patients tumor infiltrating lymphocyte population, transduction by an iNOS containing viral or non-viral vector, followed by reintroduction of the iNOS-transduced cell to the patient. Peripheral blood lymphocytes are removed from the patient and TILs are selected in culture as described in Rosenberg, et al. (1992, Human Gene Therapy 3:57–73, herein incorporated by reference). The TILs will then be utilized as the target cell population for transduction with DFG-iNOS-Neo$^R$. Transduced TILs are selected in G418-supplemented medium and prepared for administration back to the patient by known techniques.

Another method of iNOS-directed therapy for treating cancer is direct delivery of MFG-iNOS to tumor site(s) in liposome capsules. The stability of liposomes, coupled with the impermeable nature of these vesicles makes them useful vehicles for the delivery iNOS containing sequences, such as but not limited to pCIS-iNOS, to the tumor site. Site specific delivery of the liposome capsule to the tumor site is promoted by modification of the liposome membrane to exhibit a tumor specific antibody so as to promote liposome adhesion and fusion only to the tumor cell. Local delivery of a recombinant iNOS vector to the tumor site will result in increased local iNOS expression, increased nitric oxide production and hence, antitumor activity.

pCIS-iNOS liposomes will be formulated into a suitable pharmaceutical carrier for in vivo administration by injection or surgical implant.

15. EXAMPLE: NOS DIRECTED ANTIMICROBIAL TREATMENT

The treatment of microbial infections by increasing local iNOS expression will be exemplified through the treatment of a malarial infection. The recombinant plasmid vector pCIS-NOS will be delivered locally to the liver in liposome capsules. The liposome capsules will be modified to exhibit a liver specific surface ligand. An asialoprotein is a glycoprotein treated to remove sialic acid (i.e., neuraminic acid). The resulting asialoprotein specifically binds to the galactose receptor unique to hepatocytes (see Wall, et. al., 1980, Cell 21: 79–83). Therefore, encapsulating pCIS-iNOS within an asialoprotein-containing liposome will ensure delivery to and local expression of iNOS in hepatocytes only.

The pCIS-iNOS vector incorporated into liposomes will be formulated into a suitable pharmaceutical carrier for in vivo administration by any appropriate route including but not limited to injection, absorption through epithelial or mucocutaneous lining or by a sustained released implant, whether it be a cellular or tissue implant.

16. DEPOSIT OF MICROORGANISMS

The following microorganisms have been deposited by David A. Geller on behalf of the University of Pittsburgh of the Commonwealth System of Higher Education, Pittsburgh, Pa. 15260, USA, on Nov. 18, 1992, with and are available from the permanent collection of the American Type Culture Collection (ATCC), 12301 Parklawn Drive, Rockville, Md. 202852-1776, USA:

ATCC 75358—Human Hepatocyte Inducible Nitric Oxide Synthase cDNA in pBluescript (pHINOS)

ATCC 69126—Human Hepatocyte Inducible Nitric Oxide Synthase cDNA in pBluescript transformed in E. coli SOLR bacteria (plasmid HINOS cDNA)

The American Type Culture Collection has performed viability tests on each of the hereinbefore mentioned deposited microorganisms and has concluded on Nov. 20, 1992, that each of the hereinbefore mentioned deposited microorganisms is viable and capable of reproduction.

These deposits are available to the public upon the grant of a patent to the assignee, the University of Pittsburgh of the Commonwealth System of Higher Education, disclosing them. However, it should be understood that the availability of these deposits does not constitute a license to practice this invention in derogation of patent rights granted by governmental action.

What is claimed is:

1. A method of treating a vascular occlusion within a mammalian host which comprises transferring an isolated nucleic acid polymer inserted into a viral or plasmid vector to a population of mammalian cells at the site of said occlusion, said nucleic acid polymer encoding a biologically active nitric oxide synthase which has the enzymatic activity of the iNOS of SEQ ID NO:2 such that said nucleic acid polymer is expressed in said cells to effect increased amounts of nitric oxide (NO) via iNOS catalysis in amounts and for a time sufficient to reduce said vascular occlusion.

2. The method of claim 1 wherein said mammalian host is a human.

3. The method of claim 2 wherein said isolated nucleic acid polymer is an isolated human DNA sequence of SEQ ID NO:2.

4. The method of claim 1 wherein said population of mammalian cells are in situ mammalian cells selected from the group consisting of endothelial cells and vascular smooth muscle cells.

5. The method of claim 4 which further comprises clearing said occlusion by procedure selected from the group consisting of balloon angioplasty, mechanical endarterectomy and vascular endoscopy.

6. The method of claim 5 which further comprises utilizing a double balloon catheter to physically segregate the site of said occlusion and for delivering said vector to said cells.

7. The method of claim 6 wherein said vector is a recombinant viral vector.

8. The method of claim 6 wherein said vector is a recombinant viral vector.

9. The method of claim 7 wherein said recombinant vector is a recombinant MoMLV retroviral vector.

10. The method of claim 8 wherein said recombinant vector is a recombinant MoMLV retroviral vector.

11. The method of claim 9 wherein said recombinant MoMLV vector is MFG-iNOS.

12. The method of claim 9 wherein said recombinant MoMLV vector is DFG-iNOS-Neo.

13. The method of claim 10 wherein said recombinant MoMLV vector is MFG-iNOS.

14. The method of claim 10 wherein said recombinant MoMLV vector is DFG-iNOS-Neo.

15. The method of claim 1 wherein said vector is a recombinant plasmid DNA vector.

16. The method of claim 15 wherein said recombinant plasmid DNA vector is pCIS-iNOS.

17. The method of claim 7 wherein said recombinant viral vector is an adenovirus vector.

18. The method of claim 7 wherein said recombinant viral vector is an adeno-associated virus vector.

19. A method of treating an occlusion of an arterial vessel which comprises:

(a) clearing the site in said arterial vessel of occluding material; and (b) delivering an isolated nucleic acid polymer inserted into a viral or plasmid vector to a population of mammalian cells at the cleared occluded site in the arterial vessel, said nucleic acid polymer encoding a biologically active nitric oxide synthase which has the enzymatic activity of the iNOS of SEQ ID NO:2, such that said nucleic acid polymer is expressed in said cells at said cleared occluded site to effect an increased amount of nitric oxide (NO) via iNOS catalysis in amounts and for a time sufficient to attenuate vascular occlusion.

20. The method of claim 19 wherein step (a) is accomplished by a procedure selected from the group consisting of balloon angioplasty, mechanical endarcterectomy and vascular endoscopy.

21. The method of claim 20 wherein a double balloon catheter is used to physically segregate the cleared site of said artery.

22. The method of claim 19 wherein said vector is a recombinant viral vector.

23. The method of claim 22 wherein said recombinant vector is a recombinant MoMLV retroviral vector.

24. The method of claim 23 wherein said recombinant MoMLV vector is MFG-iNOS.

25. The method of claim 23 wherein said recombinant MoMLV vector is DFG-iNOS-Neo.

26. The method of claim 19 wherein said vector is a recombinant plasmid DNA vector.

27. The method of claim 26 wherein said recombinant plasmid DNA vector is pCIS-iNOS.

28. The method of claim 22 wherein said recombinant viral vector is an adenovirus vector.

29. The method of claim 22 wherein said recombinant viral vector is an adeno-associated virus vector.

30. A method of treating a blood vessel occlusion which comprises:

(a) forming a graft composed of a bypass vessel joined by proximal and distal anastomoses to bypass said occlusion;

(b) isolating an anastomosis subsequent to graft suturing; and (c) delivering an isolated nucleic acid polymer inserted into a viral or plasmid vector to a population of mammalian cells at the site of said isolated anastomosis, said nucleic acid polymer encoding a biologically active nitric oxide synthase which has the enzymetic activity of the iNOS of SEQ ID NO:2, such that said nucleic acid polymer is expressed in said cells at said site to effect an increased amount of nitric oxide (NO) via iNOS catalysis in amounts and for a time sufficient to attenuate vascular occlusion.

31. The method of claim 30 wherein said anastomosis of step (b) is said distal anastomosis.

32. The method of claim 31 wherein a double balloon catheter is used to physically isolate said anastomosis.

33. The method of claim 31 wherein said vector is a recombinant viral vector.

34. The method of claim 33 wherein said recombinant vector is a recombinant MoMLV retroviral vector.

35. The method of claim 34 wherein said recombinant MoMLV vector is MFG-iNOS.

36. The method of claim 34 wherein said recombinant MoMLV vector is DFG-iNOS-Neo.

37. The method of claim 31 wherein said vector is a recombinant plasmid DNA vector.

38. The method of claim 37 wherein said recombinant DNA vector is pCIS-iNOS.

39. The method of claim 33 wherein said recombinant viral vector is an adenovirus vector.

40. The method of claim 33 wherein said recombinant viral vector is an adeno-associated virus vector.

* * * * *

UNITED STATES PATENT AND TRADEMARK OFFICE
CERTIFICATE OF CORRECTION

PATENT NO : 5,658,565
DATED : August 19, 1997
INVENTOR(S) : Timothy R. Billiar et al.

It is certified that error appears in the above-identified patent and that said Letters Patent is hereby corrected as shown below:

Column 19, line 13: "cytomegalovirns" should read --cytomegalovirus--.
Column 20, line 36: "ethyl]" should read --ethryl]--.
Column 21, line 12: "lumina/" should read --luminal--.
Column 22, line 31: "skilled" should read --skilled artisan.--.
Column 28, line 6: "CDNA" should read --cDNA--.
Column 29, line 51: "pol" should read --pol--.
Column 30, line 3: "(Bell)" should read --(BeII)--.
Column 30, line 27: "ICo" should read --Kb--.
Column 30, line 28: "Y" should read --3'--.
Column 30, line 31: "K1" should read --RI--.
Column 30, line 45: "NOS" should read --iNOS--.
Column 30, line 67: "GRIP" should read --CRIP--.

IN THE CLAIMS:
In Claim 7, column 49, line 41: "6" should read --1--.
In Claim 33, column 51, line 3: "31" should read --30--.
In Claim 37, column 52, line 1: "31" should read --30--.

UNITED STATES PATENT AND TRADEMARK OFFICE
CERTIFICATE OF CORRECTION

PATENT NO : 5,658,565
DATED : August 19, 1997
INVENTOR(S) : Timothy R. Billiar et al.

It is certified that error appears in the above-identified patent and that said Letters Patent is hereby corrected as shown below:

ON THE TITLE PAGE:
[56] References Cited
U.S. Patent Documents, line 1, "Shuehr et al." should read
  --Stuehr et al.--.
Other Publications, line 23, "Vasodilatatin" should read --Vasodilatation--.
Other Publications, page 2, column 1, line 31, "biochem" should read --Biochem--.
Other Publications, page 2, column 2, line 7, "GouldFogerite" should read
  --Gould-Fogerite--.
Other Publications, page 2, column 2, line 15, "Mulligen" should read --Mulligan--.

IN THE DRAWINGS:
FIGS. 1-5 should be deleted and the attached FIGS. 1A-11 substituted therefor.

IN THE SPECIFICATION:
Column 1, line 66: the numerals "1" and "1153" should not be bolded.
Column 2, line 49: "1196" should read --1136--.
Column 11, line 53: "eistronic" should read --cistronic--.
Column 13, line 57: "i(8-2)" should read --1(8-2)--.
Column 15, line 38: "done" should read --clone--.

Signed and Sealed this

Ninth Day of June, 1998

BRUCE LEHMAN

*Attest:*

*Attesting Officer*     Commissioner of Patents and Trademarks

```
CTGCTTTAAA ATCTCTCGGC CACCTTTGAT GAGGGGACTG GGCAGTTCTA GACAGTCCCG   60
AAGTTCTCAA GGCACAGGTC TCTTCCTGGT TTGACTGTCC TTACCCCGGG GAGGCAGTGC  120
AGCCAGCTGC AAGCCCCACA GTGAAGAACA TCTGAGCTCA AATCCAGATA AGTGACATAA  180
GTGACCTGCT TTGTAAAGCC ATAGAG ATG GCC TGT CCT TGG AAA TTT CTG TTC  233
                             Met Ala Cys Pro Trp Lys Phe Leu Phe
                              1               5
AAG ACC AAA TTC CAC CAG TAT GCA ATG AAT GGG GAA AAA GAC ATC AAC   281
Lys Thr Lys Phe His Gln Tyr Ala Met Asn Gly Glu Lys Asp Ile Asn
 10              15                  20                  25

AAC AAT GTG GAG AAA GCC CCC TGT GCC ACC TCC AGT CCA GTG ACA CAG   329
Asn Asn Val Glu Lys Ala Pro Cys Ala Thr Ser Ser Pro Val Thr Gln
             30                  35                  40

GAT GAC CTT CAG TAT CAC AAC CTC AGC AAG CAG CAG AAT GAG TCC CCG   377
Asp Asp Leu Gln Tyr His Asn Leu Ser Lys Gln Gln Asn Glu Ser Pro
             45                  50                  55

CAG CCC CTC GTG GAG ACG GGA AAG AAG TCT CCA GAA TCT CTG GTC AAG   425
Gln Pro Leu Val Glu Thr Gly Lys Lys Ser Pro Glu Ser Leu Val Lys
             60                  65                  70

CTG GAT GCA ACC CCA TTG TCC TCC CCA CGG CAT GTG AGG ATC AAA AAC   473
Leu Asp Ala Thr Pro Leu Ser Ser Pro Arg His Val Arg Ile Lys Asn
         75                  80                  85

TGG GGC AGC GGG ATG ACT TTC CAA GAC ACA CTT CAC CAT AAG GCC AAA   521
Trp Gly Ser Gly Met Thr Phe Gln Asp Thr Leu His His Lys Ala Lys
 90                  95                 100                 105

GGG ATT TTA ACT TGC AGG TCC AAA TCT TGC CTG GGG TCC ATT ATG ACT   569
Gly Ile Leu Thr Cys Arg Ser Lys Ser Cys Leu Gly Ser Ile Met Thr
                 110                 115                 120

CCC AAA AGT TTG ACC AGA GGA CCC AGG GAC AAG CCT ACC CCT CCA GAT   617
Pro Lys Ser Leu Thr Arg Gly Pro Arg Asp Lys Pro Thr Pro Pro Asp
                 125                 130                 135
```

FIG. 1A

| | |
|---|---|
| GAG CTT CTA CCT CAA GCT ATC GAA TTT GTC AAC CAA TAT TAC GGC TCC<br>Glu Leu Leu Pro Gln Ala Ile Glu Phe Val Asn Gln Tyr Tyr Gly Ser<br>140 145 150 | 665 |
| TTC AAA GAG GCA AAA ATA GAG GAA CAT CTG GCC AGG GTG GAA GCG GTA<br>Phe Lys Glu Ala Lys Ile Glu Glu His Leu Ala Arg Val Glu Ala Val<br>155 160 165 | 713 |
| ACA AAG GAG ATA GAA ACA ACA GGA ACC TAC CAA CTG ACG GGA GAT GAG<br>Thr Lys Glu Ile Glu Thr Thr Gly Thr Tyr Gln Leu Thr Gly Asp Glu<br>170 175 180 185 | 761 |
| CTC ATC TTC GCC ACC AAG CAG GCC TGG CGC AAT GCC CCA CGC TGC ATT<br>Leu Ile Phe Ala Thr Lys Gln Ala Trp Arg Asn Ala Pro Arg Cys Ile<br>190 195 200 | 809 |
| GGG AGG ATC CAG TGG TCC AAC CTG CAG GTC TTC GAT GCC CGC AGC TGT<br>Gly Arg Ile Gln Trp Ser Asn Leu Gln Val Phe Asp Ala Arg Ser Cys<br>205 210 215 | 857 |
| TCC ACT GCC CGG GAA ATG TTT GAA CAC ATC TGC AGA CAC GTG CGT TAC<br>Ser Thr Ala Arg Glu Met Phe Glu His Ile Cys Arg His Val Arg Tyr<br>220 225 230 | 905 |
| TCC ACC AAC AAT GGC AAC ATC AGG TCG GCC ATC ACC GTG TTC CCC CAG<br>Ser Thr Asn Asn Gly Asn Ile Arg Ser Ala Ile Thr Val Phe Pro Gln<br>235 240 245 | 953 |
| CGG AGT GAT GGC AAG CAC GAC TTC CGG GTG TGG AAT GCT CAG CTC ATC<br>Arg Ser Asp Gly Lys His Asp Phe Arg Val Trp Asn Ala Gln Leu Ile<br>250 255 260 265 | 1001 |
| CGC TAT GCT GGC TAC CAG ATG CCA GAT GGC AGC ATC AGA GGG GAC CCT<br>Arg Tyr Ala Gly Tyr Gln Met Pro Asp Gly Ser Ile Arg Gly Asp Pro<br>270 275 280 | 1049 |
| GCC AAC GTG GAA TTC ACT CAG CTG TGC ATC GAC CTG GGC TGG AAG CCC<br>Ala Asn Val Glu Phe Thr Gln Leu Cys Ile Asp Leu Gly Trp Lys Pro<br>285 290 295 | 1097 |
| AAG TAC GGC CGC TTC GAT GTG GTC CCC CTG GTC CTG CAG GCC AAT GGC<br>Lys Tyr Gly Arg Phe Asp Val Val Pro Leu Val Leu Gln Ala Asn Gly<br>300 305 310 | 1145 |

FIG.—1B

```
CGT GAC CCT GAG CTC TTC GAA ATC CCA CCT GAC CTT GTG CTT GAG GTG      1193
Arg Asp Pro Glu Leu Phe Glu Ile Pro Pro Asp Leu Val Leu Glu Val
    315                 320                 325

GCC ATG GAA CAT CCC AAA TAC GAG TGG TTT CGG GAA CTG GAG CTA AAG      1241
Ala Met Glu His Pro Lys Tyr Glu Trp Phe Arg Glu Leu Glu Leu Lys
330                 335                 340                 345

TGG TAC GCC CTG CCT GCA GTG GCC AAC ATG CTG CTT GAG GTG GGC GGC      1289
Trp Tyr Ala Leu Pro Ala Val Ala Asn Met Leu Leu Glu Val Gly Gly
                350                 355                 360

CTG GAG TTC CCA GGG TGC CCC TTD AAT GGC TGG TAC ATG GGC ACA GAG      1337
Leu Glu Phe Pro Gly Cys Pro Phe Asn Gly Trp Tyr Met Gly Thr Glu
            365                 370                 375

ATC GGA GTC CGG GAC TTC TGT GAC GTC CAG CGC TAC AAC ATC CTG GAG      1385
Ile Gly Val Arg Asp Phe Cys Asp Val Gln Arg Tyr Asn Ile Leu Glu
        380                 385                 390

GAA GTG GGC AGG AGA ATG GGC CTG GAA ACG CAC AAG CTG GCC TCG CTC      1433
Glu Val Gly Arg Arg Met Gly Leu Glu Thr His Lys Leu Ala Ser Leu
    395                 400                 405

TGG AAA GAC CAG GCT GTC GTT GAG ATC AAC ATT GCT GTG ATC CAT AGT      1481
Trp Lys Asp Gln Ala Val Val Glu Ile Asn Ile Ala Val Ile His Ser
410                 415                 420                 425

TTT CAG AAG CAG AAT GTG ACC ATC ATG GAC CAC CAC TCG GCT GCA GAA      1529
Phe Gln Lys Gln Asn Val Thr Ile Met Asp His His Ser Ala Ala Glu
                430                 435                 440

TCC TTC ATG AAG TAC ATG CAG AAT GAA TAC CGG TCC CGT GGG GGC TGC      1577
Ser Phe Met Lys Tyr Met Gln Asn Glu Tyr Arg Ser Arg Gly Gly Cys
            445                 450                 455

CCG GCA GAC TGG ATT TGG CTG GTC CCT CCC ATG TCT GGG AGC ATC ACC      1625
Pro Ala Asp Trp Ile Trp Leu Val Pro Pro Met Ser Gly Ser Ile Thr
        460                 465                 470

CCC GTG TTT CAC CAG GAG ATG CTG AAC TAC GTC CTG TCC CCT TTC TAC      1673
Pro Val Phe His Gln Glu Met Leu Asn Tyr Val Leu Ser Pro Phe Tyr
    475                 480                 485
```

FIG. 1C

| | |
|---|---|
| TAC TAT CAG GTA GAG GCC TGG AAA ACC CAT GTC TGG CAG GAC GAG AAG<br>Tyr Tyr Gln Val Glu Ala Trp Lys Thr His Val Trp Gln Asp Glu Lys<br>490              495              500              505 | 1721 |
| CGG AGA CCC AAG AGA AGA GAG ATT CCA TTG AAA GTC TTG GTC AAA GCT<br>Arg Arg Pro Lys Arg Arg Glu Ile Pro Leu Lys Val Leu Val Lys Ala<br>          510                515               520 | 1769 |
| GTG CTC TTT GCC TGT ATG CTG ATG CGC AAG ACA ATG GCG TCC CGA GTC<br>Val Leu Phe Ala Cys Met Leu Met Arg Lys Thr Met Ala Ser Arg Val<br>         525               530              535 | 1817 |
| AGA GTC ACC ATC CTC TTT GCG ACA GAG ACA GGA AAA TCA GAG GCG CTG<br>Arg Val Thr Ile Leu Phe Ala Thr Glu Thr Gly Lys Ser Glu Ala Leu<br>        540              545              550 | 1865 |
| GCC TGG GAC CTG GGG GCC TTA TTC AGC TGT GCC TTC AAC CCC AAG GTT<br>Ala Trp Asp Leu Gly Ala Leu Phe Ser Cys Ala Phe Asn Pro Lys Val<br>    555              560              565 | 1913 |
| GTC TGC ATG GAT AAG TAC AGG CTG AGC TGC CTG GAG GAG GAA CGG CTG<br>Val Cys Met Asp Lys Tyr Arg Leu Ser Cys Leu Glu Glu Glu Arg Leu<br>570              575              580              585 | 1961 |
| CTG TTG GTG GTG ACC AGT ACG TTT GGC AAT GGA GAC TGC CCT GGC AAT<br>Leu Leu Val Val Thr Ser Thr Phe Gly Asn Gly Asp Cys Pro Gly Asn<br>               590              595              600 | 2009 |
| GGA GAG AAA CTG AAG AAA TCG CTC TTC ATG CTG AAA GAG CTC AAC AAC<br>Gly Glu Lys Leu Lys Lys Ser Leu Phe Met Leu Lys Glu Leu Asn Asn<br>        605              610              615 | 2057 |
| AAA TTC AGG TAC GCT GTG TTT GGC CTC GGC TCC AGC ATG TAC CCT CGG<br>Lys Phe Arg Tyr Ala Val Phe Gly Leu Gly Ser Ser Met Tyr Pro Arg<br>        620              625              630 | 2105 |
| TTC TGC GCC TTT GCT CAT GAC ATT GAT CAG AAG CTG TCC CAC CTG GGG<br>Phe Cys Ala Phe Ala His Asp Ile Asp Gln Lys Leu Ser His Leu Gly<br>        635              640              645 | 2153 |
| GCC TCT CAG CTC ACC CCG ATG GGA GAA GGG GAT GAG CTC AGT GGG CAG<br>Ala Ser Gln Leu Thr Pro Met Gly Glu Gly Asp Glu Leu Ser Gly Gln<br>650              655              660              665 | 2201 |
| GAG GAC GCC TTC CGC AGC TGG GCC GTG CAA ACC TTC AAG GCA GCC TGT<br>Glu Asp Ala Phe Arg Ser Trp Ala Val Gln Thr Phe Lys Ala Ala Cys<br>          670              675              680 | 2249 |

FIG. 1D

| | | | | | | | | | | | | | | | | |
|---|---|---|---|---|---|---|---|---|---|---|---|---|---|---|---|---|
|GAG|ACG|TTT|GAT|GTC|CGA|GGC|AAA|CAG|CAC|ATT|CAG|ATC|CCC|AAG|CTC|2297|
|Glu|Thr|Phe|Asp 685|Val|Arg|Gly|Lys 690|Gln|His|Ile|Gln|Ile 695|Pro|Lys|Leu| |
|TAC|ACC|TCC|AAT|GTG|ACC|TGG|GAC|CCG|CAC|CAC|TAC|AGG|CTC|GTG|CAG|2345|
|Tyr|Thr|Ser 700|Asn|Val|Thr|Trp|Asp 705|Pro|His|His|Tyr|Arg 710|Leu|Val|Gln| |
|GAC|TCA|CAG|CCT|TTG|GAC|CTC|AGC|AAA|GCC|CTC|AGC|AGC|ATG|CAT|GCC|2393|
|Asp|Ser 715|Gln|Pro|Leu|Asp 720|Leu|Ser|Lys|Ala|Leu 725|Ser|Ser|Met|His|Ala| |
|AAG|AAC|GTG|TTC|ACC|ATG|AGG|CTC|AAA|TCT|CGG|CAG|AAT|CTA|CAA|AGT|2441|
|Lys 730|Asn|Val|Phe|Thr|Met 735|Arg|Leu|Lys|Ser|Arg 740|Gln|Asn|Leu|Gln|Ser 745| |
|CCG|ACA|TCC|AGC|CGT|GCC|ACC|ATC|CTG|GTG|GAA|CTC|TCC|TGT|GAG|GAT|2489|
|Pro|Thr|Ser|Ser|Arg 750|Ala|Thr|Ile|Leu|Val 755|Glu|Leu|Ser|Cys|Glu 760|Asp| |
|GGC|CAA|GGC|CTG|AAC|TAC|CTG|CCG|GGG|GAG|CAC|CTT|GGG|GTT|TGC|CCA|2537|
|Gly|Gln|Gly|Leu 765|Asn|Tyr|Leu|Pro|Gly 770|Glu|His|Leu|Gly|Val 775|Cys|Pro| |
|GGC|AAC|CAG|CCG|GCC|CTG|GTC|CAA|GGC|ATC|CTG|GAG|CGA|GTG|GTG|GAT|2585|
|Gly|Asn|Gln 780|Pro|Ala|Leu|Val|Gln 785|Gly|Ile|Leu|Glu|Arg 790|Val|Val|Asp| |
|GGC|CCC|ACA|CCC|CAC|CAG|ACA|GTG|CGC|CTG|GAG|GAC|CTG|GAT|GAG|AGT|2633|
|Gly|Pro 795|Thr|Pro|His|Gln|Thr 800|Val|Arg|Leu|Glu|Asp 805|Leu|Asp|Glu|Ser| |
|GGC|AGC|TAC|TGG|GTC|AGT|GAC|AAG|AGG|CTG|CCC|CCC|TGC|TCA|CTC|AGC|2681|
|Gly 810|Ser|Tyr|Trp|Val|Ser 815|Asp|Lys|Arg|Leu|Pro 820|Pro|Cys|Ser|Leu|Ser 825| |
|CAG|GCC|CTC|ACC|TAC|TCC|CCG|GAC|ATC|ACC|ACA|CCC|CCA|ACC|CAG|CTG|2729|
|Gln|Ala|Leu|Thr|Tyr 830|Ser|Pro|Asp|Ile|Thr 835|Thr|Pro|Pro|Thr|Gln 840|Leu| |
|CTG|CTC|CAA|AAG|CTG|GCC|CAG|GTG|GCC|ACA|GAA|GAG|CCT|GAG|AGA|CAG|2777|
|Leu|Leu|Gln|Lys 845|Leu|Ala|Gln|Val|Ala 850|Thr|Glu|Glu|Pro|Glu 855|Arg|Gln| |

FIG. 1E

```
AGG CTG GAG GCC CTG TGC CAG CCC TCA GAG TAC AGC AAG TGG AAG TTC    2825
Arg Leu Glu Ala Leu Cys Gln Pro Ser Glu Tyr Ser Lys Trp Lys Phe
            860             865             870

ACC AAC AGC CCC ACA TTC CTG GAG GTG CTA GAG GAG TTC CCG TCC CTG    2873
Thr Asn Ser Pro Thr Phe Leu Glu Val Leu Glu Glu Phe Pro Ser Leu
        875             880             885

CGG GTG TCT GCT GGC TTC CTG CTT TCC CAG CTC CCC ATT CTG AAG CCC    2921
Arg Val Ser Ala Gly Phe Leu Leu Ser Gln Leu Pro Ile Leu Lys Pro
890             895             900             905

AGG TTC TAC TCC ATC AGC TCC TCC CGG GAT CAC ACG CCC ACG GAG ATC    2969
Arg Phe Tyr Ser Ile Ser Ser Ser Arg Asp His Thr Pro Thr Glu Ile
                910             915             920

CAC CTG ACT GTG GCC GTG GTC ACC TAC CAC ACC GGA GAT GGC CAG GGT    3017
His Leu Thr Val Ala Val Val Thr Tyr His Thr Gly Asp Gly Gln Gly
            925             930             935

CCC CTG CAC CAC GGT GTC TGC AGC ACA TGG CTC AAC AGC CTG AAG CCC    3065
Pro Leu His His Gly Val Cys Ser Thr Trp Leu Asn Ser Leu Lys Pro
        940             945             950

CAA GAC CCA GTG CCC TGC TTT GTG CGG AAT GCC AGC GCC TTC CAC CTC    3113
Gln Asp Pro Val Pro Cys Phe Val Arg Asn Ala Ser Ala Phe His Leu
    955             960             965

CCC GAG GAT CCC TCC CAT CCT TGC ATC CTC ATC GGG CCT GGC ACA GGC    3161
Pro Glu Asp Pro Ser His Pro Cys Ile Leu Ile Gly Pro Gly Thr Gly
970             975             980             985

ATC GTG CCC TTC CGC AGT TTC TGG CAG CAA CGG CTC CAT GAC TCC CAG    3209
Ile Val Pro Phe Arg Ser Phe Trp Gln Gln Arg Leu His Asp Ser Gln
                990             995             1000

CAC AAG GGA GTG CGG GGA GGC CGC ATG ACC TTG GTG TTT GGG TGC CGC    3257
His Lys Gly Val Arg Gly Gly Arg Met Thr Leu Val Phe Gly Cys Arg
            1005            1010            1015

CGC CCA GAT GAG GAC CAC ATC TAC CAG GAG GAG ATG CTG GAG ATG GCC    3305
Arg Pro Asp Glu Asp His Ile Tyr Gln Glu Glu Met Leu Glu Met Ala
        1020            1025            1030

CAG AAG GGG GTG CTG CAT GCG GTG CAC ACA GCC TAT TCC CGC CTG CCT    3353
Gln Lys Gly Val Leu His Ala Val His Thr Ala Tyr Ser Arg Leu Pro
    1035            1040            1045
```

FIG. 1F

```
GGC AAG CCC AAG GTC TAT GTT CAG GAC ATC CTG CGG CAG CAG CTG GCC    3401
Gly Lys Pro Lys Val Tyr Val Gln Asp Ile Leu Arg Gln Gln Leu Ala
1050            1055            1060            1065

AGC GAG GTG CTC CGT GTG CTC CAC AAG GAG CCA GGC CAC CTC TAT GTT    3449
Ser Glu Val Leu Arg Val Leu His Lys Glu Pro Gly His Leu Tyr Val
            1070            1075            1080

TGC GGG GAT GTG CGC ATG GCC CGG GAC GTG GCC CAC ACC CTG AAG CAG    3497
Cys Gly Asp Val Arg Met Ala Arg Asp Val Ala His Thr Leu Lys Gln
        1085            1090            1095

CTG GTG GCT GCC AAG CTG AAA TTG AAT GAG GAG CAG GTC GAG GAC TAT    3545
Leu Val Ala Ala Lys Leu Lys Leu Asn Glu Glu Gln Val Glu Asp Tyr
    1100            1105            1110

TTC TTT CAG CTC AAG AGC CAG AAG CGC TAT CAC GAA GAT ATC TTC GGT    3593
Phe Phe Gln Leu Lys Ser Gln Lys Arg Tyr His Glu Asp Ile Phe Gly
1115            1120            1125

GCT GTA TTT CCT TAC GAG GCG AAG AAG GAC AGG GTG GCG GTG CAG CCC    3641
Ala Val Phe Pro Tyr Glu Ala Lys Lys Asp Arg Val Ala Val Gln Pro
1130            1135            1140            1145

AGC AGC CTG GAG ATG TCA GCG CTC TGAGGGCCTA CAGGAGGGGT TAAAGCTGCC    3695
Ser Ser Leu Glu Met Ser Ala Leu
        1150

GGCACAGAAC TTAAGGATGG AGCCAGCTCT GCATTATCTG AGGTCACAGG GCCTGGGGAG   3755
ATGGAGGAAA GTGATATCCC CCAGCCTCAA GTCTTATTTC CTCAACGTTG CTCCCCATCA   3815
AGCCCTTTAC TTGACCTCCT AACAAGTAGC ACCCTGGATT GATCGGAGCC TCCTCTCTCA   3875
AACTGGGGCC TCCCTGGTCC CTTGGAGACA AAATCTTAAA TGCCAGGCCT GGCGAGTGGG   3935
TGAAAGATGG AACTTGCTGC TGAGTGCACC ACTTCAAGTG ACCACCAGGA GGTGCTATCG   3995
CACCACTGTG TATTTAACTG CCTTGTGTAC AGTTATTTAT GCCTCTGTAT TTAAAAAACT   4055
AACACCCAGT CTGTTCCCCA TGGCCACTTG GGTCTTCCCT GTATGATTCC TTGATGGAGA   4115
TATTTACATG AATTGCATTT TACTTTAATC                                    4145
```

FIG. 1G

FIG. 2

MFG-iNOS:

DFG-iNOS-Neo: